US011897918B2

(12) United States Patent
Ho et al.

(10) Patent No.: US 11,897,918 B2
(45) Date of Patent: Feb. 13, 2024

(54) COMPOSITIONS AND METHODS TO INCREASE PRODUCTION

(71) Applicant: Seqirus UK Limited, Berkshire (GB)

(72) Inventors: Samuel Ho, Cambridge, MA (US); David Parker, Cambridge, MA (US); Peter Fekkes, Cambridge, MA (US); Ivna De Souza, Cambridge, MA (US); Peter Mason, Cambridge, MA (US); Pirada Allen, Cambridge, MA (US)

(73) Assignee: Seqirus UK Limited, Berkshire (GB)

( * ) Notice: Subject to any disclaimer, the term of this patent is extended or adjusted under 35 U.S.C. 154(b) by 1171 days.

(21) Appl. No.: 16/297,895

(22) Filed: Mar. 11, 2019

(65) Prior Publication Data

US 2020/0040040 A1 Feb. 6, 2020

Related U.S. Application Data

(63) Continuation of application No. 15/304,650, filed as application No. PCT/EP2015/058533 on Apr. 20, 2015, now abandoned.

(30) Foreign Application Priority Data

Apr. 18, 2014 (EP) .................................... 14165334

(51) Int. Cl.

| | |
|---|---|
| ***C07K 14/005*** | (2006.01) |
| ***A61K 39/12*** | (2006.01) |
| ***A61K 39/145*** | (2006.01) |
| ***C12N 7/02*** | (2006.01) |
| ***C12N 7/00*** | (2006.01) |
| *A61K 39/00* | (2006.01) |

(52) U.S. Cl.

CPC ............ *C07K 14/005* (2013.01); *A61K 39/12* (2013.01); *A61K 39/145* (2013.01); *C12N 7/00* (2013.01); *C12N 7/02* (2013.01); *A61K 39/00* (2013.01); *A61K 2039/575* (2013.01); *C12N 2760/16111* (2013.01); *C12N 2760/16134* (2013.01); *C12N 2760/16143* (2013.01); *C12N 2760/16151* (2013.01); *C12N 2760/16234* (2013.01); *C12N 2760/16243* (2013.01); *C12N 2760/16251* (2013.01)

(58) Field of Classification Search

None

See application file for complete search history.

(56) References Cited

U.S. PATENT DOCUMENTS

2009/0318379 A1* 12/2009 Prendergast ........... A61K 31/22 514/459

FOREIGN PATENT DOCUMENTS

| | | | |
|---|---|---|---|
| JP | 2009-292801 | A | 12/2009 |
| WO | WO 2012/136852 | A1 | 10/2012 |
| WO | WO 2014/033546 | A2 | 3/2014 |

OTHER PUBLICATIONS

Kumaki et al., Effect of statin treatments on highly pathogenic avian influenza H5N1, seasonal and H1N1pdm09 virus infections in BALB/c mice, 2012, Future Virology, vol. 7, No. 8, pp. 801-818.*

Episcopio et al., Atorvastatin restricts the ability of influenza virus to generate lipid droplets and severely suppresses the replication of the virus, FASEB J, 2019, vol. 33, No. 8, pp. 9516-9525.*

Morikawa et al., "The effect of statins on mRNA levels of genes related to inflammation, coagulation, and vascular constriction in HUVEC," J Atheroscler Thromb, 9(4):178.183, (2002).

Peng et al., "Protective effect of fluvastatin on influenza virus infection," Mol Med Rep., 9(6):2221-2226, (2014).

International Search Report for International Application No. PCT/EP2015/058533, dated Jul. 16, 2015.

Written Opinion for International Application No. PCT/EP2015/058533.

* cited by examiner

*Primary Examiner* — Benjamin P Blumel

(74) *Attorney, Agent, or Firm* — Finnegan, Henderson, Farabow, Garrett & Dunner, LLP

(57) ABSTRACT

Disclosed herein are methods for increasing protein yield and cellular productivity. Chemical agents facilitate host cell production of biological molecules to increase product yield.

14 Claims, 23 Drawing Sheets

Sulphonamide in vaccine monobulk

FIG. 6A(contd)
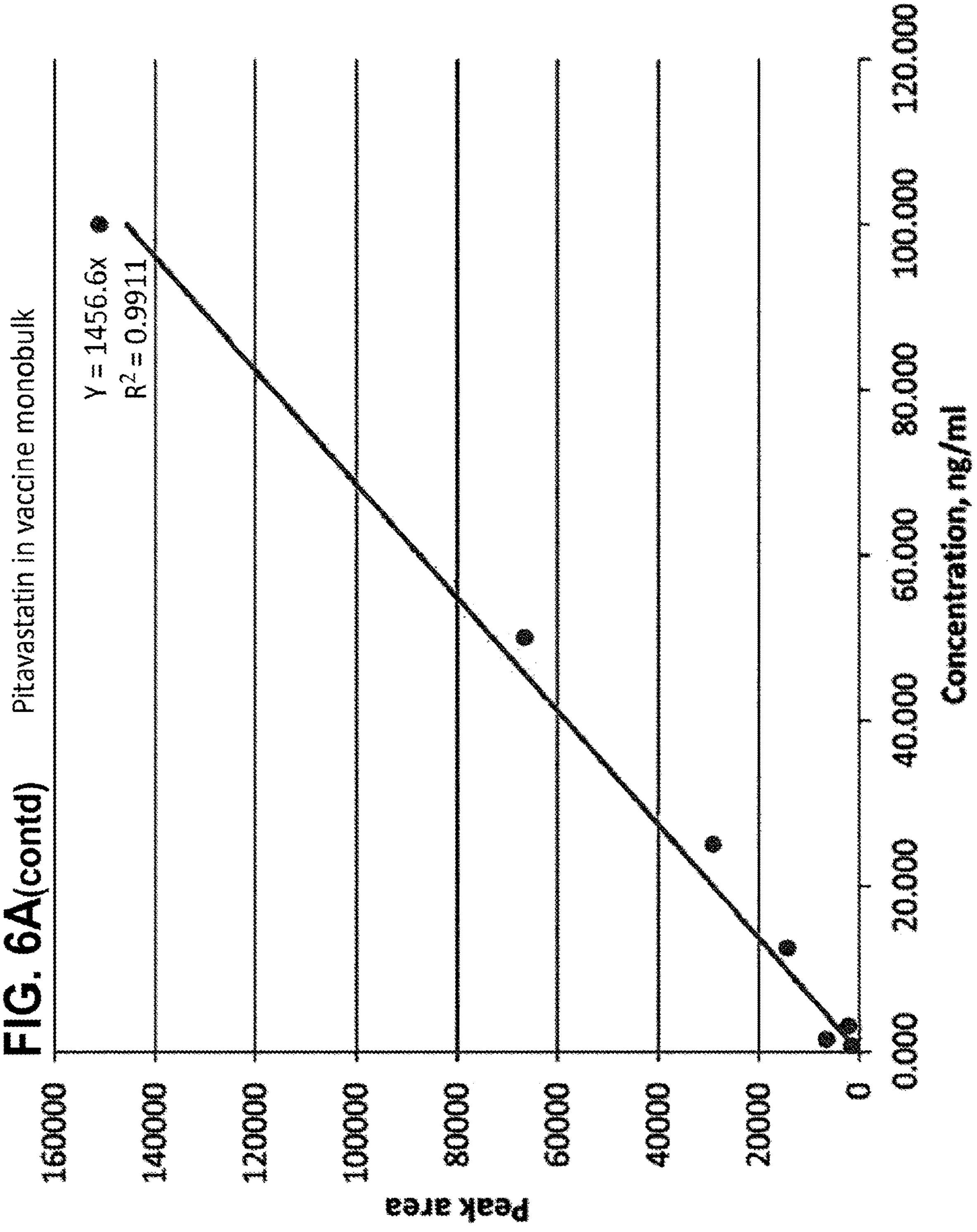

FIG. 6B (contd)
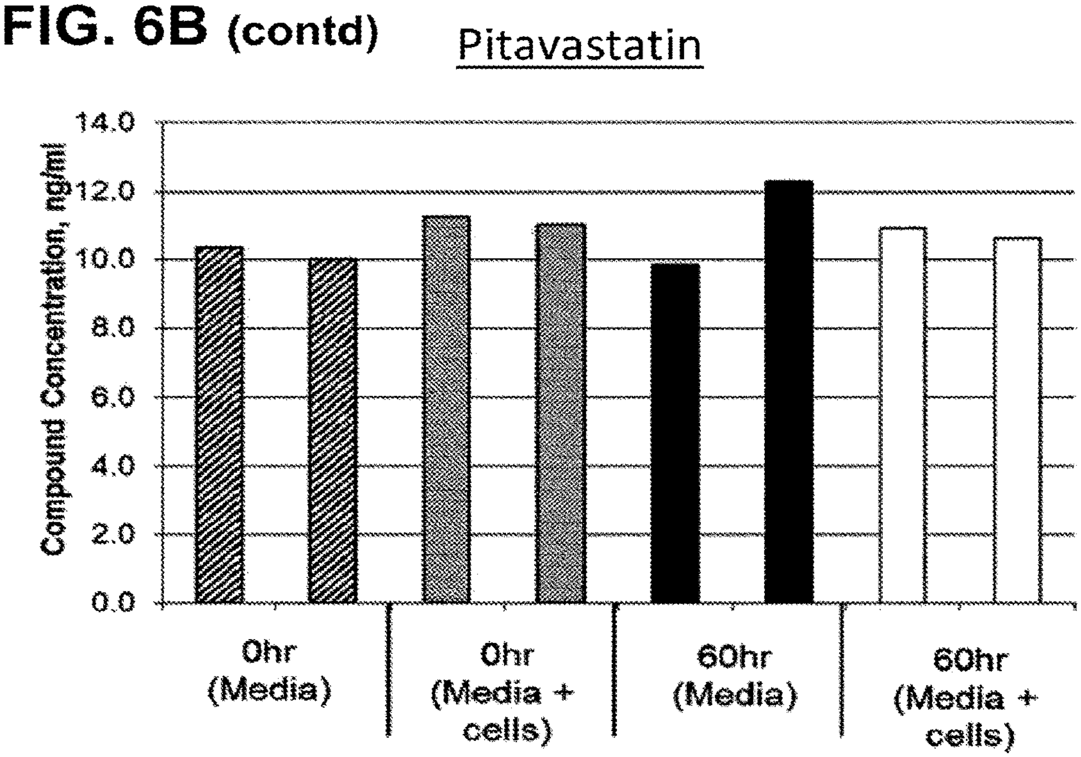
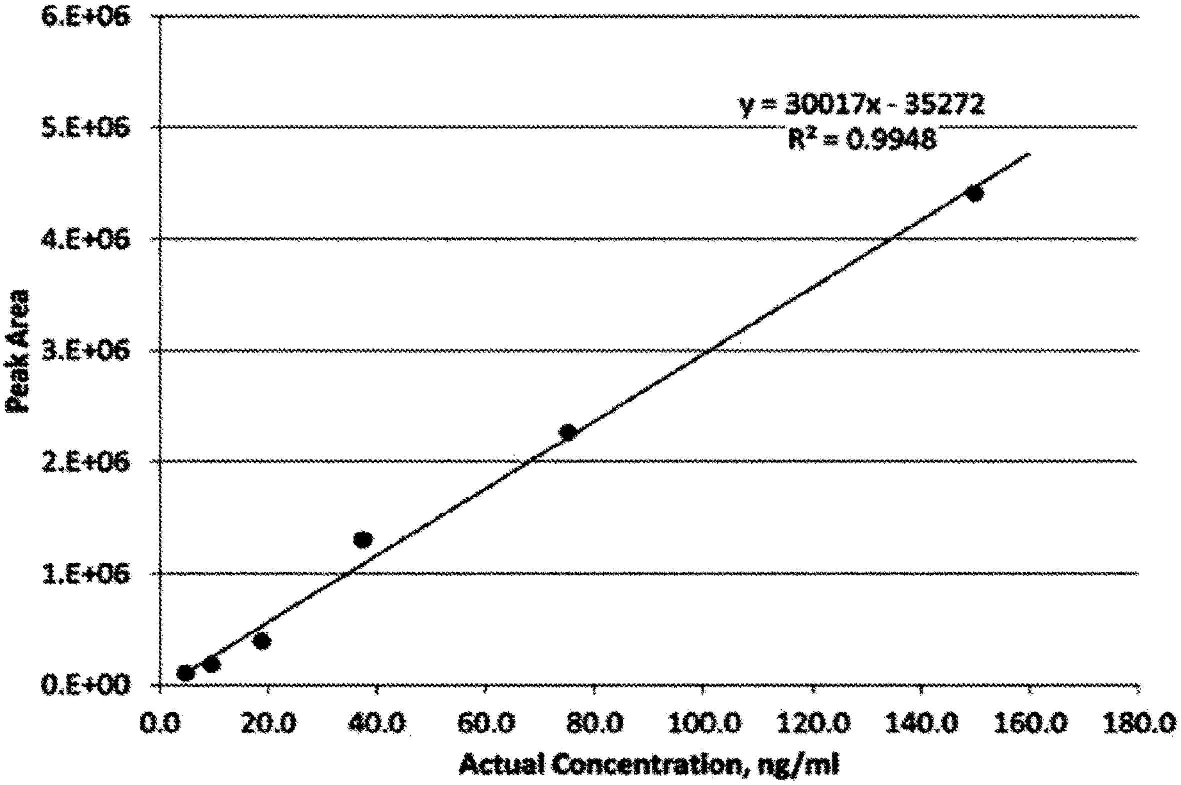

FIG. 6C

| Virus strain | Drug | Process Step | Concentration (ng/ml) | Total drug amount (ngs) | % drug (based on pre-purification amounts normalized to 100%) |
|---|---|---|---|---|---|
| | | | | | |
| Flu A | Pitavastatin | Pre-purification | 15.53 | 528.02 | 100 |
| Flu A | Pitavastatin | Post-purification | 0.176 | 0.88 | 0.167 |
| Flu B | Pitavastatin | Pre-purification | 20.2 | 686.8 | 100 |
| Flu B | Pitavastatin | Post-purification | 0.34 | 1.7 | 0.248 |
| | | | | | |
| Flu A | Sulphonamide | Pre-purification | 344.58 | 11715.72 | 100 |
| Flu A | Sulphonamide | Post-purification | 2.246 | 11.23 | 0.096 |
| Flu B | Sulphonamide | Pre-purification | 679 | 23086 | 100 |
| Flu B | Sulphonamide | Post-purification | 1.968 | 9.84 | 0.043 |

5HT = serotonin (agonist of 5HT7 receptor)
XCD714 = SB269970 compound that is the most robust inverse agonist of 5HT7 receptor
AFZ = SB258741 compound that is a partial inverse agonist of 5HT7 receptor Risp = Risperidone, Queti = Quetiapine; Fluva = Fluvastatin; Amil = Amiloride; Prom = Promethazine

COMPOSITIONS AND METHODS TO INCREASE PRODUCTION

This application is a continuation application of U.S. application Ser. No. 15/304,650, filed Oct. 17, 2016, now abandoned, which is a U.S. national phase application of International Application No. PCT/EP2015/058533, filed Apr. 20, 2015, which claims the benefit of EP14165334.5, filed Apr. 18, 2014. The disclosure of each of the above applications is incorporated herein by reference in its entirety.

FIELD OF THE INVENTION

The invention generally relates to methods and compositions for producing biological molecules (e.g., biologics) in host cells, such as therapeutic, prophylactic and diagnostic proteins. The invention also relates to increasing the yield of biological molecules from cultured cells.

BACKGROUND OF THE INVENTION

Many biologics, such as therapeutic, prophylactic and diagnostic proteins, are produced in host cells. Vaccine antigens, e.g. for influenza vaccines, are often produced in mammalian cell or hens eggs (Govorkova, et al, Dev Biol Stand 98:39-51, (1998)). Similarly, many recombinant proteins, including monoclonal antibodies and peptide-based therapeutics, are produced in suitable host cells. Notwithstanding, the yield in these production systems often remains sub-optimal.

Several studies have been pursued to increase the yield of antigenic protein or virus produced from cell culture or eggs. Influenza manufacturers have incorporated 25 μg/ml hydrocortisone as an additive in the fresh inoculum used to infect embryonated eggs (International Patent Publication WO 02/074336). Treatment with small molecule compounds, drugs or proteins have been tested to increase production capacity of cell cultures. International Patent Publication WO 2012/134130 identified the interaction of CHD6 protein and influenza virus polymerase as a negative modulator of virus replication. CHD6 genes were silenced by transfecting influenza infected HEK293T or A549 cell lines with short hairpin RNA. This technique produced approximately a 5-10 fold increase in virus titer over control cells.

In another study, U.S. Pat. No. 7,132,271 discloses suppression of interferon-mediated antiviral responses, specifically double stranded RNA dependent kinases, could alter the permissiveness of cell cultures to induce increased viral reproduction. Stable or transient cells were modified to produce PKR-deficient or 2-5A synthetase-deficient mutations prior to infection with a virus. It is disclosed that EMCV (encephalomyocarditis virus) could be replicated in PKR-deficient cells at 0.001 TCID50/cell resulting in as much as one thousand fold increase in viral replication over control.

In US Patent Publication 2013-0315954, a method for improving production of an influenza virus is disclosed wherein production is carried out in the presence of a small molecule inhibitor of the interaction between the Mdm2 protein and the p53 protein. The small molecule compounds include imidazoline derivatives, imidazole derivatives, oxindole derivatives, spiroindolinone derivatives, quinolone derivatives, bisarylsulfonamide derivatives, benzodiapezine derivatives, piperidine derivatives, phenoxyacetic acid derivatives, phenoxymethyltetrazole derivatives, chalcone derivatives, tetrazole derivatives, disulfide derivatives, diaminoaryl derivatives and peptide inhibitors of Mdm2 proteins. In one particular experiment, an MDCK cell line was infected with an influenza H3N2 virus was treated with 0.1 μM, 1.0 μM, and 10 μM dihydroimidazole compound (Nutlin-3). Measurement of viral genome in the supernatant showed that at an initial multiplicity of infection (MOI) of $10^{-3}$, and a pretreatment with Nutlin at 24 hours post infection produced up to nineteen times more copies of viral genome in the supernatant compared with control.

International Patent Publication WO 2012/136852 discloses the use of pharmaceutical drugs to increase the production capacity influenza A virus in MDCK or A549 cells. After incubation with a drug for 24-48 hours post infection, viral titer and neuraminidase activity was measured. 0.01-10 μM Simvastatin was added prior to inoculation with influenza subtype A virus and produced an increase of approximately 1.5-3 fold H1N1 viral titer at 1.0 μM concentration. Only one influenza Subtype A strain (H1N1 but not H3N2 and H5N1) was shown to yield viral titer greater than approximately 1.5 fold in the Simvastatin treated cells. The increase in virus yield for other pharmaceutical drugs tested using influenza A strain, was strain, dose and/or drug dependent.

To date, no patent or literature describes using small molecule compounds at very low concentrations such as 0.05 μM or less to increase yield of biological molecules from host cell systems. There remains a need for robust manufacturing, increased production efficiencies and cost effective processing of biological products for therapeutic, prophylactic and diagnostic use.

SUMMARY OF THE INVENTION

The present invention generally provides methods that increase production of proteins suitable for use in pharmaceutical applications, such as diagnostic, therapeutic or prophylactic applications. The invention therefore is suitable for the manufacture of pharmaceutical products, e.g., biologics, including vaccines.

The invention encompasses in a broad sense the recognition that modulation of certain cellular pathway(s) in a host cell system can lead to enhanced production of biological molecules in the host. In some embodiments, compounds useful for carrying out the present invention may regulate protein lipidation (prenylation), cholesterol biosynthesis, and/or G-protein-coupled receptor signal transduction, such as intracellular cAMP-dependent signaling.

More specifically, in one aspect, the invention provides methods for increasing the yield of biological molecules, such as recombinant proteins and viral particles produced in host cell systems, by modulating the statin-associated cellular pathway. Without wishing to be bound by a particular theory, data presented herein suggest that the enhancement effect may be mediated via the mevalonate pathway, involving both cholesterol-dependent and cholesterol-independent mechanisms of action.

In another aspect, the invention provides methods for increasing the yield of biological molecules, such as recombinant proteins and viral particles produced in host cell systems, by modulating the dopamine- and/or serotonin-associated cellular pathway. In some embodiments, suitable compounds that affect the dopamine pathway and/or the serotonin pathway are selective ligands for one or more of the receptors, such as, agonists and antagonists (e.g., full agonists, partial agonists, neutral antagonists, inverse agonists, etc.). In some embodiments, such compounds act via at least one serotonin receptor, including but are not limited to, the 5-HT7, 5-HT1, and/or 5-HT5 receptor signaling in a host cell. In some embodiments, such compounds act via the 5-HT7 receptor signaling. In some embodiments, such compounds can reduce intracellular cAMP levels.

Surprisingly, the inventors of the present application have discovered that the observed enhancement effects are not limited to viral production in a host cell, nor are they to a particular cell line. Rather, the use of suitable compounds described herein (e.g., compounds that can modulate statin- and/or 5HTR-associated signaling, including statins and statin-like molecules, receptor ligands, structural analogs or derivatives, functional equivalents, and combinations thereof) may provide a more general means of increasing protein production in a variety of host cell systems. Furthermore, the inventors have identified certain molecules provided herein are effective in enhancing virus/protein production when used at surprisingly low concentrations. This is particularly advantageous for manufacturing pharmaceutical products that require a high degree of purity suitable for human use. Thus, such methods are suitable for commercial-scale production of biologics.

Accordingly methods are provided for producing proteins from host cell systems, such as cell cultures or embryonated eggs, comprising contacting/treating a host cell with at least one agent selected from Table 1. The residues for the compound are defined in detail further below.

TABLE 1

| Name | Structure |
| --- | --- |
| Formula 1<br>Fluvastatin and analogs thereof | 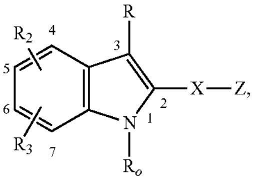 |
| Formula 2<br>Pitavastatin and related analogs thereof | 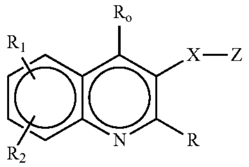 |
| Formula 3<br>Atorvastatin and analogs thereof | 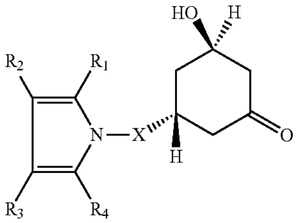 |
| Formula 4<br>Cerivastatin and analogs thereof | 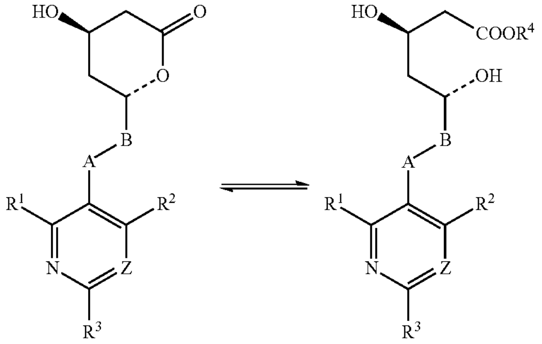<br>I II |

TABLE 1-continued

| Name | Structure |
|---|---|
| Formula 5 Lovastatin/Mevastatin and analogs thereof (in certain embodiments, excluding Simvastatin) | 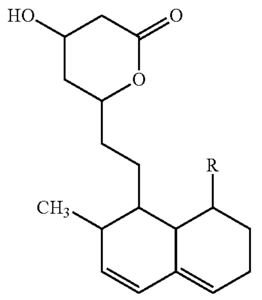 |
| Formula 6 Pravastatin and analogs thereof | 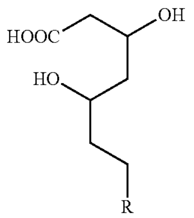 |
| Formula 7 Rosuvastatin and analogs thereof | 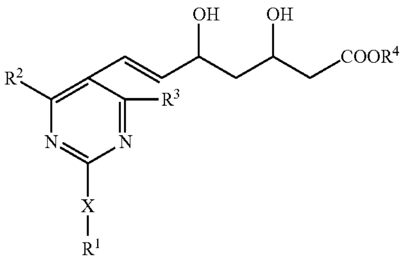 |
| Formula 8 Sulfonamides and analogs thereof | 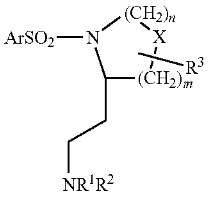 |
| Formula 9 Tropanol ester, tropamine amides analogs thereof | 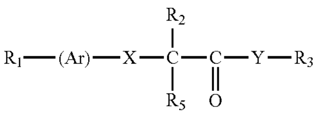 |
| Formula 10 Benzisothiazole, benzisoxazole and analogs thereof | 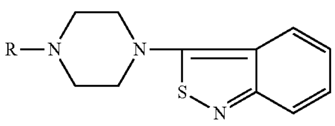 |
| Formula 11 Benzypyrans and analogs thereof | 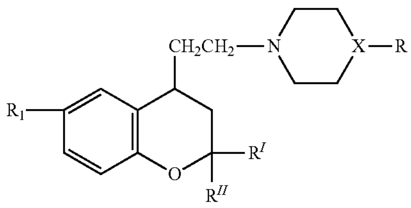 |

TABLE 1-continued

| Name | Structure |
|---|---|
| Formula 12 Tetrahydropyridine, piperidine and analogs thereof | 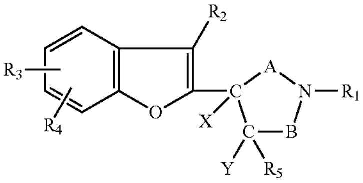 (I) |
| Formula 13 Dimethoxyphenyl-piperidinemethanol and analogs thereof | 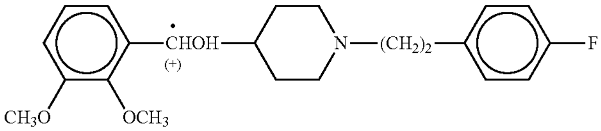 |

In some embodiments, at least one agent (e.g., one or more agents) is/are selected from the compounds provided in the table below to carry out the present invention.

TABLE 4

| COMPOUND | FORMULA | INCHI_KEY | STRUCTURE |
|---|---|---|---|
| Compound A BA003098-AA-1 | $C_{22}H_{25}NO_2$ | IUTYUDPWXQZWTH-UHFFFAOYSA-N | 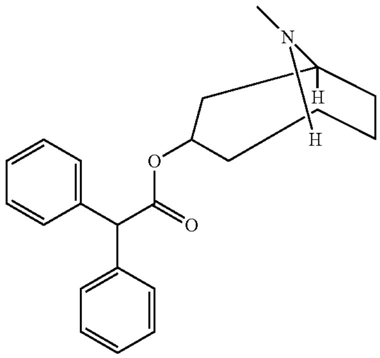 [SMILES: CNC1CCCCC(OC(=O)C(c2ccccc2)c2ccccc2)C1] |
| Compound B CGP006085A-AA-1 | $C_{15}H_{19}NO$ | UFGTZUKOBHLAAC-UHFFFAOYSA-N | 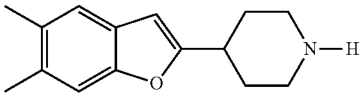 [SMILES: Cc1cc2cc(C3CCNCC3)oc2cc1C] |
| Compound C CGP033313-NX-1 | $C_{20}H_{24}F_3N_3O$ | DXIYSVWOHCXFHW-UHFFFAOYSA-N | 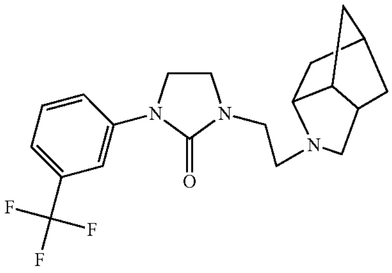 [SMILES: O=C1N(CCN2CC3CC4CC3C2C4)CCN1c1cccc(C(F)(F)F)c1] |

TABLE 4-continued
| COMPOUND | FORMULA | INCHI_KEY | STRUCTURE |
|---|---|---|---|
| Compound D CGS024212A-AG-1 (Pentamidine) | $C_{18}H_{21}N_3O_4$ | LDKDXQMFHSGLKV-UHFFFAOYSA-N | 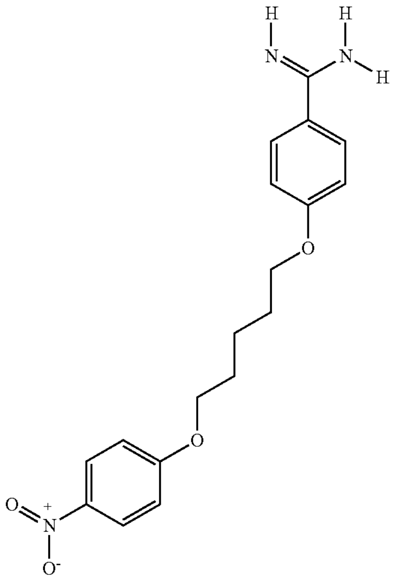 |
| Compound E NVP-AFZ077-NX-1 | $C_{19}H_{30}N_2O_2S$ | YVWGGGGMRDLOGA-GOSISDBHSA-N | 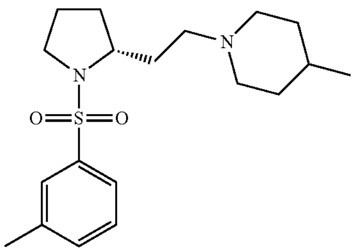 |
| Compound F NVP-AKS755-AH-1 | $C_{18}H_{25}NO_2S$ | HOVVTKGSYSJEIG-UHFFFAOYSA-N | 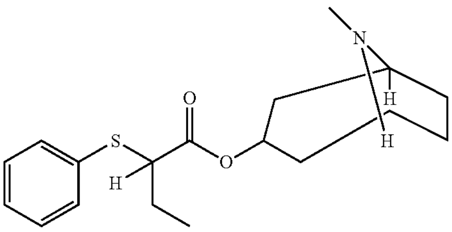 [SMILES: CCC(Sc1ccccc1)C(=O)OC1CCCCC(NC)C1] |
| Compound G NVP-BYF589-BA-1 (Pitavastatin) | $C_{25}H_{24}FNO_4$ | VGYFMXBACGZSIL-MCBHFWOFSA-N | 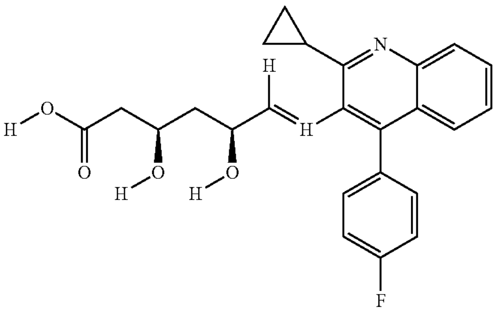 |

TABLE 4-continued

| COMPOUND | FORMULA | INCHI_KEY | STRUCTURE |
|---|---|---|---|
| Compound H PKF114-213-NX-1 (Tiospirone) | $C_{24}H_{32}N_4O_2S$ | ZFZPJDFBJFHYIV-UHFFFAOYSA-N | 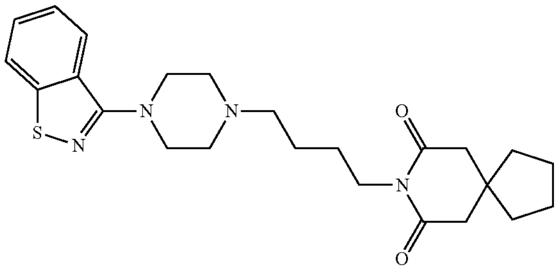 [SMILES: O=C1CC2(CCCC2)CC(=O)N1CCCCN1CCN(c2nsc3ccccc23)CC1] |
| Compound I PKF116-328-AE-1 (Terikalant) | $C_{24}H_{31}NO_3$ | UIZPEXQHMIZQPQ-IBGZPJMESA-N | 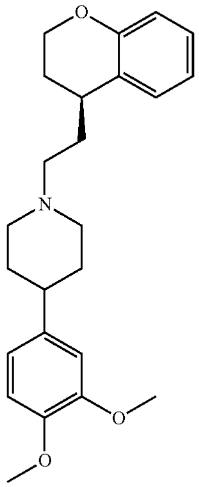 [SMILES: COc1ccc(C2CCN(CC[C@H]3CCOc4ccccc43)CC2)cc1OC] |
| Compound J PKF117-462-NX-1 (MDL 100907) | $C_{22}H_{28}NO_3F$ | HXTGXYRHXAGCFP-UHFFFAOYSA-N | 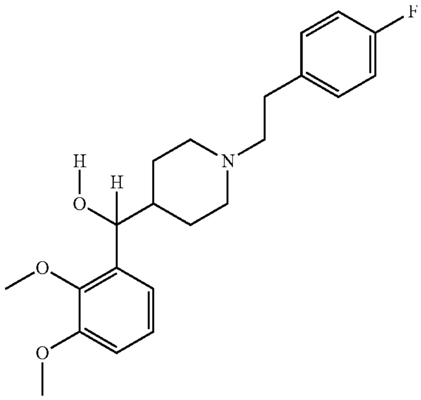 [SMILES: COc1cccc(C(O)C2CCN(CCc3ccc(F)cc3)CC2)c1OC] |

Both from commercial and safety standpoints, it is particularly advantageous to achieve enhanced protein yield in a host cell system (such as cell culture and eggs) by the use of compounds described herein at relatively low concentrations. Accordingly, the invention provides a method for producing biological molecules from host cell systems such as cell culture or eggs comprising contacting a host cell with at least one chemical agent such as a statin or a statin derivative at low concentrations. In some embodiments, the statin or the derivative is not Simvastatin. Such agent may be present in a final concentration between 0.001 μM-10 μM, preferably 0.05 μM or less when the host cell is a cell culture. When the host cell is an embryonated egg, the chemical agent may be present at a concentration of at least 10-20, 30, 40, 50, 60, 70, 80, 90, 100 μM per egg or greater.

Suitable chemical agents used in the invention are those which have therapeutic efficacy and are not toxic when used in cells or animals. It is particularly desirable that such compounds have well-characterized safety profiles for regulatory purposes. Thus, useful chemical agents may be selected from commercially available pharmaceutical drugs, which have been approved as safe for human use and thereby have undergone rigorous testing for toxicity and clearance. Such agents are particularly suited as growth enhancer in biological production systems. Accordingly, the methods of the invention encompass known pharmaceutical agents, chemical agents and analogs thereof described herein. Preferably, these agents are used in an amount effective to increase biological product yield by at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, or up to about 10-fold or greater than that seen with comparative control.

The method of the invention may also increase yield of biological molecules or biological products as produced herein by at least an increase in yield of at least 20%, 30%, 40%, 50%, 60%, 70%, 80%, 90%, 100%, 200%, 300%, 500% or greater compared to control. Preferably, the increase in yield can be measured by the amount of biological molecules produced such as total particles (vRNA copies/ml), infectious particles (IU/ml) or protein (μg/ml) in the culture supernatant compared to control. For influenza virus manufacture, preferably the increase in HA antigen yield is measured compared to control. For the purpose of this patent, the increase in yield is preferably measured by an ELISA detecting the target product to be produced, for flu vaccines an HA-ELISA.

Preferred chemical agents are those which are not highly metabolized by the host cells. The chemical agents are stable and do not substantially degrade in the presence of host cells, reagents and manufacturing conditions and can be traced by applicable assays throughout the production process. Methods for detecting clearance or degradation of chemical agents used in the host cell systems described herein are also provided.

Although the chemical agents should not be present in a purified sample (e.g., product), the agents can be traced during the manufacturing process. The agents are chemically stable and can be measured or detected in their unmetabolized form in the cell culture supernatant after 0 hours, 1 hour, 2 hours, 3 hours, 4 hours, 5 hours, 6 hours, 7 hours, 8 hours, 9 hours, 10 hours, 15 hours, 20 hours, 25 hours, 30 hours, 35 hours, 40 hours, 45 hours, 50 hours, 55 hours and 60 hours contact with a host cell. Preferably, the agents are not degraded as measured in the final product using mass spectrometry with a limit of detection of 0.5 ng/ml in pure solvent (approximately 50% acetonitrile). For flu vaccine production, unmetabolized chemical agents are absent or undetectable, i.e., at levels that cannot be detected at a limit of detection (LOD) of 0.5 ng/ml or less in pure solvent, in cell culture supernatant up to 60 hours post-infection (such as a low MOI virus infection of $10^{-3}$ or $10^{-4}$).

In some embodiments of the invention, a method is provided for manufacturing biological products, such as proteins and viruses of interest, in a host cell system, characterized in that manufacture is conducted in the presence of at least one chemical agent comprising a final concentration of 0.05 μM or less or whereby a 2-fold increase in the product, is achieved.

In some embodiments, the invention provides methods of manufacturing viruses from cell culture or embryonated eggs using at least one chemical agent having a final concentration in the range of 0.001 μM-1.0 μM and whereby at least a 2-fold increase in antigen production is achieved.

The invention has particular use and effect in influenza vaccine manufacture by improving viral growth, increasing cellular productivity, increasing viral titer, expression and/or yield of HA antigens. The method of the invention produces increased quantity and doses of antigenic products obtained per manufacturing batch. Accordingly, the invention provides a method for producing an influenza virus in host cells, preferably mammalian cells, more preferably cultured cells, characterized in that production is conducted in the presence of at least one agent having a concentration of 1 μM or less, preferably 0.05 μM or less, and whereby viral particles or antigens are produced at a yield of greater than 2-fold compared to control.

In some embodiments, the invention provides a method for producing an influenza B strain in host cell systems such as cell culture or embryonated eggs, characterized in that the production is conducted in the presence of an agent or a derivative thereof and produces a yield of viral particles or antigens greater than 2-fold compared to control In some embodiments, at least one chemical agent can be used to treat a host cell either prior to, concurrently with or post transfection/infection of a host cell by a virus or another vector. Host cells may be in contact with at least one chemical agent for a period of 0 to 1 hour, 0 to 2 hours, 0 to 3 hours, 0 to 4 hours, 0 to 5 hours, 0 to 12 hours, 0 to 20 hours, 0 to 30 hours, 0 to 40 hours, 0 to 50 hours, 0 to 60 hours prior to or post transfection/infection, so as to achieve an increase in the yield of a biological product of interest.

The invention further provides methods for increasing production of recombinant proteins (or fragments thereof) whose production yields are considered to be sub-optimal (e.g., "low yielders" and "mid-yielders") when expressed in certain host cells under typical growth conditions. Protein production is considered sub-optimal when the yields are typically in the 2-10 mg/L range ("mid- to low yielders"), particularly about 5 mg/L or less ("low yielders"). Such methods comprise the use of one or more of the compounds encompassed by the present disclosure, e.g., statins and their structural analogs (including simvastatin) as well as their functional equivalents, and certain GPCR binding agents as described herein. The methods of the present invention are particularly useful for enhancing protein production of low yielders.

BRIEF DESCRIPTION OF THE FIGURES

FIG. 5A shows total particles compared to HA yield for 1 μM sulphonamide or 0.05 μM pitavastatin. FIG. 5B shows comparison of total particles to HA yield increase using 0.05 μM pitavastatin.

FIG. 6A, FIG. 6B, and FIG. 6C show a linear plot indicating compound traceability using mass spec for detection of pitavastatin and sulphonamide. The assay has a limit of detection from pure solvent (50% acetonitrile) of approximately 0.5 ng/ml.

FIG. 9A illustrates a schematic of the mevalonate pathway; and FIG. 9B blocking all three arms of the mevalonate pathway with specific enzyme inhibitor combinations can mimic the effect of a statin on protein yield in host cells.

FIG. 18A: protein yield of BFY589-treated vs, untreated cells, in which each data point represents a target protein tested; FIG. 18B: protein expression in fold-increase as a function of control yield (untreated), in which each data point represents a target protein tested.

DETAILED DESCRIPTION OF THE INVENTION

Figure 1:
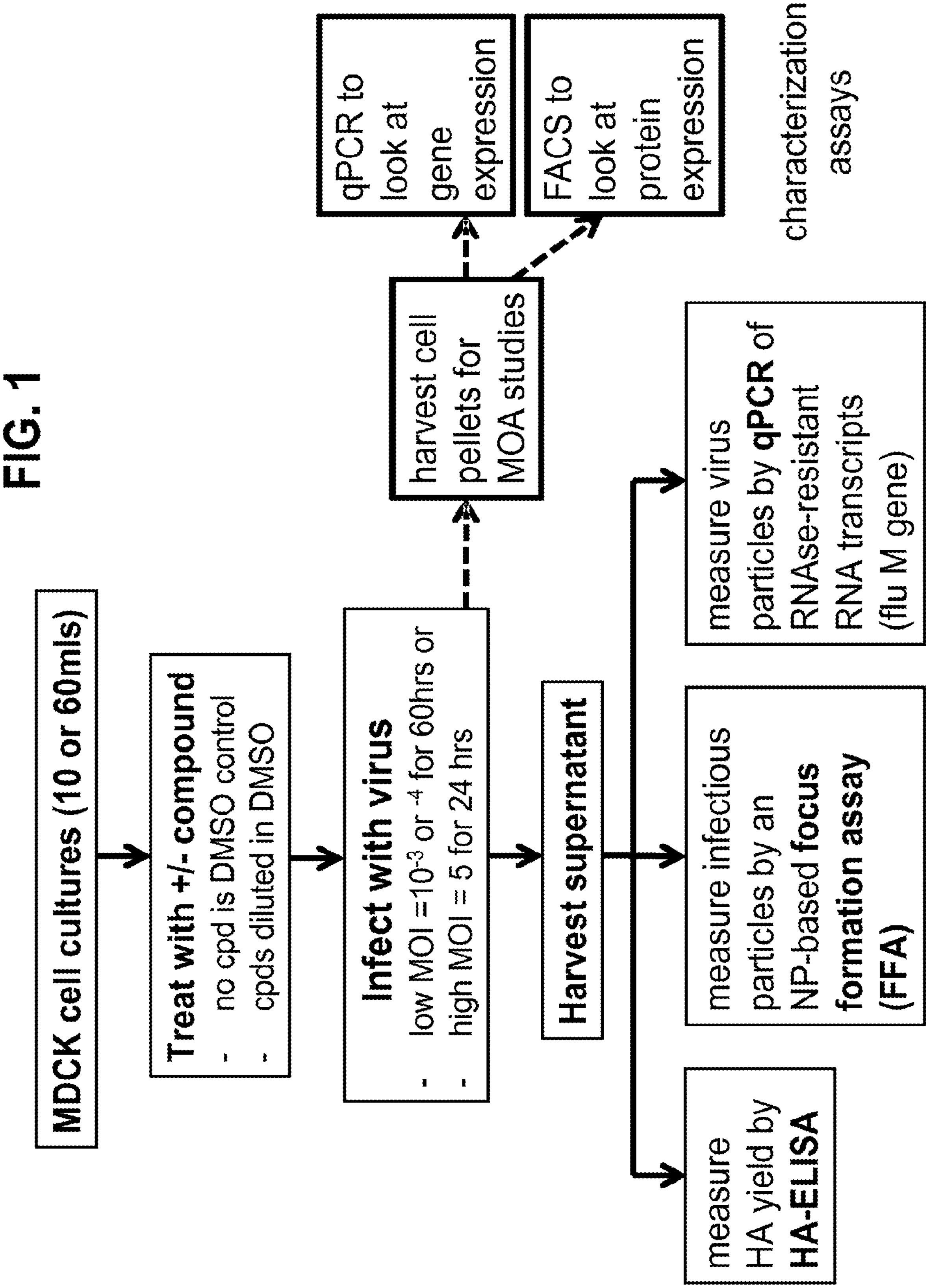
FIG. 1 shows a process flow diagram for identification of chemical agents which improve HA yield

The inventors have identified methods which facilitate increased production or expression of biological products from host cell systems. Production is significantly improved using low concentrations of at least one chemical agent encompassed herein as compared with biological molecules produced from corresponding control cells treated with suitable vehicle, such as DMSO, under otherwise equivalent conditions.

Accordingly, in some embodiments, the increase in yield of biological molecules from host cell systems is at least 2-fold compared to corresponding control. The yield in biological molecules produced in the presence of chemical agents used in the invention may vary according to the individual characteristics of a particular host cell, virus, protein, chemical agent, determination of what constitutes desired cellular activity or other user defined parameters commonly used in a given experiment analysis. In some embodiments, the production yield of a biological product of interest is increased at least by 20%, e.g., at least by 25%, 30%, 35%, 40%, 45%, 50%, 55%, 60%, 65%, 70%, 75%, 80%, 85%, 90%, 95%, 100%, 125%, 150%, 175%, 200%, 225%, 250%, 275%, 300%, 350%, 400%, 450%, and 500%, as compared to control (i.e., grown without the compound but otherwise in equivalent conditions).

Suitable concentrations of chemical agents used in the invention may be selected from a range of about 0.1 nM-10 μM. Suitable concentrations of the compound used to carry out the invention refer to concentrations effective to increase production yield, as compared to control. Suitable concentrations may range, for example, between 0.1-5000 nM, e.g., 0.5-1000 nM, 0.5-500 nM, 0.5-250 nM, 0.5-200 nM, 0.5-150 nM, 0.5-100 nM, 0.5-75 nM, 0.5-50 nM, 0.5-25 nM, 0.5-20 nM, 0.5-15 nM, 0.5-10 nM, 0.5-5 nM, 1-100 nM, 1-75 nM, 1-50 nM, 1-25 nM, 1-20 nM, 1-15 nM, 1-10 nM, 2-50 nM, 2-40 nM, 2-20 nM, 2-10 nM, etc. In some embodiments, effective concentrations are ≤50 nM, e.g., ≤40 nM, ≤30 nM, ≤25 nM, ≤20 nM, ≤15 nM, ≤14 nM, ≤13 nM, ≤12 nM, ≤11 nM, ≤10 nM, ≤9 nM, ≤8 nM, ≤7 nM, ≤6 nM, ≤5 nM. By way of example, the chemical agents used in the invention may be present in a final concentration of 0.001 μM-0.5 μM, preferably about 0.01 μM, 0.02 μM, 0.03 μM, 0.04 μM, 0.05 μM, 0.06 μM, 0.07 μM, 0.08 μM, 0.09 μM, or 0.10 μM. Preferably the chemical agent is in contact with a host cell at the lowest concentration that can achieve at least a 20% increase in product yield. More preferably, the chemical agent is in contact with a host cell at the lowest concentration that can achieve at least a two-fold increase in product yield.

The concentration of a chemical agent will also depend on the specific agent, system or conditions that can produce the results described by the invention and remains nontoxic to the host cell, virus, or biological product. Optimal concentrations that achieve the results of the invention can be adjusted using routine methods. For example, experimental conditions can be tailored to achieve suitable conditions and results for production scale.

Certain chemical agents described herein may be characterized by their physical, chemical and pharmacological qualities. These agents may be chemically manipulated to provide an agent at an optimal concentration to increase the yield of biological products in host cell systems, particularly cell cultures and eggs.

In one aspect, the effect or activity of certain chemical agents that are in contact with host cells can be enhanced if the lipophilicity of the agent is increased. Chemical and structural modifications of the agents may enhance cell membrane transport or protein expression. In a particular aspect chemical agents can be chemically modified to produce pro-drug analogs. Standard techniques involved in making and using pro-drugs are suitably applicable to the chemical agents used in the present invention. See The Practice of Medicinal Chemistry, Ch. 31-32 (Ed. Wermuth, Academic Press, San Diego, Calif., 2001).

Exemplary prodrugs of the agents used in the invention are commercially available pharmaceutical substances already known to exhibit in vivo physiological action, such as hydrolysis, metabolism and the like, following administration of the prodrug to a subject. Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity. Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols). As used in the present invention, the chemical agents are modified to facilitate the productivity of host cell systems for expressing biological products in vitro.

The invention thus encompasses chemical agents in the form of conventional pharmaceutically acceptable acids, for example maleic, hydrochloric, hydrobromic, phosphoric, acetic, fumaric, salicylic, citric, lactic, mandelic, tartaric and methanesulfonic. Chemical agents may also form solvates such as hydrates, and the invention also extends to these forms.

It will be noted that the structure of some of the chemical agents used in the invention may possess one or more stereocenters and each center may exist in the R or S configuration, or combinations thereof. Likewise, the compounds presented herein may possess one or more double bonds and each may exist in the E (trans) or Z (cis) configuration, or combinations thereof. Presentation of one particular stereoisomer, regioisomer, diastereomer, enantiomer or epimer should be understood to include all possible stereoisomers, regioisomers, diastereomers, enantiomers or epimers and mixtures thereof. Thus, the compounds presented herein include all separate configurational stereoisomeric, regioisomeric, diastereomeric, enantiomeric, and epimeric forms as well as the corresponding mixtures thereof. Presentation of one particular chemical structure or chemical name for a compound which contains one or more chiral centers, but which does not designate a particular stereochemistry, should be understood to include all possible stereoisomers, including mixtures of all possible stereoisomers, pure forms or substantially pure forms of one particular stereoisomer and pure forms or substantially pure forms of the alternate stereoisomer. Techniques for inverting or leaving unchanged a particular stereocenter, and those for resolving mixtures of stereoisomers are well known in the art and it is well within the ability of one of skill in the art to choose an appropriate method for a particular situation. See, for example, Furniss et al. (eds.), VOGEL'S ENCYCLOPEDIA OF PRACTICAL ORGANIC CHEMISTRY 5th ED., Longman Scientific and Technical Ltd., Essex, 1991, 809-816; and Heller, Acc. Chem. Res. 1990, 23, 128.

Any asymmetric atom (e.g., carbon or the like) of the agent(s) used in the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form. The chemical agents encompassed herein may be present in a racemic mixture containing both the R- or S-form or alternatively enantiomerically enriched in either the R- or S-form and/or depending on the desired level of functional activity in each enantiomer.

Any resulting mixtures of isomers can be separated on the basis of the physicochemical differences of the constituents, into the pure or substantially pure geometric or optical isomers, diastereomers, racemates, for example, by chromatography and/or fractional crystallization.

Chemical agents used in the present invention can be designed or modeled by common chemical analysis. For example, the skilled person may modify constituents and side groups of a compound into a conformational analog employing structure-activity relationships (SAR). SAR aims to provide enough of each active compound for further profiling of biological activity. Structures may be determined primarily on the basis of mass spectrometry and nuclear magnetic resonance data.

Isolation and purification of chemical agents, intermediates and analogs is achieved, if desired, by any suitable separation or purification procedure such as, for example, filtration, extraction, crystallization, column chromatography, thin-layer chromatography, thin-layer chromatography, centrifugal chromatography, HPLC, or a combination of these procedures. Specific illustrations of suitable synthesis and isolation procedures can be found in patents described herein which are incorporated by reference in their entirety.

A concern in adding synthetic compounds to a manufacturing process is the potential for toxicity from degradation products such as metabolites. Degradation products can be metabolites of a compound produced as a result of its biotransformation in a host cell, e.g. biotransformation to a more polar molecule such as by oxidation, reduction. The degradation product may differ from the original compound in such ways as molecular weight, degree of solubility, and molecular structure or composition. As degradation products are subjected to manufacturing processes, it is possible that these degradation products may become concentrated to unacceptable levels which are particularly problematic in downstream processes.

Assays for clearance of a chemical agent, metabolite, or analogs thereof may be accomplished essentially as described herein. Assays for quantitation or identification of a metabolite are known to one of skill in the art in light using standard analytical methods including, HPLC, TLC, electrochemical analysis, mass spectroscopy, refractive index spectroscopy, ultraviolet spectroscopy, fluorescent analysis, radiochemical analysis, near infrared spectroscopy, nuclear magnetic resonance spectroscopy, light scattering analysis and other methods known in the art.

In one aspect, the chemical agents used in the present invention are not substantially metabolized or degraded during processing, purification or concentration of influenza HA antigens. Trace amounts of unmetabolized compounds may remain after influenza virus purification as measured by mass spec, typically less than 0.25% of the original input amount remains after the purification process.

Levels of metabolite present in a medium or product should not exceed, e.g., greater than about 1%, 2%, greater than about 3%, greater than about 4%, greater than about 5%, greater than about 10%, greater than about 20%, greater than about 30%, greater than about 40%, greater than about 50% of at least one tested activity of the parent compound or input amount of the chemical agent selected.

In one aspect, chemical agents are not detected in a purified sample. The chemical agents can be traced as illustrated herein at a limit of detection (LOD) of about 0.5 ng/ml pure solvent (50% acetonitrile) Preferably, any chemical agents that may be present in a purified sample are detected at 0.5 ng/ml or less in the cell culture supernatant, more preferably in a purified sample such as a final product which is a monobulk comprising monovalent bulks of influenza virus or antigen.

Statin Analogs

The use of Simvastatin as a growth enhancer has been pre-described (see above). However, the inventors have discovered that several other statin compounds facilitate increased yield of biological molecules produced in host cell systems. These statin agents can effect at least a 2-fold yield at low statin concentrations. In a particular aspect, the chemical agents described in the invention have surprisingly broad application to many influenza subtypes and strains at particularly low concentrations.

The principles of the invention are generally applicable broadly to many statins but preferably excluding simvastatin. The meaning and definition of a 3-hydroxy-3-methylglutaryl-Coenzyme-A reductase inhibitor ("HMG-CoA inhibitor") in this invention refers to any selective, competitive inhibitor of HMG-CoA reductase, the rate-limiting enzyme that converts HMG-CoA into mevalonate, generally referred to as cholesterol-lowering statins.

Statins share a characteristic structure, consisting of a heptenoic or heptanoic acid moiety (free acid, salt or lactone) connected to an aromatic or alicyclic core. Biological activity of statins is closely related to their stereochemistry, especially configuration at the chiral atoms of said heptenoic or heptanoic acid moiety. Statins and analogs thereof are available commercially and widely used to inhibit the conversion of mevalonate by HMG-CoA reductase to cholesterols. Assays for determining whether statins act through this biological pathway are disclosed in U.S. Pat. No. 4,231,938.

Statins can be divided into two groups: fermentation-derived and synthetic. Naturally occurring statins are derivatives of fungi metabolites (ML-236B/compactin/monocalin K) isolated from *Pythium ultimum, Monacus ruber, Penicillium citrinum, Penicillium brevicompactum* and *Aspergillus terreus*, though as shown they can be prepared synthetically as well. By way of example, a statin may be selected from atorvastatin, mevastatin (or compactin), fluindostatin, velostatin, fluvastatin, dalvastatin, cerivastatin, pentostatin, rosuvastatin, lovastatin (such as Mevinolin), pitavastatin, simvastatin, or analogs thereof.

Statin derivatives are well known in the literature and can be prepared by methods disclosed in The Peptides: Vol. 5, Analysis, Synthesis, Biology: Academic Press NY (1983); and U.S. Pat. No. 4,397,786. A variety of statin analogs that increase expression and yield of biological molecules and products, particularly influenza virus products produced from cultured cells and eggs.

Any of these statins and analogs thereof can be used in the present invention.

Formula 1—Fluvastatin and Related Analogs

In one preferred aspect, the invention relates to use of a chemical agent of Formula 1 for the manufacture of biologic products, in particular flu vaccines, in host cell systems such as cell culture or in eggs. Formula 1 comprises a statin having the structure:

Formula 1

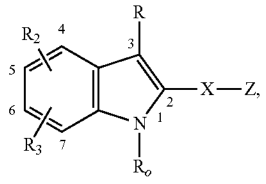

wherein one of R and $R_o$ is

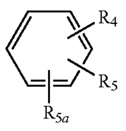

and the other is primary or secondary $C_{1-6}$ alkyl not containing an asymmetric carbon atom, $C_{3-6}$ cycloalkyl or phenyl-$(CH_2)_m$—, wherein $R_4$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy, $R_5$ is hydrogen, $C_{1-3}$alkyl, $C_{1-3}$alkoxy, trifluoromethyl, fluoro, chloro, phenoxy or benzyloxy, $R_{5a}$ is hydrogen, $C_{1-2}$alkyl, $C_{1-2}$alkoxy, fluoro or chloro, and m is 1, 2 or 3, with the provisos that both $R_5$ and $R_{5a}$ must be hydrogen when $R_4$ is hydrogen, $R_{5a}$ must be hydrogen when $R_5$ is hydrogen, not more than one of $R_4$ and $R_5$ is trifluoromethyl, not more than one of $R_4$ and $R_5$ is phenoxy, and not more than one of $R_4$ and $R_5$ is benzyloxy, $R_2$ is hydrogen, $C_{1-3}$alkyl, n-butyl, i-butyl, t-butyl, $C_{3-6}$ cycloalkyl, $C_{1-3}$ alkoxy, n-butoxy, i-butoxy, trifluoromethyl, fluoro, chloro, phenoxy or benzyloxy, $R_3$ is hydrogen, $C_{1-3}$alkyl, $C_{1-3}$alkoxy, trifluoromethyl, fluoro, chloro, phenoxy or benzyloxy, with the provisos that $R_3$ must be hydrogen when $R_2$ is hydrogen, not more than one of $R_2$ and $R_3$ is trifluoromethyl, not more than one of $R_2$ and $R_3$ is phenoxy, and not more than one of $R_2$ and $R_3$ is benzyloxy, X is $—(CH_2)_n—$ or $—CH{=}CH—$, wherein n is 0, 1, 2 or 3, and Z is

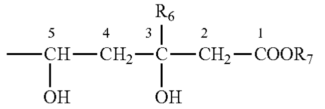

or

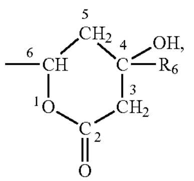

wherein $R_6$ is hydrogen or $C_{1-3}$alkyl, and $R_7$ is hydrogen, $C_{1-3}$alkyl, n-butyl, i-butyl, t-butyl, benzyl or M, wherein M is a pharmaceutically acceptable cation.

Fluvastatin sodium, marketed under the name LESCOL, by Novartis Pharmaceuticals, can be prepared as described in U.S. Pat. No. 5,354,772. In a particular preferred embodiment, a statin analog of Formula 1 is fluvastatin ($C_{24}H_{26}FNO_4$ or (3R, 5S, 6E)-7-[3-(4-fluorophenyl)-1-(propan-2-yl)-1H-indol-2-yl]-3, 4-dihydroxyhept-6-enoic acid) having the structure:

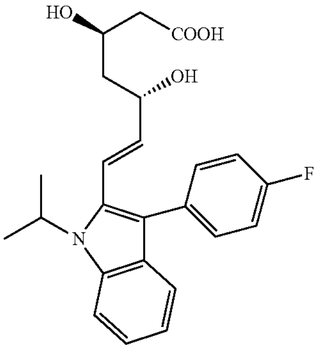 [SMILES: CC(C)n1c(/C=C/[C@@H](O)C[C@@H](O)CC(=O)O)c(-c2ccc(F)cc2)c2ccccc21]

Increased cellular activity may be obtained by a final concentration of fluvastatin or analogs thereof in the range of 0.001 μM-10 μM. In certain preferred though non-limiting aspect, the optimal final concentration of fluvastatin is 0.05 μM or less.

Formula 2—Pitavastatin and Related Analogs

In another preferred aspect the invention relates to use of a chemical agent of Formula 2 for the manufacture of biologic products, in particular flu vaccines, in host cell systems such as cell culture or eggs. Preferably Formula 2 comprises statins having the structure:

Formula 2

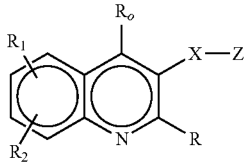

wherein each of R and $R_o$ is, independently $C_{1-6}$ alkyl (primary, secondary or tertiary), $C_{3-7}$ cycloalkyl or ring A

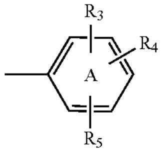

each of $R_1$, $R_2$, $R_3$, $R_4$ and $R_5$ is, independently hydrogen, $C_{1-4}$ alkyl, $C_{1-4}$ alkoxy, trifluoromethyl, fluoro, chloro, phenoxy, benzyloxy or hydroxy; with the provisos that not more than one of $R_1$ and $R_2$ is trifluoromethyl, not more than one of $R_1$ and $R_2$ is phenoxy, not more than one of $R_1$ and $R_2$ is benzyloxy, not more than one of $R_1$ and $R_2$ is hydroxy, not more than one of $R_3$-$R_5$ is the trifluoromethyl, not more than one of $R_3$-$R_5$ is hydroxyl:

X is $-(CH_2)_2-$ or —CH≡CH— (cis and/or trans):

Z is

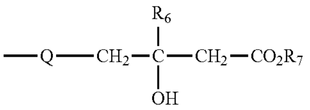 or 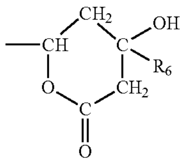

wherein Q is

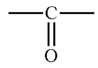 or 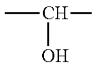

with the proviso that Q may be

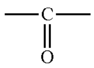

only when X is —CH═CH and/or $R_6$ is $C_{1-3}$ alkyl; $R_6$ is hydrogen or $C_{1-3}$ alkyl;

$R_7$ is hydrogen, $R_8$ or M; $R_8$ is a physiologically acceptable and hydrolyzable ester group; and M is a pharmaceutically acceptable cation.

Pitavastatin calcium, marketed under the name LIVALO, by Kowa Co, can be prepared as described, among other places, in U.S. Pat. No. 5,753,675. In a particular preferred embodiment, Pitavasatin is used (depicted as Compound G in Table 4), which is a statin analog of Formula 2 ($C_{25}H_{24}FNO_4$ or (3R, 5S, 6E)-7-[2-cyclopropyl-4-(4-fluorophenyl)-quinolin-3-yl)-3, 5-dihydroxyhept-6-enoic acid) having the structure:

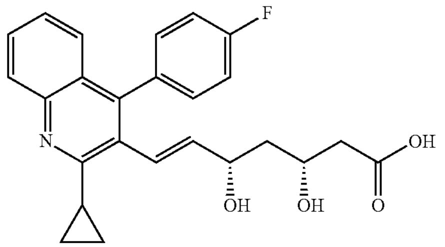 [SMILES: O=C(O)C[C@H](O)C[C@H](O)/C=C/c1c(C2CC2)nc2ccccc2c1-c1ccc(F)cc1]

Increased cellular activity is obtained with a final concentration of derivatives of Formula 2 in the range of 0.001-10 μM. In certain preferred though nonlimiting embodiments, an optimal final concentration of pitavastatin is 0.05 μM or less. As exemplified further herein, unexpectedly, a pitavastatin compound was found to be more effective in increasing protein production yield at 5 nM than at 50 nM, which in turn was more effective than at 500 nM. This is particularly advantageous for the manufacture of therapeutic compositions for human use.

However, the invention is not restricted solely to pitavastatin or fluvastatin agents. Analogs of Formula 1 and 2 have been tested and produce the surprising effects encompassed by the present invention. These analogs were tested as described further below.

Formula 3—Atorvastatin and Related Analogs

In one aspect, the invention relates to use of a chemical agent of Formula 3 for the manufacture of biologic products, in particular flu vaccines, in host cell systems such as cell culture or in eggs. Preferably Formula 3 comprises a statin analog having the structure:

Formula 3

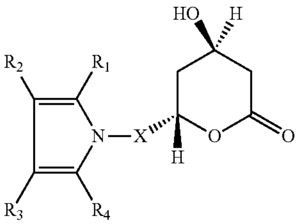

wherein X is —$CH_2$—, —$CH_2CH_2$—, —$CH_2CH_2CH_2$— or —$CH_2CH(CH_3)$—.

$R_1$ is 1-naphthyl; 2-naphthyl; cyclohexyl; norbornenyl; 2-, 3-, or 4-pyridinyl; phenyl, phenyl substituted with fluorine, chlorine, bromine, hydroxyl; trifluoromethyl; alkyl of from one to four carbon atoms, alkoxy of from one to four carbon atoms, or alkanoyloxy of from two to eight carbon atoms. Either $R_2$ or $R_3$ is —$CONR_5R_6$ where $R_5$ and $R_6$ are independently hydrogen; alkyl of from one to six carbon atoms; 2-, 3-, or 4-pyridinyl; phenyl; phenyl substituted with fluorine, chlorine, bromine, cyano, trifluoromethyl, or carboalkoxy of from three to eight carbon atoms; and the other of $R_2$ or $R_3$ is hydrogen; alkyl of from one to six carbon atoms; cyclopropyl; cyclobutyl; cyclopentyl; cyclohexyl; phenyl; or phenyl substituted with fluorine, chlorine, bromine, hydroxyl; trifluoromethyl; alkyl of from one to four carbon atoms, alkoxy of from one to four carbon atoms, or alkanoyloxy of from two to eight carbon atoms. $R_4$ is alkyl of from one to six carbon atoms; cyclopropyl; cyclobutyl; cyclopentyl; cyclohexyl; or trifluoromethyl.

Atorvastatin calcium, marketed under the name LIPITOR by Pfizer, is prepared as and described, among other places, in U.S. Pat. No. 5,273,995. In a particular preferred embodiment, a statin analog of Formula 3 is atorvastatin ($C_{33}H_{34}FN_2O_5$; [R—(R*, R*)]-2-(4-fluorophenyl)-β, δ-dihydroxy-5-(1-methylethyl)-3-phenyl-4-[(phenylamino)carbonyl]-1Hpyrrole-1-heptanoic acid, calcium salt (2:1) trihydrate) having the structure:

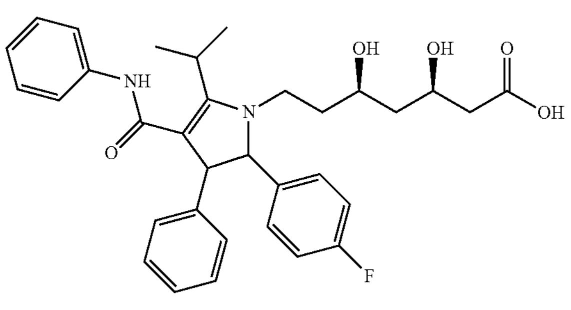 [SMILES: CC(C)C1=C(C(=O)Nc2ccccc2)C(c2ccccc2)C(c2ccc(F)cc2)N1CC[C@@H](O)C[C@@H](O)CC(=O)O]

Formula 4—Cerivastatin and Related Compounds

In another aspect, the invention relates to use of a chemical agent of Formula 4 for the manufacture of biologic products, in particular flu vaccines, in cell culture or in eggs. Preferably Formula 4 comprises a statin analog having the structure:

Formula 4

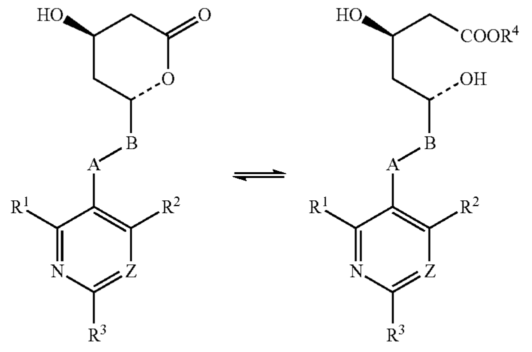

I II wherein A-B denotes a radical of the formula —CH═CH— or —$CH_2$—$CH_2$—, Z denotes a radical of the formula —CH or a nitrogen atom, $R_1$, $R_2$ and $R_3$, independently of one another, denote hydrogen, a saturated or unsaturated, straight-chain or branched hydrocarbon radical which has up to 6 carbon atoms and can optionally be substituted on the terminal carbon by a saturated or unsaturated, cyclic hydrocarbon radical having 3-6 carbon atoms, a cyclic hydrocarbon radical which has 3-7 carbon atoms and is saturated or is unsaturated once or twice, an aromatic radical selected from the group comprising phenyl, furyl, thienyl or pyridinyl, which can optionally carry in the nucleus 1-3 identical or different substituents from the following groups: halogen, trifluoromethyl, alkyl or alkenyl, each having up to 6 carbon atoms, hydroxyl, alkoxy having 1-6 carbon atoms, carboxyl, or carbalkoxy having 1-6 carbon atoms in the alkoxy moiety, $R_4$ denotes hydrogen, a straight-chain or branched, saturated or unsaturated hydrocarbon radical having up to 5 carbon atoms, a benzyl radical whose nucleus can be substituted 1-2 times by halogen or an alkyl radical having 1-4 carbon atoms, an alkali metal or an ammonium ion $NR_5R_6R_7R_8$, where $R_5$, $R_6$, $R_7$ and $R_8$ are identical or different and denote hydrogen, alkyl having 1-4 carbon atoms or hydroxyalkyl having 1-4 carbon atoms.

Cerivastatin sodium, marketed under the name BAYCOL, by Bayer, can be prepared as described, among other places, in U.S. Pat. No. 5,177,080. In a particular preferred embodiment, a statin analog of Formula 4 is cerivastatin ([S—[R*, S*-(E)]]-7-[4-(4-fluorophenyl)-5-methoxymethyl)-2,6bis (1-methylethyl)-3-pyridinyl]-3,5-dihydroxy-6-heptenoate; $C_{26}H_{33}FNO_5Na$) having the structure:

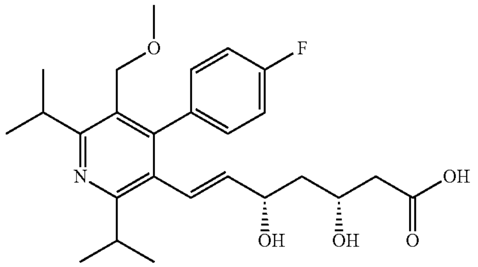 [SMILES: COCc1c(C(C)C)nc(C(C)C)c(/C=C/[C@@H](O)C[C@@H](O)CC(=O)O)c1-c1ccc(F)cc1]

Formula 5—Lovastatin/Mevastatin and Related Compounds

In another aspect, the invention relates to use of a chemical agent of Formula 5 for the manufacture of biologic products, in particular flu vaccines, in cell culture or in eggs. Preferably Formula 5 comprises a statin analog having the structure:

Formula 5

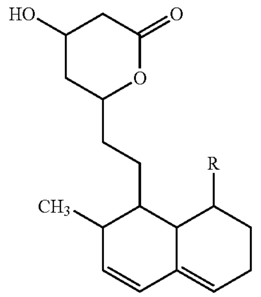

wherein R is hydrogen atom, hydroxy group or 2-methylbutyryloxy group (—$OCOCH(CH_3)CH_2CH_3$).

Lovastatin, marketed under the trademark MEVACOR by Merck, can be prepared as described, among other places, in U.S. Pat. No. 4,231,938. In a particular preferred embodiment, a statin analog of Formula 5 is lovastatin ([1S-[1α(R*),3α,7α,8α(2S*,4S*), 8aα]]-1,2,3,7, 8,8a-hexahydro-3, 7-dimethyl-8-[2-(tetrahydro-4-hydroxy-6-oxo-2H-pyran-2-yl)ethyl]-1-naphthalenyl 2-methylbutanoate; $C_{24}H_{36}O_5$) having the structure:

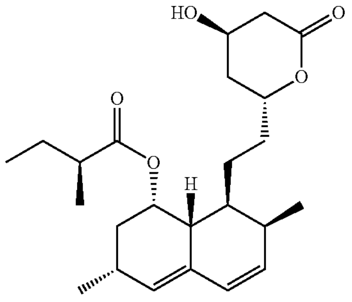 [SMILES: CC[C@H](C)C(=O)O[C@H]1C[C@@H](C)C=C2C=C[C@H](C)[C@H](CC[C@@H]3C[C@@H](O)CC(=O)O3)[C@H]21]

In another particular preferred embodiment, a statin analog of Formula 5 is mevastatin (1S, 7R, 8S, 8aR)-8-{2-[(2R, 4R)-4-hydroxy-6-oxotetrahydro-2H-pyran-2-yl]ethyl}-7-methyl-1,2,3,7,8,8a-hexahydronaphthalen-1-yl(2S)-2-methylbutanoate; $C_{23}H_{34}O_6$) having the structure:

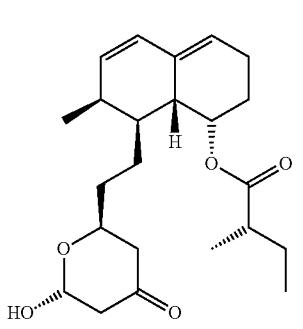

In certain embodiments of the invention, simvastatin, which is an analog of Formula 5 is not used.

Formula 6—Pravastatin and Related Compounds

In another aspect, the invention relates to use of a chemical agent of Formula 6 for the manufacture of biologic products, in particular flu vaccines, in cell culture or in eggs. Preferably Formula 6 comprises a statin analog having the structure:

Formula 6

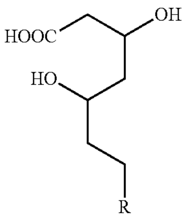

wherein R represents a group of structures:

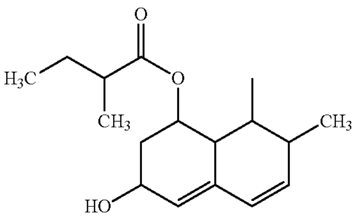

or

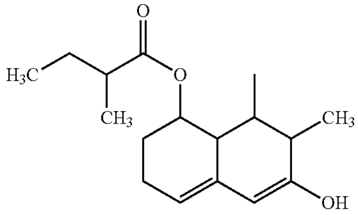

)

and ring-closed lactones, salts and esters thereof.

Pravastatin sodium, marketed under the trademark PRAVACHOL by Bristol-Myers-Squibb, can be prepared as described, among other places, in U.S. Pat. No. 4,346,227. In a particular preferred embodiment, a statin analog of Formula 6 is pravastatin (1-Naphthalene-heptanoic acid, 1,2,6,7,8,8ahexahydro-β,δ,6-trihydroxy-2-methyl-8-(2-methyl-1-oxobutoxy)-, monosodium salt, [1S[1α(βS*,δS*), 2α,6α,8β(R*),8aα]; $C_{23}H_{35}NaO_7$] having the structure:

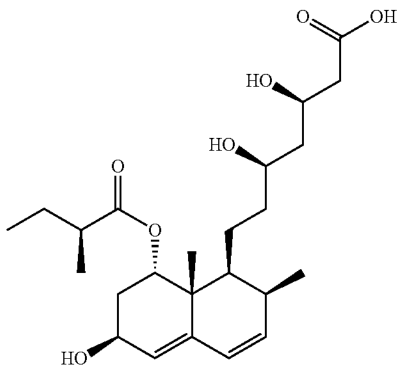 [SMILES: CC[C@H](C)C(=O)O[C@H]1C[C@H](O)C=C2C=C[C@H](C)[C@H](CC[C@@H](O)C[C@@H](O)CC(=O)O)[C@]21C]

Formula 7—Rosuvasatin and Related Compounds

In another aspect, the invention relates to use of a chemical agent of Formula 7 for the manufacture of biologic products, in particular flu vaccines, in cell culture or in eggs. Preferably Formula 7 comprises a statin analog having the structure:

Formula 7

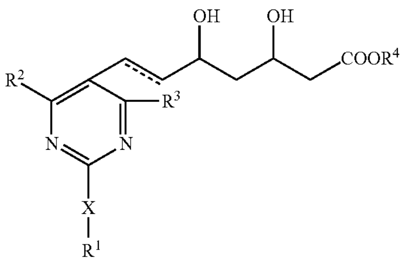

wherein $R_1$ is lower alkyl, aryl, or aralkyl, each of which may have one or more substituents; $R_2$ and $R_3$ each is independently hydrogen, lower alkyl, or aryl, and each of said lower alkyl and aryl may have one or more substituents; $R_4$ is hydrogen, lower alkyl, or a cation capable of forming a non-toxic pharmaceutically acceptable salt; X is sulfur, oxygen, or sulfonyl, or imino which may have a substituent; the dotted line represents the presence or absence of a double bond, or the corresponding ring-closed lactone.

Rosuvastatin sodium, marketed under the trademark CRESTOR by AstraZeneca, can be prepared as described, among other places, in U.S. Pat. No. 4,346,227. In a particular preferred embodiment, a statin analog of Formula 7 is rosuvastatin bis[(E)-7-[4-(4-fluorophenyl)-6-isopropyl-2-[methyl(methylsulfonyl)amino] pyrimidin-5-yl](3R,5S)-3,5-dihydroxyhept-6-enoic acid]; $C_{22}H_{27}FN_3O_6S)_2$] having the structure shown below.

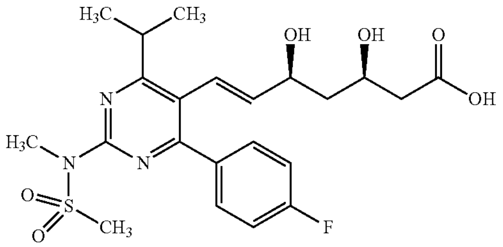 [SMILES: CC(C)c1nc(N(C)S(C)(=O)=O)nc(-c2ccc(F)cc2)c1/C=C/[C@@H](O)C[C@@H](O)CC(=O)O]

Figure 9A:
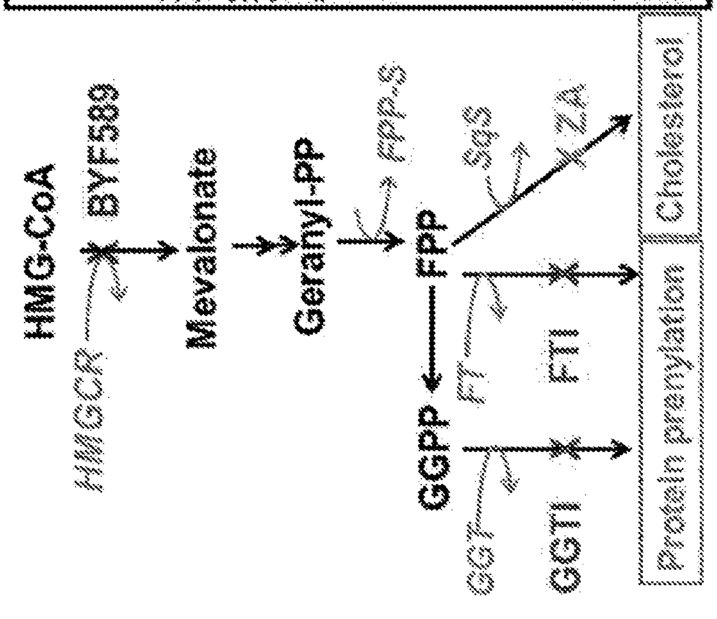
FIG. 9A and FIG. 9B depict the involvement of the mevalonate pathway.
Figure 9B:
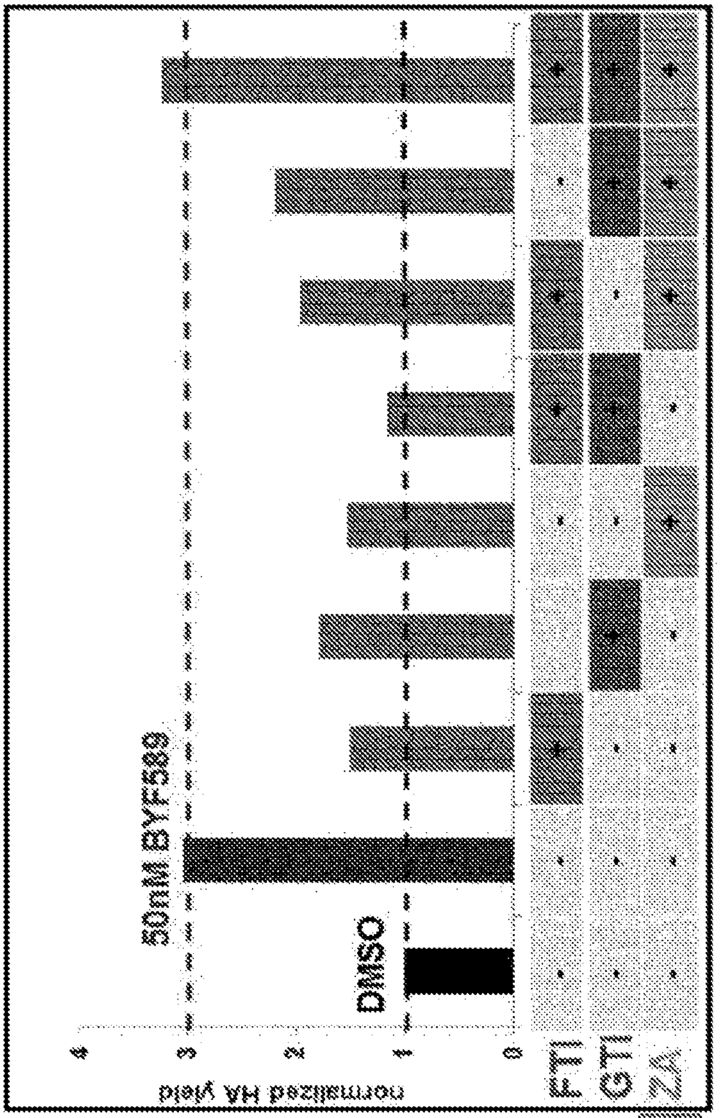

The present invention further encompasses methods for enhancing the production yield of biological products of interest in host cells, comprising inhibiting the mevalonate pathway of the host cell. In some embodiments, the inhibition of the mevalonate pathway involves direct or indirect inhibition of mevalonate itself. Additionally or alternatively, the inhibition of the mevalonate pathway may involve inhibiting the downstream signaling cascade, namely, the pathways that control protein prenylation and cholesterol biosynthesis, respectively. As demonstrated in FIG. 9B, blocking all three arms of the mevalonate pathway with specific enzyme inhibitor combinations can mimic the effect of a statin on protein yield in host cells. Accordingly, in some embodiments, specific inhibitors of the enzymes that catalyze the pathways are employed, such as, squalene synthase inhibitors (e.g., zaragozic acids), farnesyl transferase inhibitors, geranylgeranyl transferase inhibitors, and any combinations thereof. Thus, the invention provides one or more inhibitors of the mevalonate pathway for use in the manufacture of a biologic in a host cell. The invention also provides methods for manufacturing a biologic product comprising the step of inhibiting the mevalonate pathway of a host cell, wherein the inhibition may comprise contacting the host cell with one or more inhibitors of enzymes involved in protein prenylation and cholesterol synthesis. The invention encompasses a biological product produced by any one of such methods.

Non Statin Compounds

Also encompassed by the present invention are non-statin compounds which can be used to increase yield of biological molecules in a host cell. In some embodiments, suitable non-statin compounds for carrying out the present invention are agents that act via serotonin-associated pathway, dopamine-associated pathway, or combination thereof. In some embodiments, suitable compounds are agents that modulate certain G-protein-coupled receptors.

Formula 8—Sulphonamides, Analogs Thereof and Other Inverse Agonists of 5HT7

In one aspect chemical agents useful in the invention include sulphonamide analogs. Sulphonamide analogs have been identified as inverse-agonists of G-protein-coupled-receptors (GPCR), specifically inverse agonists of 5HT7. Accordingly, the present invention also encompasses use of chemical agents which interact with or modulate 5HT7 receptors, in particular inverse agonists of 5HT7. Other agonists of 5HT7 encompassed by the invention include but are not limited to: arylpiperazine- and 1,2,3,4-tetrahydroisoquinoline-based arylsulfonamides (Vermeulen, et al. (2004) Journal of Medicinal Chemistry, 47, 5451-5466), 5-hydroxytryptophan, 8-hydroxy-2-(di-n-propylamino)tetralin 1-Br (8-OH DPAT) and 5-carboxy-aminotryptamine (5-CT) (Siddiqui, et al. (2007) Pharmacology Biochemistry and Behavior, 87, 386-392)

In one aspect, the present invention provides use of a chemical agent of Formula 8 for the manufacture of biologic products, in particular flu vaccines, in cell culture or in eggs. Preferably Formula 8 comprises sulphonamide compounds having the structure:

Formula 8

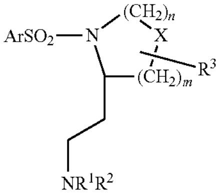

wherein Ar is an optionally substituted mono- or bicyclic aromatic or heteroaromatic ring; $R^1$ and $R^2$ are independently hydrogen, $C_{1-6}$ alkyl, aryl $C_{1-6}$ alkyl or together with the nitrogen atom to which they are attached form an optionally substituted 5- to 7-membered heterocyclic ring optionally containing a further heteroatom selected from nitrogen, sulphur or oxygen, the nitrogen atom being substituted by hydrogen, $C_{1-6}$ alkyl, cyclo $C_{3-7}$ alkyl, or an optionally substituted aryl, heteroaryl or aryl $C_{1-6}$ alkyl group; $R^3$ is hydrogen or $C_{1-6}$ alkyl; X is oxygen, sulphur or a bond; n is 2 or 3; and m is 1 or 2. $C_{1-6}$alkyl groups, whether alone or as part of another group, may be straight chain or branched. Optional substituents for aromatic and heteroaromatic groups include $C_{1-6}$ alkyl optionally substituted by $NR^7R^8$, $C_{2-6}$alkenyl, $C_{2-6}$alkynyl, $C_{1-6}$alkylthio, cyano, nitro, halogen, $CF_3$, $C_2F_5$, $NR_7R_8$, $CONR_7R_8$, $NR_7COR_8$, $S(O)_p NR_7R_8$, CHO, $OCF_3$, $SCF_3$, $COR_9$, $CH_2 OR_9$, $CO_2 R_9$ or $OR_9$ where p is 1 or 2 and $R_7$, $R_8$ and $R_9$ are independently hydrogen, $C_{1-6}$ alkyl, optionally substituted aryl or optionally substituted aryl $C_{1-6}$ alkyl. More than one substituent can be present and in the case of multiple substituents these can be the same or different.

Suitably Ar is an optionally substituted mono- or bicyclic aromatic or heteroaromatic ring. Preferably Ar is an optionally substituted naphthyl, phenyl or thienyl group. Most preferably Ar is naphthyl, phenyl or thienyl substituted by one or more halogen, in particular 2,3-di-bromothienyl. In $R_1$ and $R_2$ optional substituents for the heterocyclic rings include $C_{1-6}$ alkyl. Preferably $R_1$ and $R_2$ form an optionally substituted 5- to 7-membered heterocyclic ring, in particular an optionally substituted 6-membered ring. Most preferably $R_1$ and $R_2$ form a piperidine ring optionally substituted by one or two methyl groups, or $R_1$ and $R_2$ form a piperazine ring substituted on nitrogen with an optionally substituted aryl ring. Preferably $R_3$ is hydrogen.

Preferably X is a bond. Preferably n and m have values such that, together with X, form part of a 5- or 6-membered ring.

A preferred optimal final concentration of Formula 8 is 1.0 μM or less.

A particularly preferred sulphonamide analog of Formula 8 is ($C_{19}H_{30}N_2SO_2$) may be prepared as described in U.S. Pat. No. 6,265,408 and has the structure:

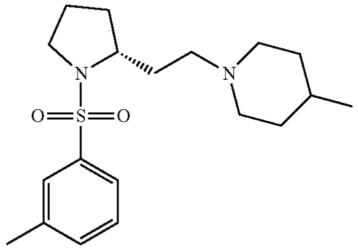

or

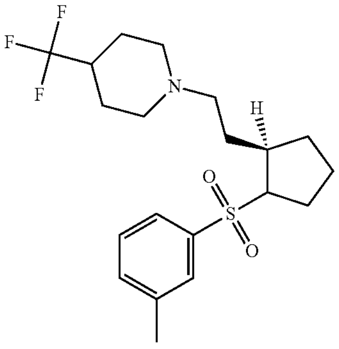

A non-limiting embodiment is depicted as Compound E in Table 4, which is an inverse-agonist of the serotonin 5HT-2 and 5HT-7 receptors. An inverse agonist is an agent that binds to the same receptor as an agonist but induces a pharmacological response opposite to that agonist. Thus, a prerequisite for an inverse agonist response is that the receptor must have a constitutive (also known as intrinsic or basal) level activity in the absence of any ligand. This means that an inverse agonist decreases the activity below the basal level.

It has been known that upon ligand binding the 5HT7 receptor signals through an increase in intracellular cAMP via the adenylyl cyclase (AC) activity. Findings in Example 13 (FIG. 15) suggest that production yield enhancement is dependent on decreasing ligand-mediated activity of the 5HT7 receptor, because the enhancement effects can be abrogated by the presence of serotonin (5HT), which should compete with the inhibitor for binding to the receptor.

Formula 9—Tropanol Esters, Analogs Thereof and Other Inhibitors of Autoreceptors In another preferred aspect, the present invention provides use of a chemical agent of Formula 9 for the manufacture of biologic products, in particular flu vaccines, in cell culture or in eggs. This class of molecules has been identified as inhibitors of presynaptic autoreceptors and act as anticholinergics. Accordingly, the present invention encompasses use of chemical agents which modulate presynaptic autoreceptors and other presynaptic heteroreceptors on the cholinergic synapse including but not limited to: 7-(4-[4-(2,3-dichlorophenyl)-1-piperazinyl]butyloxy)-3,4-dihydro-2(1H)-quinolinone (Kikuchi, et al. (1995) The Journal of Pharmacology and Experimental Therapeutics, 274, 329-336) and (−)-3-(3-hydroxyphenyl)-N-propylpiperidine [(−)-3-PPP] (Thorberg, et al. (1987) Journal of Medicinal Chemistry, 30, 2008-2012). Anticholinergics encompassed by the invention include but are not limited to: neostigmine, glycopyrronium, physostigmine and pyridostigmine. (Nair, et al. (2004) Continuing Education in Anaesthesia, Critical Care & Pain, 4, 164-168)

Preferably Formula 9 comprises tropanyl analogs having the formula:

Formula 9

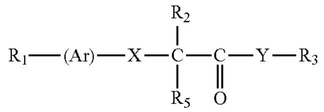

wherein Ar is phenyl or beta-naphtyl, or aromatic heterocyclic 6-membered ring containing one of two nitrogen atoms; $R_1$ is one or more substituents of the Ar nucleus; preferably in para position, and selected from the group consisting of H, $CH_3$, $CH_2$—$CH(CH_3)_2$, O—$CH_3$, Cl, F, Br, $CF_3$, $NH_2$, S—$CH_3$, CN, $NO_2$; $R_2$=H, $CH_3$, $C_2H_5$, $CH(CH_3)_2$; $R_3$ is

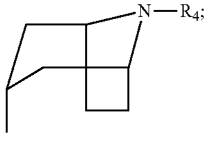

where $R_4$ is H, $CH_3$, $C_2H_5$; $R_5$ is H, $CH_3$; X is none, O, S, NH, $NCH_3$, —CH═CH—, —C≡C—; Y is O, NH.

A preferred tropanyl analog of Formula 9 is ($C_{18}H_{25}NO_2S$) may be prepared as described in, among other places, WO 94/01435, and has the structure:

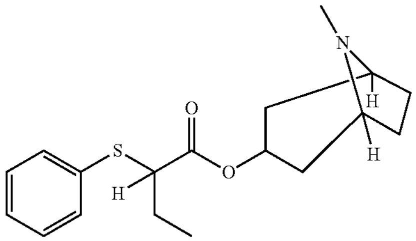

or

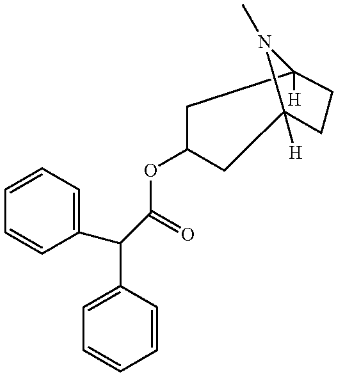

Formula 10—Benziothiazole, Analogs Thereof and Other Dopamine, 5HT2A and 5HT1A Binding Agents In another aspect, the present invention provides use of a chemical agent of Formula 10 for the manufacture of biologic products, in particular flu vaccines, in cell culture or in eggs. This class of molecules has been identified as having neuroleptic activity. Accordingly the present invention encompasses chemical agents which have an affinity for dopamine D2 and serotonin 5HT2A and 5HT1A receptors (Hrib, et al, J. Med. Chem, 22; 37(15):2308-2314 (1994)). Other dopamine, 5HT2A and 5HT1A binding agents encompassed by invention include but are not limited to: clozapine, haloperidol, and hydroxylated dibenzazecines (Hamacher, et al., (2006) BMC Pharmacology, 6, 11)

Preferably Formula 10 comprises benzisothiazole and benzisoxazole analogs having the formula:

Formula 10

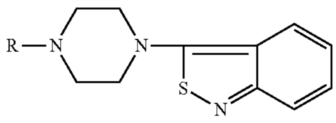

wherein R represents (a)

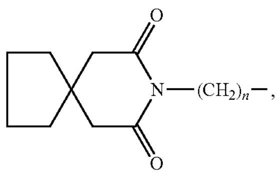

-continued (b)

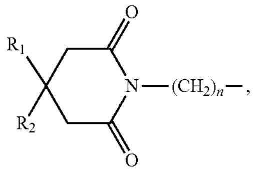

(c)

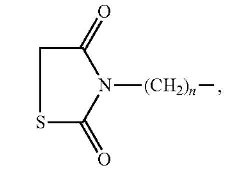

(d)

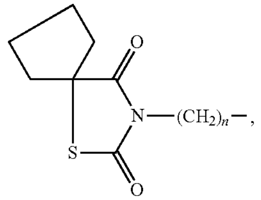

(e)

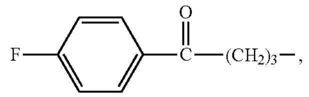

(f)

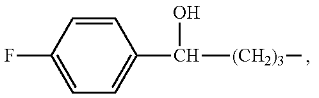

in which n is 3 or 4, $R_1$ and $R_2$ are independently lower alkyl of 1 to 4 carbon atoms, Y is oxygen or sulfur, Z is hydrogen or halogen, or a pharmaceutically acceptable non-toxic acid addition salt thereof.

In one aspect, an analog of Formula 10 is ($C_{24}H_{32}N_4O_2S$) may be prepared as described in, among other places, DE3247530, and has the structure:

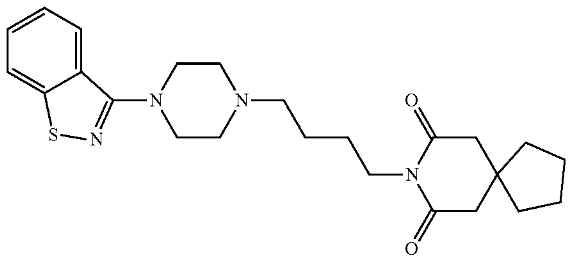 [SMILES: O=C1CC2(CCCC2)CC(=O)N1CCCCN1CCN(c2nsc3ccccc23)CC1]

Formula 11—Benzypyrans, Analogs Thereof and Other Antiarrythmic Agents

In another aspect, the present invention provides use of a chemical agent of Formula 11 for the manufacture of biologic products, in particular flu vaccines, in cell culture or in eggs. This class of molecules has been identified as having antiarrhythmic activity. Accordingly, the present invention encompasses chemical agents which have Class I, Class II, Class III or Class IV antiarrhythmic activity including lidocaine, diphenylhydantoin, quinidine, procainamide, flecainide, beta blockers, verapamil, digitalis, bretylium, ibutilide, sotalol, amiodarone, dofetilide. (Kowey, et al. (2000) American Heart Journal, 140, 12-20)

Preferably Formula 11 comprises benzopyran analogs having the formula:

Formula 11

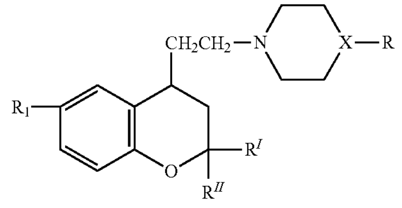

in which $R_1$ is hydrogen, halogen, hydroxy, alkoxy, nitro, amino or alkylsulphonamido, bis(alkylsulphonyl)amino, or acylamino, X denotes a nitrogen atom or a >CH— radical, R is a radical of formula:

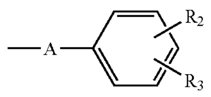

in which A is a single bond, methylene or, when X is a nitrogen atom, carbonyl, and $R_2$ and $R_3$, which are identical or different, are hydrogen, halogen, hydroxy, alkyl, alkoxy, nitro, amino, alkylsulphonamido, bis(alkylsulphonyl)amino, acylamino, sulphamoyl or cyano, or $R_2$ and $R_3$, when they are adjacent, together form a methylenedioxy or ethylenedioxy radical, or R is pyridyl or 2(2H)-benzimidazolonyl if X denotes >CH—, and R' and R", which are identical, are hydrogen or alkyl, and their salts.

An analog of Formula 11 is ($C_{24}H_{31}NO_3$) may be prepared as described in, among other places, EP300908, and has the structure:

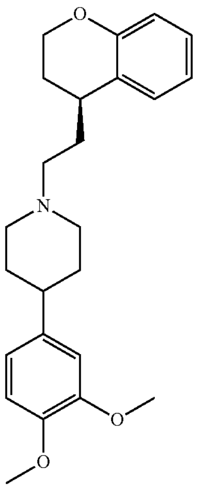 [SMILES: COc1ccc(C2CCN(CC[C@H]3CCOc4ccccc43)CC2)cc1OC]

Formula 12—Tetrahydropyridines, Analogs Thereof and Other Inhibitors of MAO

In another aspect, the present invention provides use of a chemical agent of Formula 12 for the manufacture of biologic products, in particular flu vaccines, in cell culture or in eggs. This class of molecules has been identified to possess therapeutic benefits in the treatment of mental depression. Accordingly, the present invention encompasses use of chemical agents which inhibit monoamine oxidase (MAO) or antagonize the action of tetrabenazine, or target the dopaminergic and serotonergic systems in the brain (Mattson, Doctorates Thesis, Gothenborg University, ISBN: 978-628-8741-4 (2013)). Other MAO inhibitors encompassed by the invention include but are not limited to: oxadiazolone, tetrazole, oxadiazinone, indenopyridazine derivatives, and (1H)-pyrazole derivatives. (Chimenti, et al. (2006) Chemical Biology & Drug Design, 67, 206-214)

Preferably Formula 12 comprises tetrahydropyridine and piperidine analogs having the formula:

Formula 12

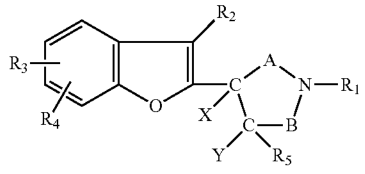

(I)

wherein $R_1$ represent hydrogen, an alkyl group containing 1-4 carbon atoms and which may be substituted by a hydroxyl or oxo radical, an alkenyl or alkynyl group each containing 3 to 4 carbon atoms, a cycloalkylmethyl group containing 4 to 7 carbon atoms, or a benzyl group wherein the phenyl radical may be substituted by at most 3 substituents from the group consisting of alkyl and alkoxy groups each containing 1 to 4 carbon atoms, but $R_1$ must not be a methyl group in the case where A represents an ethylene radical and B represents a methylene radical and at the same time $R_2$, $R_3$, $R_4$ and $R_5$ each represent hydrogen, $R_2$ represent hydrogen or alkyl containing 1 to 4 carbon atoms, $R_3$ represents hydrogen, an alkyl or alkoxy group each containing 1 to 4 carbon atoms, halogen up to atomic number 35 or a hydroxyl group, or $R_3$ and $R_4$ together represent a trimethylene or tetramethylene radical or, corresponding to a fused-on benzene ring, the 1,3-butadienylene radical, $R_5$ represent hydrogen or an alkyl group containing 1-4 carbon atoms, A represent an ethylene or methylene radical or the direct bond, B represent a methylene, ethylene or trimethylene radical, whereby A and B together always contain 3 carbon atoms, and X and Y each represent a hydrogen atom, or together they represent an additional bond and of addition salts thereof with inorganic and organic acids.

An analog of Formula 12 is ($C_{15}H_{19}NO$) may be prepared as described in, among other places, DE2408476, and has the structure:

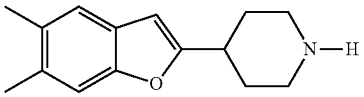 [SMILES: Cc1cc2cc(C3CCNCC3)oc2cc1C]

Formula 13—Dimethoxyphenyl-Piperidinemethanols, Analogs Thereof.

In another aspect, the present invention provides use of a chemical agent of Formula 13 for the manufacture of biologic products, in particular flu vaccines, in cell culture or in eggs. These analogs have been described to act as 5HT2 antagonists and antiarrhythmics. Accordingly, the present invention encompasses chemical agents which have Class I, Class II, Class III or Class IV antiarrhythmic activity including lidocaine, diphenylhydantoin, quinidine, procainamide, flecainide, beta blockers, verapamil, digitalis, bretylium, ibutilide, sotalol, amiodarone, dofetilide (Kowey, et al. (2000) American Heart Journal, 140, 12-20).

Preferably analogs of Formula 13 have the formula:

Formula 13

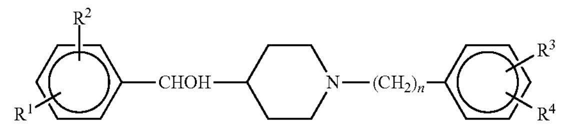

wherein n is 2, 3 or 4 and each R and $R_1$ independently represents hydrogen, $C_{1-6}$ alkyl, halogen, trifluoromethyl, hydroxy, $C_{1-6}$ alkoxy, or amino, R and $R_1$ substituents for $C_{1-6}$ alkyl are methyl, ethyl, propyl, isopropyl, n-butyl, t-butyl, pentyl, hexyl, cyclopropyl, cyclopentyl with methyl and ethyl being preferred. All halogens are embraced with fluoro and chloro being preferred. Representative $C_{1-6}$ alkoxy substituents are methoxy, ethoxy, isopropoxy and such of the aforementioned alkyl groups attached through an oxygen. In those instances wherein R or $R_1$ are other than hydrogen, the substituents may be located at any position, (ortho, meta or para) but para is preferred for monosubstituted phenyl moieties. The 2,3-, 2,4-, 2,5-, 3,4-, or 3,5-disubstituted phenyl moieties are embraced herein.

In one aspect an analog of Formula 13 is an alpha-(2,3-dimethoxyphenyl)-1-[2-(4-fluorophenyl)ethyl]-4-piperidinemethanol ($C_{22}H_{28}NO_3F$) may be prepared as described in, among other places, U.S. Pat. No. 5,134,149, and has the structure:

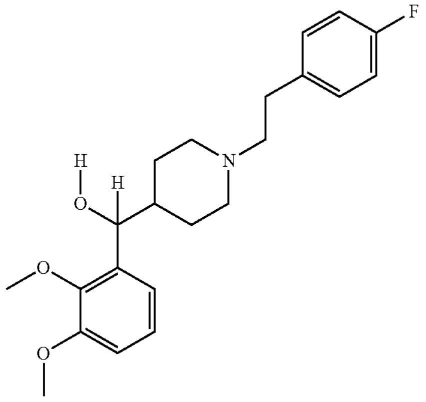 [SMILES: COc1cccc(C(O)C2CCN(CCc3ccc(F)cc3)CC2)c1OC]

The invention includes the use of other agents with similar pharmacological activities in producing biological molecules of interest in a host cell. In some embodiments, such agents include those acting upon the same or overlapping cellular signal transduction pathway(s). Thus, in some embodiments, such agents share the same or overlapping mechanism of action to effectuate certain cellular outcome in the host cell. Such mechanistically equivalent agents may or may not be structurally related to one another.

Accordingly, the invention provides methods for producing a biological product of interest in a host cell, or enhancing yield of such product, comprising contacting the host cell with an agent, so as to enhance protein production in the host cell, wherein the agent is selected from the group consisting of: agents that inhibit 5HT7 receptor signaling, agents that inhibit one or more dopamine receptor signaling, agents that are inverse agonists of one or more histamine receptors, agents that block ion channels (e.g., sodium channels, calcium channels, etc.), agents that inhibit cAMP production, agents that inhibit histamine receptor signaling, and any combinations thereof. The method generally comprises contacting the host cell with the agent; growing or culturing the host cell for a duration of time, at least a portion of which is carried out in the presence of the agent, harvesting the biological product of interest from the host cell, optionally further purifying the biological product, formulating the biological product into a pharmaceutical composition comprising the biological product and optionally a pharmaceutically acceptable carrier and/or excipient, optionally sterile filtering the pharmaceutical composition, packaging the sterile pharmaceutical composition into suitable dosage forms. Pharmaceutical compositions prepared by the methods described herein are encompassed by the present invention.

In some embodiments, the agent inhibits 5HTR signaling wherein the agent can be an inverse agonist of the receptor. In some embodiments, the agent may be an inhibitor of dopamine receptor(s). In some embodiments, the agent can be a dopamine D1 and/or D2 antagonist. Thus, use of an agent that acts as an inverse agonist of 5HT7R for the manufacture of a therapeutic composition comprising a biologic is encompassed by the invention.

Examples of such agents include, without limitation: SB-258719 (a neutral 5HT7R antagonist available from GSK), SB-258741 ("AFZ"; a partial inverse 5HT7R agonist available from GSK), SB-269970 (a robust 5HT7R inverse agonist available from GSK), Risperidone (an antagonist of the D1 and D2 dopamine receptors and an inverse agonist of the 5HT7 serotonin receptors; also an inverse agonist of H1 and H2 histamine receptors), Sertindole (binds to D2, 5-HT2A, 5-HT2C, 5-HT6, 5-HT7, D3, a1); Ziprasidone (binds to D2, 5-HT2A, 5-HT1A, 5-HT1D, 5-HT2C, 5-HT7, D3, a1, NRI, SRI); Loxapine (binds to D2, 5-HT2A, 5-HT6, 5-HT7, D1, D4, a1, M1, H1, NRI); Zotepine (binds to D2, 5-HT2A, 5-HT2C, 5-HT6, 5-HT7, D1, D3, D4, a1, H1, NRI); Clozapine (binds to D2, 5-HT2A, 5-HT1A, 5-HT3, 5-HT6, 5-HT7, D1, D3, D4, a1, a2, M1, H1); Olanzapine (binds to D2, 5-HT2A, 5-HT2C, 5-HT3, 5-HT6, D1, D3, D4, D5, a1, M1-5, H1), Quetiapine (binds to D2, 5-HT2A, 5-HT6, 5-HT7, a1, a2, H1); Promethazine (a strong antagonist of the H1 histamine receptor with weak to moderate affinity for the 5HT2a/c serotonin receptors and dopamine D2 receptor; also a blocker of Na+ channels). Certain ion channel blockers may be also suitable. Examples include, but are not limited to: inhibitors and blockers of voltage-dependent Na+ channels and cholinesterase, involved in lipid transport and metabolism, such as Dibucaine (a butynesterase inhibitor); inhibitors and blockers of voltage-gated L-type calcium channels (such as Nimodipine); inhibitors and blockers of sodium channels such as Aprindine (a Class 1b antiarrhythmic membrane stabilizing agent), Amiloride (a direct blocker of epithelial sodium channel ENaC); and inhibitors and blockers of delayed inward rectifier potassium channels and L-type calcium channels such as Ibutilide hemifumarate (a Class III antiarrhythmic agent).

Treatment of Host Cells

Unless otherwise indicated, the recombinant proteins, cell culture, immunological and microbiological techniques utilized in the present invention are standard procedures, well known to those skilled in the art. Such techniques are described and explained throughout literature in sources such as J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hanes (editors), DNA Cloning: A Practical Approach, Volumes 1-4, IRL Press (1995 and 1996), and F. M. Ausubel et al, (editors), Current Protocols in Molecular Biology, Greene Pub. Associates and Wiley-Interscience (1996), and J. E. Coligan et al., (editors) Current Protocols In Immunology, John Wiley & Sons (including all updates until present), and are incorporated herein by reference.

A feature of the methods of the invention is the effect of improved yield of biological molecules or products produced in host cell systems. The yield of biological molecules as used herein refers to the total amount of recombinantly expressed biological molecules that is recoverable, such as proteins, polypeptides, antibodies (e.g., full length or antigen-binding fragments, engineered counterparts thereof, humanized counterparts thereof, etc.), nucleic acids, virus, enzymes, virus like particles, produced by a host cell, preferably an eukaryotic cell culture, such as plant, avian or mammalian cell culture, generated under conditions suitable for expression, secretion or production. In particular, the biological molecules can be processed further into a desired biological product such as a vaccine.

Increased yield is typically measured in milligrams of protein per milliliter of volume (mg/mL) or grams of protein per liter of volume (g/L).

Increased yield can also be measured as fold increase of biological molecules produced by host cell systems exposed to chemical agents used in the present invention compared to corresponding controls including corresponding host cell systems that are not treated with such chemical agents.

Using the methods of the invention, levels of expressed biological molecules are increased by about 2-fold to up to about 20-fold in excess of what is produced by controls. In preferred embodiments, the increase in yield is at least about 2.5-fold, about 3-fold, about 3.5-fold, about 4-fold, about 4.5-fold, about 5-fold, about 5.5-fold, about 6-fold, about 6.5-fold, bout 7-fold, about 7.5-fold, about 8-fold, about 8.5-fold, about 9-fold, about 9.5-fold, or up to about 10-fold or greater than yield in comparative controls.

In an alternative aspect, any increase in yield may be measured as a percent amount greater than comparative controls. For example, an increase in yield or cellular productivity can comprise a 20%, 30%, 40%, 50%, 60%, 70%, 80%, 90%, 100%, 200%, 300%, 500% or greater increase in any measured parameters compared to control.

As shown in the examples hereinafter, a preferable aspect of the invention is characterized by measuring an increased amount of viral particles (vRNA copies/ml), infectious particles (IU/ml) or virus proteins (μg/ml) produced in culture supernatant. In one type of measurement, an increase in HA or NP protein indicates the ability of a chemical agent to increase the yield of antigenic proteins produced by a host cell system. An increase in cell productivity may also be characterized by measurement of parameters indicating at least 2-fold, 4-fold, 5-fold, 10-fold, 15-fold, 20-fold, 25-fold, 30-fold, 35-fold, 40-fold, 45-fold, 50-fold increase in virus particles, infectious virus particles or virus proteins, preferably HA yield.

Measurement of yield can be conducted during the upstream processing of viral manufacturing for example during viral gene transcription, protein expression or viral particle production or release from a cell culture. Standard methods for detection of biological products in recombinant systems may be used depending on the characteristic of the biological molecule measured. Measurements may indicate productivity and capacity of a host cell system may as accomplished by methods well-known in the art, e.g., measuring changes in morphology and cell surface markers using techniques such as flow cytometry or immunocytochemistry (e.g., staining cells with tissue-specific or cell-marker specific antibodies), by examination of the morphology of cells using light or confocal microscopy, or by measuring changes in gene expression using techniques well known in the art, such as PCR and gene-expression profiling.

In a preferred aspect, viral expression products, preferably influenza virus products, are measured for particle production, infectious particles or antigenic proteins. Influenza virus and antigens can be measured by techniques such as by immunoassays including, but are not limited to, competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays and FACS analysis.

Viral titers may be measured in host cell systems by focus-forming assays and hemagglutination assays. These assay techniques are well known in the art.

The methods of the present invention are intended to be used in host cell systems such as cell cultures or in eggs. In a preferred aspect, cell cultures are treated with at least one chemical agent in a cell culture volume greater than about 200 microliters, such as greater than about 1 milliliter. More preferably, the cell culture volume is from about 1 milliliter to 10000 liters, such as from about 2 milliliters to about 10000 liters. In some embodiments, a batch volume of suitable production is about 15 mL, 50 mL, 75 mL, 100 mL, 150 mL, 200 mL, 250 mL, 500 mL, 1 L, 5 L, 10 L, 15 L, 20 L, 30 L, 40 L, 50 L, 75 L, 100 L, 150 L, 200 L, 350 L, 300 L, 400 L, 500 L, 1,000 L, 2,000 L, 3,000 L, 4,000 L, 5,000 L, or greater.

In a preferred aspect, cells can be grown in culture in the presence of a sufficient amount of a chemical agent under conditions suitable for replication and assembly of viruses or expression of biological products. In some aspects, cells can be cultured at a temperature below about 37° C., preferably at a temperature equal to, or less than, about 35° C. Typically, the cells are cultured in the presence of an agent at a temperature between about 32° C. and about 35° C. In some embodiments, the cells are cultured at a temperature between about 32° C. and 34° C., e.g., at about 33° C. In a preferred aspect, MDC cells used herein are cultured at about 34° C.

Cells can be contacted with a chemical agent according to experimental conditions determined by the investigator. The examples below demonstrate at least one functional set of conditions useful for mammalian cells, particularly under suspension conditions. In one preferred aspect, the step of contacting the host cell may occur during incubation or expansion of cells and prior to or concurrently with inoculation of a virus.

Recombinant expression of biological molecules in host cells are standard techniques available to one of skill in the art. Methods for transfecting cells may include electroporation (gene electrotransfer), sono-poration, optical transfection, protoplast fusion, impalefection, magnetofection, or viral transduction. Commonly used transfection reagents include, for example, calcium phosphate, DEAE-dextran and lipids. For examples of detailed protocols numerous references texts are available for example, Current Protocols in Molecular Biology, Chapter 9, Ausubel, et al. Eds., John Wiley and Sons, 1998. In the case of virus or bacteria, cells are infected or inoculated at a desired multiplicity of infection (MOI). Transfection and infection may be used interchangeably herein.

The amount of biological molecules produced by host cells treated with a chemical agent may be measured before, after or simultaneously upon inoculation with a virus. Monitoring the response of viral infection of a cell membrane surrounding time of addition of chemical agents can provide an understanding of, for example, virus entry into the cell, level of virus genomic DNA and/or RNA affected, level of transcription of virus genomic DNA into RNA, level of one or more virus proteins expressed, number of virus particles formed inside the cell, and/or number of virus particles released from the cell. Without wishing to be bound by theory, it is believed that the chemical agents exert their effect on viral growth phases in host cells.

An agent may be added to a medium containing the host cell in a period of time prior to, concurrently with or in a period of time after transfection and prior to harvesting the host cells or expressed biological molecule. For example, host cells can be contacted with an effective concentration of a chemical agent at time intervals of between 0 to 1 hour, 0 to 2 hours, 0 to 3 hours, 0 to 4 hours, 0 to 5 hours, 0 to 12 hours, 0 to 20 hours, 0 to 30 hours, 0 to 40 hours, 0 to 50 hours, 0 to 60 hours prior to or post-transfection or post-infection. The contact time may be optimized to achieve a level of yield that is at least 2-fold of that achieved compared to control. Surprisingly, the chemical agents used in the present invention may be in contact with a host cell for a short period of time, preferably the cell requires no pre-treatment and the chemical agent may be added concurrently with the virus.

In selecting a suitable agent to aid for enhanced production of biological molecules of interest in host cell systems, one desirable feature may be that the agent is effective to increase production when used at relatively low concentrations at least for two reasons. First, smaller amounts of such agents would be required for a commercial-scale manufacture of such products. Second, for pharmaceutical, nutraceutical and cosmetic applications, it is desirable that the end product is in a pure form, free from contaminants or impurities. Low concentrations of such an agent used during the process of the manufacture means that removal of the agent from the end product would be easier. Another desirable feature for suitable agents in aiding the production of biological molecules of interest is that such agents are already approved, commercially available products, whose safety profiles are well-characterized.

In some embodiments, agents used in the invention are present at a sufficient concentration at the time of transfection. Conditions can be adjusted and optimized by one of skill in the art for achieving the desired parameters for increased yield of biological molecules. As mentioned above, preferably, an amount effective to enhance the production or yield of a biological molecule of interest is low enough that it is commercially feasible and safe for human use. Typically, an effective amount is measured by concentrations in a total volume of preparation when the agent is being present, such as a batch volume of a cell culture. In some embodiments, effective amounts of suitable agents used herein are between 0.1 nM and 10 $\mu$M, preferably below 5 $\mu$M, more preferably below 1 $\mu$M, even more preferably below 100 nM.

The optimal concentration of a parameter representative of increased yield or productivity may vary according to individual characteristics of the expression system, the requirements of the user, and the determination of what constitutes an optimal concentration of any one or more expression enhancer in a given experimental scenario is well within purview of a practitioner having ordinary skill level in the art.

It is possible that a combination of chemical agents may be used to contact a host cell system, such as at least two, at least three, at least four agents added sequentially or in a cocktail. Addition of a subsequent agent can be performed at time intervals between 0-1 hour, 2 hours, 3 hours, 4 hours, 5 hours post addition of the first or prior compound. Depending on the virus, host cell, transfection conditions, and expression products, treatment with chemical agents or combinations of chemical agents may result in superadditive ("synergistic") effects. For example, in addition to increased yield, the following effects exceeding the effects actually to be expected are possible: increased number of doses of biological products manufactured, reduced time from manufacture to delivery of drugs to patients, increased number of patients treated, increased protein/antigen expression, increased release of viral particles, increased NP detection depicting increased viral particle production, increased HA antigen density on viral particles, increased efficacy of a combination of chemical agents to produce biological products. Synergistic effects may be detected by applicable methods as described herein.

In one aspect, treatment of host cells may be conducted in medium that permits the interaction of the host cell system with chemical agents without the need to change the medium. In one preferred embodiment, the present invention encompasses a medium wherein both the cultivation and transfection of cells may be conducted in the presence of at least one chemical agent prior to inoculation with a virus.

The medium in which the host cells are treated may also comprise a number of ingredients, including amino acids, vitamins, organic and inorganic salts, sugars and other components, each ingredient being present in an amount which supports the cultivation of a mammalian epithelial cell in vitro.

For some applications, it may be preferable to further enrich the nutritional content of the complete media to support faster growth and enhanced production of biological molecules by the host cells, preferably to provide a more suitable environment for the culture of fastidious mammalian cells. To accomplish such enrichment, one or more supplements may optionally be added to the basal media or the complete media of the invention. Supplements which may advantageously be added to the present media include one or more cytokines (e.g., growth factors such as EGF, aFGF, bFGF, IGF-1, IGF-2, HB-EGF, KGF, HGF and the like), heparin (to stabilize heparin-binding growth factors such as the FGFs, HB-EGF, KGF and HGF) and one or more peptides derived from animals (e.g., HSA or BSA), yeasts (e.g., yeast extract, yeastolate or yeast extract ultrafiltrate) or plants (e.g., rice or soy peptides). Cytokines, which may be natural or recombinant, are available commercially, for example from Life Technologies, Inc. (Rockville, Md.) or R&D Systems, Inc. (Rochester, Minn) and may be added to the media at concentrations recommended by the manufacturer for the particular cell type to be cultured (typically a final concentration of about 0.00001-10 mg/liter). Heparin is available commercially, for example from Sigma (St. Louis, Mo.), and is preferably porcine mucosa heparin used at a final concentration in the media of about 1-500 U.S.P. units/liter. Animal, yeast and plant peptides may be obtained commercially (e.g., from Sigma for animal peptides; from Difco, Norwell, Mass., for yeast peptides; and from Quest International, Norwich, New York, for plant peptides), or may be derived and formulated into the present culture media as described in detail in co-pending, commonly owned U.S. Application No. 60/028,197, filed Oct. 10, 1996, the disclosure of which is incorporated herein by reference in its entirety.

In some aspects of the present invention a particularly suitable type of medium for the practice of the present invention is a protein-free medium (sometimes referred to as "PFM Medium") being entirely devoid of protein (e.g., no serum proteins such as serum albumin or attachment factors, nutritive proteins such as growth factors, or metal ion carrier proteins such as transferrin, ceruloplasmin, etc.).

Ideally, both serum-free and protein-free media contemplated for use with the present invention will further be devoid of any animal derived material, or any material that is derived in whole or in part from an animal source, including recombinant animal DNA or recombinant animal protein DNA.

Cell Lines and Cell Culture

According to the invention, any host cell system may be used, preferably eukaryotic, preferably mammalian. Typically vertebrate host cells include but are not limited to cells from primates (e.g., humans, monkeys, etc.), dogs, birds (e.g., hens, ducks, etc.), cats, cattle, horses, sheep, pigs, goats, rodents, and rabbits. In one preferred aspect, vertebrate cells are from embryonated eggs.

In another aspect the cell is a cell line. Typically the cultured cell is certified according to the WHO requirements for vaccine production. The requirements for certifying such cell lines include characterization with respect to at least one of genealogy, growth characteristics, immunological markers, virus susceptibility, tumorigenicity and storage conditions, as well as by testing in animals, eggs, and cell culture. Non-limiting examples of host cells suitable for the invention include eukaryotic cells, such as plant cells, mammalian cells, avian cells (such as duck cells), insect cells, yeast cells, etc. Non-limiting examples of suitable cells include: primary cells, such as primary epithelial cells (e.g., keratinocytes, cervical epithelial cells, bronchial epithelial cells, tracheal epithelial cells, kidney epithelial cells and retinal epithelial cells) and established cell lines and their strains or derivatives (e.g., 293 embryonic kidney cells, BHK cells, HeLa cervical epithelial cells and PER-C6 retinal cells, MDBK (NBL-1) cells, 911 cells, CRFK cells, MDCK cells, CaCo-2, CapT cells, CHO cells, BeWo cells, Chang cells, Detroit 562 cells, FRIIK-4, HEK-293, HeLa 229 cells, HeLa S3 cells, Hep-2 cells, KB cells, LS180 cells, LS174T cells, NCI-H-548 cells, RPMI 2650 cells, SW-13 cells, T24 cells, WI-28 VA13, 2RA cells, WISH cells, BS-C-I cells, LLC-MK2 cells, Clone M-3 cells, 1-10 cells, RAG cells, RD, TCMK-1 cells, Y-1 cells, LLC-PK1 cells, PK(15) cells, GH1 cells, GH3 cells, L2 cells, LLC-RC 256 cells, MH1C1 cells, XC cells, MDOK cells, VSW cells, and TH-I, B1 cells, or derivatives thereof), NS0 (murine myeloma cells), stem cells, such as embryonic stem cells (e.g., EB66® cells), fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., CHO cells, TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, MiCl.sub.1 cells, CHO cells, CV-1 cells, COS-1 cells, COS-3 cells, COS-7 cells, Vero cells, DBS-FrhL-2 cells, BALB/3T3 cells, F9 cells, SV-T2 cells, M-MSV-BALB/3T3 cells, K-BALB cells, BLO-11 cells, NOR-10 cells, C.sub.3H/IOTI/2 cells, HSDM1C3 cells, KLN2O5 cells, McCoy cells, Mouse L cells, Strain 2071 (Mouse L) cells, L-M strain (Mouse L) cells, L-MTK-(Mouse L) cells, NCTC clones 2472 and 2555, SCC-PSA1 cells, Swiss/3T3 cells, Indian muntjac cells, SIRC cells, CII cells, and Jensen cells, or derivatives thereof). Preferably, the mammalian cells are selected from the group consisting of MDCK, cells, 293 cells, PER-C6 cells, CHO cells or derivatives thereof.

The optimal plating and culture conditions for a given animal cell type can be determined by one of ordinary skill in the art using only routine experimentation. For routine monolayer culture conditions, cells can be plated onto the surface of culture vessels without attachment factors. Alternatively, the vessels can be precoated with natural, recombinant or synthetic attachment factors or peptide fragments (e.g., collagen, fibronectin, vitronectin, laminin and the like, or natural or synthetic fragments thereof), which are available commercially for example from Life Technologies, Inc. (Rockville, Md.), R&D Systems, Inc. (Rochester, Minn.), Genzyme (Cambridge, Mass.) and Sigma (St. Louis, Mo.). Isolated cells can also be seeded into or onto a natural or synthetic three-dimensional support matrix such as a preformed collagen gel or a synthetic biopolymeric material. For suspension cultivation, cells are typically suspended in culture media and introduced into a culture vessel that facilitates cultivation of the cells in suspension, such as a spinner flask, perfusion apparatus, or bioreactor (see Freshney, R. I., Culture of Animal Cells: A Manual of Basic Technique, New York: Alan R. Liss, Inc., pp. 123-125 (1983)). Ideally, agitation of the media and the suspended cells will be minimized to avoid denaturation of media components and shearing of the cells during cultivation.

In a preferred aspect, cells for production of influenza virus can be cultured in serum-containing or serum free medium. In some case, e.g., for the preparation of purified viruses, it is desirable to grow the cells in serum free conditions. Cells can be cultured in small scale, e.g., less than 25 ml medium, culture tubes or flasks or in large flasks with agitation, in rotator bottles, or on microcarrierbeads (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor) in flasks, bottles or reactor cultures. Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. For commercial production of viruses, e.g., for vaccine production, it is often desirable to culture the cells in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); laboratory and commercial scale bioreactors from B. Braun Biotech International (B. Braun Biotech, Melsungen, Germany).

According to a preferred aspect, the host cell may be contacted with a virus either prior to, simultaneously or following contact with a chemical agent. Optimal methods for infecting a mammalian cell with a virus are well-known in the art and will be familiar to one of ordinary skill. Virus infection of cells can be quantitated in a variety of ways. MOI is the ratio of infectious virus particles to the number of cells being infected. Thus, an MOI of 0.1 results in the average inoculation of 1 virus particle for every 10 cells. The general theory behind MOI is to introduce one infectious virus particle to every host cell that is present in the culture. However, more than one virus may infect the same cell which leaves a percentage of cells uninfected. This occurrence can be reduced by using a higher MOI to ensure that every cell is infected. The provided viral particles can therefore be administered to cells, as described herein, with a MOI of 0.001 to 100, such as for example 1, 2, 3, 4, 5, 6, 7, 8, 9, 10, 11, 12, 13, 14, 15, 16, 17, 18, 19, 20, 30, 40, 50, 60, 70, 80, 90, 100.

Virus-infected mammalian cells cultivated in suspension in the presence of an agent may be expected to produce higher virus titers (e.g., 2-, 3-, 5-, 10-, 20-, 25-, 50-, 100-, 250-, 500-, or 1000-fold higher titers) than those cells that were not contacted with the candidate compound. These methods may be used to produce a variety of mammalian viruses and viral vectors, including but not limited to retroviruses and the like, and are most preferably used to produce influenza viruses. Following treatment of the infected cells with a chemical agent, the used culture media comprising viruses, viral vectors, viral particles or components thereof (proteins and/or nucleic acids (DNA and/or RNA)) may be used for a variety of purposes, including vaccine production, production of viral vectors for use in cell transfection or gene therapy, infection of animals or cell cultures, study of viral proteins and/or nucleic acids and the like. Alternatively, viruses, viral vectors, viral particles or components thereof may optionally be isolated from the used culture medium according to techniques for protein and/or nucleic acid isolation that will be familiar to one of ordinary skill in the art.

The present invention may also be used in methods for the production of recombinant proteins from mammalian cells, particularly from mammalian cells grown in suspension. Cells may be genetically engineered prior to contact with a chemical agent, or they may be transfected with one or more exogenous nucleic acid molecules and contacted with a sufficient amount of a chemical agent. Optimal methods for genetically engineering a mammalian cell to express a polypeptide of interest are well-known in the art and will therefore be familiar to one of ordinary skill. Genetically engineered cells may be cultivated in the presence of an agent either as monolayer cultures, or more preferably as suspension cultures according to the methods described herein. Following cultivation of the cells, the biological molecule of interest may optionally be purified from the cells and/or the used culture medium according to techniques of protein isolation that will be familiar to one of ordinary skill in the art. The isolation and purification of the biological molecules or derivatives thereof, produced by the method according to the present invention, is performed by means of the usual methods that are known to the person skilled in the art.

In general, isolation of proteins initially depends on their origin. A distinction is made between intra- and extracellular proteins. If the proteins are located within the cell bodies, breaking the cells is necessary first, which is performed e.g. by shear forces or osmolysis. Thereafter the separation of insoluble material, such as cell membranes and cell walls, is done, e.g. by centrifugation. Centrifugation is used by default for the separation of cells, cell organelles and proteins. A more effective method in terms of the separation capacity is pulse electrophoresis. Additionally, after separation of other cell components, there is still the need to separate different sized proteins, peptides and amino acids. The separation of proteins may be done by one or two-dimensional gel electrophoresis or capillary electrophoresis. In the field of amino acids and peptides, for example, chromatographic methods, such as affinity chromatography, ion exchange chromatography (IEC), or reversed-phase chromatography (RPC) are used. The presence of lipids and the necessity of removal or deactivation of proteases are disadvantageous with regard to the purification. Proteins present in the extracellular matrix need not be extracted from the cells, but, after separation of all insolubles, they are highly diluted and usually in much smaller quantities than as intracellular proteins.

Virus Processing

Following culture of a host cell for a suitable period of time to permit replication of virus to high titers, the virus can be recovered. Viruses can typically be recovered from the culture medium, in which infected cells have been grown. Typically crude medium is clarified prior to concentration of influenza viruses. Common methods include filtration, ultrafiltration, adsorption on barium sulfate and elution, and centrifugation. For example, crude medium from infected cultures can first be clarified by centrifugation at, e.g., 1000-2000×g for a time sufficient to remove cell debris and other large particulate matter, e.g., between 10 and 30 minutes. Alternatively, the medium is filtered through a 0.8 μm cellulose acetate filter to remove intact cells and other large particulate matter. Optionally, the clarified medium supernatant is then centrifuged to pellet the influenza viruses, e.g., at 15,000×g, for approximately 3-5 hours. Following resuspension of the virus pellet in an appropriate buffer, such as STE (0.01M Tris-HCl; 0.15M NaCl; 0.0001M EDTA) or phosphate buffered saline (PBS) at pH 7.4, the virus is concentrated by density gradient centrifugation on sucrose (60%-12%) or potassium tartrate (50%-10%). Either continuous or step gradients, e.g., a sucrose gradient between 12% and 60% in four 12% steps, are suitable. The gradients are centrifuged at a speed, and for a time, sufficient for the viruses to concentrate into a visible band for recovery. Alternatively, and for most large scale commercial applications, virus is eluted from density gradients using a zonal-centrifuge rotor operating in continuous mode. Additional details sufficient to guide one of skill through the preparation of influenza viruses from tissue culture are provided, e.g., in Furminger. Vaccine Production, in Nicholson et al. (eds) Textbook of Influenza pp. 324-332; Merten et al. (1996) Production of influenza virus in cell cultures for vaccine preparation, in Cohen & Shafferman (eds) Novel Strategies in Design and Production of Vaccines pp. 141-151, and U.S. Pat. No. 5,690,937, U.S. publication application nos. 20040265987, 20050266026 and 20050158342, which are incorporated by reference herein. If desired, the recovered viruses can be stored at −80° C. in the presence of sucrose-phosphate-glutamate (SPG) as a stabilizer.

The viruses produced by the method of the present invention can be processed into vaccine preparations. Such vaccine preparations can be obtained by the following process, which is a particularly preferred embodiment:

Influenza virus vaccine can be prepared as follows: influenza viruses are grown in cell culture, e.g. in MDCK suspension cells (WO97/037000). The viruses are harvested, purified and concentrated by 0.45 micrometer filtration and CS chromatography. After addition of detergent (e.g. tween 80), the virus preparation is treated with BPL. Afterwards the viruses are split with CTAB. After an ultracentrifugation and adsorption step the viral protein preparation is subject to ion exchange chromatography, using TMAE or Sartobind Q as a resin. The chromatography may be done in the presence of sodium caprylate (about 50 mM for Sartobind; 100 mM for TMAE) and sodium chloride (400 mM for Sartobind), and 200 mM for TMAE). Prior to the use of the detergent in combination with ion exchange chromatography, parts of the fragmented residual DNA can be removed by precipitation with a cationic detergent like CTAB as described in Onions et al, Biologicals 2010 (38) 544-551). The present invention can be applied as part of the Onions process.

Afterwards the protein preparation is concentrated per ultrafiltration. The proteins might be optionally blended with other virus preparation (in the case of tri- or tetravalent seasonal vaccines), and optionally sterile filtrated, filled and packaged. Part of the invention includes influenza vaccine obtainable by this process.

Assays

In one example, analyzing the cellular productivity of a host cell exposed to chemical agents may involve determination of cellular productivity, for example, measurement of at least one expression product. Cellular productivity as used herein refers to the total amount of recombinantly expressed protein (e.g., polypeptides, antibodies, etc.) or particle produced by a cell per unit time, under certain growth conditions.

Cellular productivity can also be determined by identification of a change in the nature of the biological product or cellular phenotype in the presence of a chemical agent compared to corresponding control in the absence of the agent. Preferably the expression or biological product in this method measures production of viral particles, nucleic acid or proteins.

In a particular aspect, direct measurement of a biological molecule is more accurate than standard plaque assays.

In a preferred example, the expression product is an HA protein measured using ELISA and techniques readily available to the skilled person. The HA protein may be a purified glycoprotein protein or bound to viral components such as split or whole virion membranes.

To measure the synthesis of nucleic acid sequences encoding recombinant proteins, RNA or DNA may be measured using well-known methods such as Northern blot methods as well as RT-PCT that utilizes classic nucleic acid hybridization techniques.

Antigens

An antigen can be any molecule (e.g., nucleic acid, DNA, RNA, protein, peptide, glycoprotein, glycopeptide, carbohydrate, lipid, lipopeptide, polysaccharide) that can be recognized by the components of the immune system regardless of whether it can trigger activation of the immune system.

The antigen may be associated with a pathogen such as vaccinia, avipox virus, turkey influenza virus, bovine leukemia virus, feline leukemia virus, avian influenza, chicken pneumovirosis virus, canine parvovirus, equine influenza, FHV, Newcastle Disease Virus (NDV), Chicken/Pennsylvania/1/83 influenza virus, infectious bronchitis virus; Dengue virus, measles virus, Rubella virus, pseudorabies, Epstein-Barr Virus, HIV, SIV, EHV, BHV, HCMV, Hantaan, *C. tetani*, mumps, Morbillivirus, Herpes Simplex Virus type 1, Herpes Simplex Virus type 2, Human cytomegalovirus, Hepatitis A Virus, Hepatitis B Virus, Hepatitis C Virus, Hepatitis E Virus, Respiratory Syncytial Virus, Human Papilloma Virus, Influenza Virus, *Salmonella, Neisseria, Borrelia, Chlamydia, Bordetella, Plasmodium* (e.g., *Plasmodium falciparum* and *Plasmodium vivax*), *Toxoplasma, Cryptococcus, Streptococcus, Staphylococcus, Haemophilus, Diptheria, Tetanus, Pertussis, Escherichia, Candida, Aspergillus, Entamoeba, Giardia* and *Trypanasoma*. The antigens can be a fragment or portion of a naturally occurring antigen or a synthetic molecule that mimics the naturally occurring antigen or a portion of the naturally occurring antigen.

In a preferred aspect, any influenza virus strain or subtype are encompassed by the invention. Preferably, the influenza virus strain corresponds to a clinical isolate of at least one circulating strain of an influenza A or B virus. Type A viruses are principally classified into antigenic sub-types on the basis of two viral surface glycoproteins, hemagglutinin (HA) and neuraminidase (NA). There are currently 16 identified HA sub-types (designated HI through H16) and 9 NA sub-types (N1 through N9) all of which can be found in wild aquatic birds. Of the 135 possible combinations of HA and NA, only four (H1N1, H1N2, H2N2, H5N1 and H3N2) have widely circulated in the human population since the virus was first isolated in 1933.

The method of the present invention shows particular improvement in production of subtypes and strains which have been difficult to produce. For example, the reassortment processes are generally not used for Influenza B vaccines because of a lack of suitable high yielding influenza B donor strains that are sufficiently distinct antigenically. Most likely reassortment as a process has been underestimated as the evolution of influenza B virus has been measured using data obtained from HA genes only. Nevertheless, the present invention significantly improves the yield of antigenic proteins obtained from Type B strains including strains in more constant and less labor intensive manner as yet unachievable prior to the present invention. Type B strains could be produced at greater than 20 μg/ml, 30 μg/ml, 40 μg/ml, 50 μg/ml, 60 μg/ml as measured by RP-HPLC of sucrose purified virus cultures. Yield of type B antigens are strain specific and it is possible that certain strains may produce less than the average 20 μg/ml seen in common influenza strains and subtypes. In cases where yield is dependent on the strain or type, increases in yield may be a relative measurement which can be determined in comparison to the control strain or type.

An influenza B vaccine may be part of a monovalent, bivalent, trivalent, quadrivalent or heptavalent vaccine, which may include more than one subtype B strain and may include combinations of other strains such as but not limited to H1, H2, H3, H5, H7 and/or H9 strains.

Suitable strains of Subtype B influenza virus produced by the invention include influenza virus B, influenza virus B/Ann Arbor 1/86, influenza virus B/Harbin/7/94, influenza virus B/Hong Kong/5/72, influenza virus B/Lee/40, influenza virus B/Victoria group, influenza virus B/Yamagata 16/88, influenza virus B/Yamagata group, influenza virus B/Yamanashi/166/98, influenza virus type B/Panama 45/90.

In a particularly advantageous aspect, the methods of the present invention enhance yield of pandemic influenza strains including, but not limited to, turkey influenza virus strain A/Turkey/Ireland/1378/83 (H5N8), turkey influenza virus strain A/Turkey/England/63 (H7N3), turkey influenza virus strain A/Turkey/England/66 (H6N2), A/Turkey/England/69 (H7N2), A/Turkey/Scotland/70 (H6N2); turkey influenza virus strain A/Turkey/England N28/73 (H5N2), turkey influenza virus strain A/Turkey/England/110/77 (H6N2), turkey influenza virus strain A/Turkey/England/647/77 (H1N1), turkey influenza virus strain A/Turkey/Ontario/7732/66 (H5N9), turkey influenza virus strain A/Turkey/England/199/79 (H7N7), turkey influenza virus strain A/Turkey/Ontario/7732/66 (H5N9), turkey influenza virus strain A/Turkey/Ireland/1378/85 (H5N8), turkey influenza virus strain A/Turkey/England/50-92/91 (H5N1), turkey influenza virus strain A/Turkey/Wisconsin/68 (H5N9), turkey influenza virus strain A/Turkey/Massachusetts/65 (H6N2), turkey influenza virus strain A/Turkey/Oregon/71 (H7N3), turkey influenza virus strain A/Turkey/Ontario/6228/67 (H8N4), turkey influenza virus strain A/Turkey/Wisconsin/66 (H9N2), turkey influenza virus strain A/Turkey/England/647/77 (H1N1), turkey influenza virus strain A/Turkey/Ontario/6118/68 (H8N4), turkey influenza virus strain A/Tur/Ger 3/91, turkey influenza virus strain A/Turkey/Minnesota/833/80 (H4N2), chicken influenza virus strain A/Chicken/Indonesia/03 (H5N1), chicken influenza virus strain A/Chicken/FPV/Rostock/1934, chicken influenza virus strain A/Chicken/Texas/298313/04, chicken influenza virus strain A/Chicken/Texas/167280-4-/02, chicken influenza virus strain A/Chicken/Hong Kong/220/97, chicken influenza virus strain A/Chicken/Italy/8/98, chicken influenza virus strain A/Chicken/Victoria/76 (H7N7), chicken influenza virus strain A/Chicken/Germany/79 (H7N7), chicken influenza virus strain A/Chicken/Scotland/59 (H5N1); chicken influenza virus strain A/Chicken/Pennsylvania/1370/83 (H5N2), chicken influenza virus strain A/Chicken/Queretaro-19/95 (H5N2), chicken influenza virus strain A/Chicken/Queretaro-20/95 (H5N2), chicken influenza virus strain A/Chicken/Hong Kong/258/97 (H5N1), chicken influenza virus strain A/Chicken/Italy/1487/97 (H5N2), chicken influenza virus strain A/Chicken/Leipzig/79 (H7N7), chicken influenza virus strain A/Chicken/Victoria/185 (H7N7), chicken influenza virus strain A/Chicken/Victoria/92 (H7N3), chicken influenza virus strain A/Chicken/Queensland/95 (H7N3), chicken influenza virus strain A/Chicken/Pakistan/1369/95 (H7N2), chicken influenza virus strain A/Chicken/Pakistan/447-4/95 (H7N3), chicken influenza virus strain A/Chicken/HK/G9/97 (H9N2), chicken influenza virus strain A/Chicken/Nakom-Patom/Thailand/CU-K2/2004 (H5N1), chicken influenza virus strain A/Chicken/Hong Kong/31.2/2002 (H5N11), chicken influenza virus strain A/Chicken/Vietnam/C58/04 (H5N1), chicken influenza virus strain A/Chicken/Vietnam/38/2004 (H5N1), chicken influenza virus strain A/Chicken/Alabama/7395/75 (H4N8), chicken influenza virus strain A/Chicken/Germany/N/49 (H100N7), chicken influenza virus strain A/Chicken/Beijing/1/94 (H9N2), chicken influenza virus strain A/Chicken/Hong Kong/G23/97 (H9N2), chicken influenza virus strain A/Chicken/Pennsylvania/8125/83 (H5N2), chicken influenza virus strain A/Chicken/Hong Kong/97 (H5N1), duck influenza virus strain A/Duck/Anyang/AVL-1/01, duck influenza virus strain A/Duck/New York/17542-4/86 (H9N1), duck influenza virus strain A/Duck/Alberta/28/76 (H4N6), duck influenza virus strain A/Duck/Nanchang/4-165/2000 (H4N6), duck influenza virus strain A/Duck/Germany/49 (H10N7), duck influenza virus strain A/Black Duck/Australia/702/78 (H3N8), duck influenza virus strain A/Duck/Vietnam/11/2004 (H5N1), duck influenza virus strain A/Duck/Alberta/60/76 (H12N5), duck influenza virus strain A/Duck/Hong Kong/196/77 (H1), duck influenza virus strain A/Duck/Wisconsin/1938/80 (H1N1), duck influenza virus strain A/Duck/Bavaria/2/77 (H1N1N1), duck influenza virus strain A/Duck/Bavaria/1/77 (H1N1), duck influenza virus strain A/Duck/Australia/749/80 (H1N1), duck influenza virus strain A/Duck/Hong Kong/Y280/97 (H9N2), duck influenza virus strain A/Duck/Alberta/35/76 H1N1), avian influenza virus strain A/Mallard duck/Gurjev/263/82 (H14N5), avian influenza virus strain A/Mallard duck/PA/10218/84 (H5N2), avian influenza virus strain A/Mallard duck/Astrakhan/244/82 (H14N6), goose influenza virus strain A/Goose/Guangdong/1/96, goose influenza virus strain A/Goose/Leipzig/137-8/79 (H7N7), goose influenza virus strain A/Goose/Hong Kong/W222/97 (H6N7), goose influenza virus strain A/Goose/Leipzig/187-7/79 (H7N7), goose influenza virus strain A/Goose/Leipzig/192-7/79 (H7N7), avian influenza virus strain A/Env/HK/437-4/99, avian influenza virus strain A/Env/HK/437-6/99, avian influenza virus strain A/Env/HK/437-8/99, avian influenza virus strain A/Env/HK/437-10/99, avian influenza virus strain A/Fowl plague virus strain/Dutch/27 (H7N7), avian influenza virus strain A/Fowl plague virus strain/Dobson/27 (H7N7), avian influenza virus strain A/Fowl plague virus strain/Rostock/34 (H7N1), avian influenza virus strain A/Fowl plague virus strain/Egypt/45 (H7N1), avian influenza virus strain A/Fowl plague virus strain/Weybridge (H7N7), avian influenza virus strain A/Tem/South Africa/61 (H5N3), avian influenza virus strain A/Tern/Australia/G70C/75 (H11N9), avian influenza virus strain A/Quail/Vietnam/36/04 (H5N1), avian influenza virus strain A/Gull/Maryland/704/77 (H13N6), avian influenza virus strain A/Black-headed gull/Sweden/5/99 (H16N3), avian influenza virus strain A/Herring gull/DE/677/88 (H2N8), avian influenza virus strain A/Swan/Italy/179/06 (H5N1), avian influenza virus strain A/Hong Kong/156/97 (A/HK/156/97), avian influenza virus strain A/Quail/HK/G1/97 (H9N2), avian influenza virus strain A/Quail/Hong Kong/AF157/93 (H9N2), avian influenza virus strain A/Teal/HK/W312/97 (H6N1), avian influenza virus strain A/Shearwater/West Australia/2576/79 (H15N9), avian influenza virus strain A/Shearwater/Australia/72 (H6N5), avian influenza virus strain A/Hong Kong/212/03, avian influenza virus strain A/England/321/77 (H3N2), avian pandemic influenza A viruses of avian origin, avian H5N1 influenza virus, avian H7N1 influenza strain, avian H9N2 influenza virus, and avian influenza virus, cold-adapted (ca) and temperature sensitive (ts) master donor strain, A/Leningrad/134/17/57 (H2N2).

Influenza virus vaccines may comprise all proteins, peptides or parts thereof, as well as nucleic acids which encode these proteins, peptides or parts thereof, of the influenza virus, as well as influenza virus particles itself, recombinant influenza virus proteins, including influenza envelope proteins, sub-viral particles, virus-like particles (VLP), VLP-complexes, and/or parts thereof, which may be used for immunization purposes against influenza.

Inactivated influenza virus vaccines can typically be provided by inactivating replicated virus of the invention using known methods, such as, but not limited to, formalin or beta-propiolactone treatment. Inactivated vaccine types that can be used in the invention can include whole-virus (WV) vaccine or subvirion (SV) virus vaccine. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen vaccines. In general, the responses to SV surface antigen (i.e., purified HA or NA)

vaccines are similar. An experimental inactivated WV vaccine containing an NA antigen immunologically related to the epidemic virus and an unrelated HA appears to be less effective than conventional vaccines. Inactivated vaccines containing both relevant surface antigens are preferred.

Live, attenuated influenza virus vaccines, using replicated virus can also be used for preventing or treating influenza virus infection, according to known method steps: Attenuation is preferably achieved in a single step by transfer of attenuating genes from an attenuated donor virus to a replicated isolate or reassorted virus according to known methods (see, e.g., Murphy, Infect. Dis. Clin. Pract. 2:174-181 (1993)). Since resistance to influenza A virus is mediated by the development of an immune response to the HA and NA glycoproteins, the genes coding for these surface antigens must come from the reasserted viruses or high growth clinical isolates. The attenuating genes are derived from the attenuated parent. In this approach, genes that confer attenuation preferably do not code for the HA and NA glycoproteins. Otherwise, these genes could not be transferred to reassortants bearing the surface antigens of the clinical virus isolate. Many donor viruses have been evaluated for their ability to reproducibly attenuate influenza viruses. As a non-limiting example, the A/Ann Arbor(AA)/6/60 (H2N2) cold adapted (ca) donor virus can be used for attenuated vaccine production (see, e.g., Edwards, J. Infect. Dis. 169:68-76 (1994); Murphy, Infect. Dis. Clin. Pract. 2:174-181 (1993)). Additionally, live, attenuated reassortant virus vaccines can be generated by mating the donor virus with a virulent replicated virus of the invention. Reassortant progeny are then selected at 25° C. (restrictive for replication of virulent virus), in the presence of an H2N2 antiserum, which inhibits replication of the viruses bearing the surface antigens of the attenuated AI AAI6/60 (H2N2) ca donor virus.

Other attenuating mutations can be introduced into influenza virus genes by site-directed mutagenesis to rescue infectious viruses bearing these mutant genes. Attenuating mutations can be introduced into non-coding regions of the genome, as-well as into coding regions. Such attenuating mutations can also be introduced into genes other than the HA or NA, e.g., the PB2 polymerase gene (Subbarao et al., J. Virol. 67:7223-7228 (1993)). Thus, new donor viruses can also be generated bearing attenuating mutations introduced by site-directed mutagenesis, and such new donor viruses can be used in the production of live attenuated reassortants H1N1 and H3N2 vaccine candidates in a manner analogous to that described above for the AI AAI6/60 ca donor virus. Similarly, other known and suitable attenuated donor strains can be reassorted with replicated influenza virus of the invention to obtain attenuated vaccines suitable for use in the vaccination of mammals. (Ewami et al., Proc. Natl. Acad. Sci. USA 87:3802-3805 (1990); Muster et al., Proc. Natl. Acad. Sci. USA 88:5177-5181 (1991); Subbarao et al., J. Virol. 67:7223-7228 (1993); U.S. patent application Ser. No. 08/471,100, which references are entirely incorporated by reference).

Vaccine Formulations

Vaccine compositions of the present invention, suitable for inoculation or for parenteral or oral administration, comprise attenuated or inactivated influenza viruses, optionally further comprising sterile aqueous or non-aqueous solutions, suspensions, and emulsions. The composition can further comprise auxiliary agents or excipients, as known in the art.

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate.

Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents. See, e.g., Berkow, infra, Goodman, infra, Avery's, infra, Osol, infra and Katzung, infra, which are entirely incorporated herein by reference, included all references cited therein.

When a vaccine composition of the present invention is used for administration to an individual, it can further comprise salts, buffers, adjuvants, or other compounds which are desirable for improving the efficacy of the composition.

Adjuvants are compounds that can be used to augment a specific immune response. Normally, the adjuvant and the composition are mixed prior to presentation to the immune system, or presented separately, but into the same site of the mammal being immunized.

Heterogeneity in the vaccine may be provided by mixing replicated influenza viruses for at least two influenza virus strains, such as 2-50 strains or any range or value therein.

According to the present invention, vaccines can be provided for variations in a single strain of an influenza virus or for more than one strain of influenza viruses, using techniques known in the art.

Once prepared the vaccine composition may be then administered in a subject in need thereof. Typically, an attenuated or inactivated vaccine composition of the present invention may thus be provided either before the onset of infection (so as to prevent or attenuate an anticipated infection) or after the initiation of an actual infection. For example, administration of such a vaccine composition may be by various parenteral routes such as subcutaneous, intravenous, intradermal, intramuscular, intraperitoneal, intranasal, oral or transdermal routes. Parenteral administration can be by bolus injection or by gradual perfusion over time. A preferred mode of using a vaccine composition of the present invention is by intramuscular or subcutaneous application. See, e.g., Berkow, infra, Goodman, infra, Avery, infra and Katzung, infra, which are entirely incorporated herein by reference, including all references cited therein.

The vaccine composition is administered to the subject in an effective amount. An effective amount of a vaccine composition is one that is sufficient to achieve a desired biological effect. It is understood that the effective dosage will be dependent upon the age, sex, health, and weight of the recipient, kind of concurrent treatment, if any, frequency of treatment, and the nature of the effect wanted. The ranges of effective doses provided below are not intended to limit the invention and represent preferred dose ranges. However, the most preferred dosage will be tailored to the individual subject, as is understood and determinable by one of skill in the art, without undue experimentation.

The patent includes the following specific embodiments. In one embodiment the invention relates to a method for producing therapeutic, prophylactic or diagnostic biological molecules from a host cell system comprising contacting a host cell system with at least one chemical agent selected from Tables 1. The host cell can be a cell culture or an embryonated egg. The cell culture is preferably selected from the group of MDCK, Vero, BHK, PERC6 or CHO. In a preferred embodiment the biological molecule is an antibody, an antibody fragment, or a vaccine antigen, in particular a viral antigen, particularly preferred a flu antigen. In a preferred embodiment statin or statin analogs other than Simvastatin are used as chemical agents. In a preferred embodiments the concentration of these non-Simvastatin statins is between 0.001 μM to 10 μM, particularly preferred less or equal to 0.05 μM. In a preferred embodiment compound of the following general formula are used:

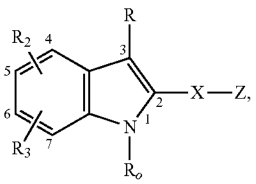

or

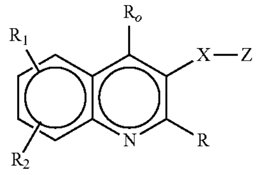

In a particularly preferred embodiment fluvastatin, pitavastatin, atorvastatin, cerivastatin, lovastatin, mevastatin, pravastatin or rosuvastatin, or derivatives of these compounds are used, in particular fluvastatin or pitavastatin or derivatives.

In another preferred embodiment of the invention the produced biological molecule is further processed to yield a final sterile product, e.g. by additional concentration, purifications, filtration, formulation, sterilization and filling steps. So in one embodiment the patent relates to a method for producing a therapeutic, prophylactic or diagnostic biological molecules from a host cell, comprising contacting the host cells with a chemical compound described in Table 1, harvesting the biological molecule and processing the biological molecule into a final therapeutic, prophylactic or diagnostic product. Preferably the product is an influenza vaccine, in particular an influenza B vaccine.

Definitions

The term "host cell" means a cell which contains a heterologous nucleic acid, such as a vector, and supports the replication and/or expression of nucleic acid, and optionally production of one or more encoded products including a polypeptide and/or a virus. Host cells can be prokaryotic cells such as *E. coli*, or eukaryotic such as yeast, insect, amphibian, avian or mammalian cells, including human cells and cells in embryonated eggs. The term host cell encompasses, cultured cells, combinations or mixtures of host cells including, e.g., mixed cultures of different cell types or cell lines (e.g., Vero and CEK cells).

"Biological molecules", "biological product" as used herein comprises any molecule isolated from a living organism, as well as derivatives, mutants or variants and/or biologically active fragments of the same. In the context of the present invention, biological molecules or biological products encompass biopharmaceuticals or biologics. For example, the biological product can be a protein, such as: antigens, enzymes (e.g., kinases, proteases, phosphatases, transferases, coagulation factors, etc.), peptides, antibodies, receptors, fusion proteins, growth factors, hormones, cytokines (e.g., chemokines, interferons, interleukins, lymphokines, tumour necrosis factors), neurotoxins, and the like. The biological product can be nucleic acid, nucleotide, carbohydrate, lipid, virus or bacterial proteins for instance for use in vaccines, viral particles. Preferably the biological molecule can be used as an active ingredient in a pharmaceutical preparation such as a vaccine or a pharmaceutical. In the context of the present invention, the terms "product", "protein" and biological molecules may be used interchangeably herein. In some embodiments, suitable biological molecules are recombinant proteins, including but are not limited to: secreted proteins, fragments of proteins (e.g., extracellular domains of trans-membrane proteins), chimeric proteins, and/or tagged proteins. One or more tags, if present, may be on the C-terminus, N-terminus, and/or placed within the protein (for example between two modules). In some embodiments, such recombinant proteins may contain one or more signal peptide moieties. In some embodiments, such recombinant proteins may be in the form of precursors (e.g., pro-hormones) or metabolites thereof.

The term "improves", "increases" or "enhance" refers to a statistically significant or a physiologically significant amount as compared to a corresponding control.

The term "candidate compound" or "chemical agent" refers to any chemical entity, pharmaceutical, drug, and the like that is used to modulate expression or production of biological molecules in host cell systems such as cell culture or eggs. Chemical agents as used herein also include analogs and pharmaceutically acceptable carriers, diluents and formulations thereof.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, a "prodrug" is a compound that may be converted under physiological conditions or by solvolysis to the specified compound or to a pharmaceutically acceptable salt of such compound. Prodrugs include compounds wherein an amino acid residue, or a polypeptide chain of two or more amino acid residues, is covalently joined through an amide or ester bond to a free amino, hydroxy, or carboxylic acid group. The amino acid residues contemplated include but are not limited to the 20 naturally-occurring amino acids. Other suitable amino acids include 4-hydroxyproline, hydroxylysine, demosine, isodemosine, 3-methyl histidine, norvaline, β-alanine, δ-aminobutyric acid, citrulline, homocysteine, homoserine, ornithine and methionine sulfone.

The term "treat", "treatment", "contact", "in the presence of" refers to the addition or mixing of a chemical agent in solution or a medium that facilitates interaction of the cell with the agent. The term "treat" or "treatment" when used in the context of administration to a subject (e.g., patient) refers to an act of therapeutic and/or prophylactic intervention to effectuate desirable outcome in the subject, such as to alleviate, cure, delay onset of, reduce severity of, prevent or reduce probability of occurrence of a condition or disease in a population. For example, the present invention may be carried out to manufacture a pharmaceutical composition (therapeutic and/or prophylactic), which may be used to in a method for treating a subject in need thereof, where the method comprises administering to the subject an effective amount of the composition.

As used herein, the terms "effective amount" and "effective dose" refer to any amount or dose of a compound or composition that is sufficient to fulfill its intended purpose (s), i.e., a desired biological or medicinal response in a tissue or subject at an acceptable benefit/risk ratio. The relevant intended purpose may be objective (i.e., measurable by some test or marker) or subjective (i.e., subject gives an indication of or feels an effect). In some embodiments, an effective amount is an amount that, when administered to a population of subjects that meet certain clinical criteria, a statistically significant response is obtained among the population. An effective amount is commonly administered in a dosing regimen that may comprise multiple unit doses. For any particular pharmaceutical agent, an effective amount (and/or an appropriate unit dose within an effective dosing regimen) may vary, for example, depending on route of administration, on combination with other pharmaceutical agents. In some embodiments, an effective amount is an amount that elicits a sufficient (e.g., protective) immune response that is statistically significant in a target population. In some embodiments, the specific effective amount (and/or unit dose) for any particular patient may depend upon a variety of factors, including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific pharmaceutical agent employed; the duration of the treatment; and like factors as is well known in the medical arts. In some embodiments, an effective amount is an amount that, when administered according to a particular regimen, produces a positive outcome with a reasonably acceptable level of adverse side effects, such that the side effects, if present, are tolerable enough for a patient to continue with the regimen. Those of ordinary skill in the art will appreciate that in some embodiments of the invention, a unit dosage may be considered to contain an effective amount if it contains an amount appropriate for administration in the context of a dosage regimen correlated with a positive outcome.

A "population" (as in "target population") may refer to a group of individuals (e.g., patients) that meet certain clinical criteria. Typically, a statistically significant biological effect may be observed in a population of at least 50 individuals, preferably more. A population may be defined by age, such as the elderly (e.g., 65 of age or older); pediatric (e.g., neonates, infants, children 2-12 years, 3-6 years, 2-7 years, or 6-12 years), adolescents (e.g., 12-16 years, 12-18 years, 13-19 years or 19-21 years), young adults (e.g., 17-24 years), adults (e.g., 18-64 years), etc. Additionally or alternatively, a population may be defined by certain medical condition(s), such as those with suppressed immunity, those with prior history of a specific condition, those at higher risk of developing a particular medical condition, those with a certain genetic background, those diagnosed with a particular disease or disorder, those receiving or scheduled to receive a particular treatment therapy, or any combinations thereof.

A "control" refers to host cell(s) or systems including host cells, that undergoes substantially identical testing but which has not been in contact with a chemical agent or which has been treated with DMSO. Alternatively, a control refers to a test compound which is used as the comparative agent from which other compounds or systems are compared.

The phrase "low concentration" of chemical agents as used herein refers to the presence of compounds at 0.1 nM to 10 μM. A low concentration is a relative amount and can encompass concentrations greater than disclosed herein. Suitably, the term lower concentration refers to a range of concentrations that can adequately produce desired results herein compared to a control in a particular system.

The term "degradation product" in the present context means an impurity resulting from a chemical change in the composition brought about during manufacture and/or storage of the composition by the effect of, for example, light, temperature, pH, water or by reaction with an excipient and/or the immediate container closure system.

EXAMPLES

Outline of Scientific Approach

To identify chemical compounds suitable to enhance growth or product recovered from a biological production system (for example, influenza virus production in MDCK cells) the following approach was used: (1) High-throughput screens were performed using a library of small molecules that include innate immune suppressors and low-toxicity compounds which target relevant biological processes and cellular pathways at different stages of the influenza virus life cycle. (2) The effect of the lead compounds was confirmed in research-scale MDCK suspension cell cultures using multiple flu strains and subtypes. (3) An SAR analysis of lead compounds was conducted and additional structurally-related analogs were screened. (4) The mechanism-of-action (MOA) of lead compounds was analysed (5) Proof of concept studies are conducted in a bioreactor system. Several compounds are identified which, even in low concentrations, produce substantial increase in yield over various flu strains and subtypes, including influenza B strains.

Example 1—High Throughput Screening

In an assay procedure (High Throughput Screening (HTS)), compounds were tested in 384-well format containing MDCK 33016PF cells (cells are described in U.S. Pat. No. 6,455,298) infected with A/reassortant/NYMC X-183 H3N2 influenza. A library of 14,398 chemical agents were subjected to a primary screen using a Nucleoprotein (NP)-ELISA at a compound concentration of 1 μM. 1547 hits from the primary screen were subjected to NP-ELISA in a dose response assay using a compound concentration range of 0.001 μM-10 μM. A secondary screen was then conducted on 268 hits from the primary screen by HA-ELISA in a dose response assay. The secondary screen produced 88 hits, 80 of these hits exhibited at least a 50% increase in NP and/or HA at a compound concentration of less than 10 μM.

In one instance, for the highest concentration tested, neither HA nor NP signal were measurable. For example, a statin drug concentration of 10.0 μM produced a −12.34% increase in HA and a −11.44% NP signal. It is possible that at this high dose cholesterol depletion from, e.g. the host cell membrane or virus membrane was the result of the statin function, thereby compromising cell and viral membrane integrity. The top ten compounds selected for testing are included in Table 2.

The two most effective compounds selected for further testing are: sulphonamide (an analog of Formula 3)

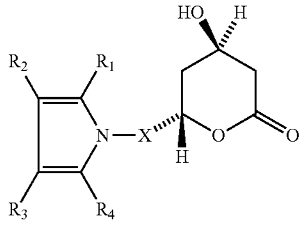

and pitavastatin (an analog of Formula 2)

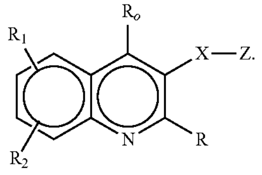

TABLE 2

| Compound | Well concentration (uM) | Avg % increase of HA yield | Average % increase of NP signal |
|---|---|---|---|
| Tetrahydopyridine 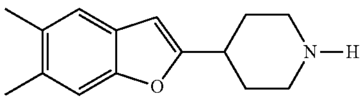 | 0.08 | 24.89 | 27.29 |
| | 0.16 | 30.19 | 44.21 |
| | 0.31 | 27.89 | 40.52 |
| | 0.63 | 38.90 | 64.44 |
| | 1.25 | 50.71 | 65.48 |
| | 2.50 | 86.11 | 104.71 |
| | 5.00 | 91.58 | 137.47 |
| | 10.00 | 102.19 | 166.64 |
| Sulphonamide 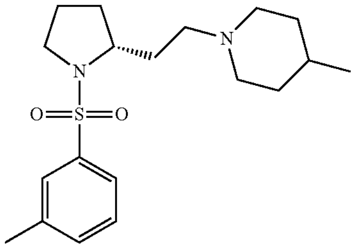 | 0.08 | 64.93 | 21.01 |
| | 0.16 | 64.33 | 31.11 |
| | 0.31 | 64.38 | 23.61 |
| | 0.63 | 91.94 | 21.38 |
| | 1.25 | 92.47 | 50.73 |
| | 2.50 | 129.92 | 65.71 |
| | 5.00 | 122.77 | 87.25 |
| | 10.00 | 159.01 | 107.41 |
| Tropanyl 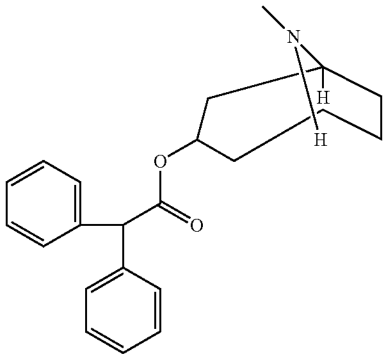 | 0.08 | 33.48 | −1.47 |
| | 0.16 | 37.55 | 1.76 |
| | 0.31 | 42.65 | 12.87 |
| | 0.63 | 48.67 | 22.70 |
| | 1.25 | 58.61 | 52.25 |
| | 2.50 | 77.61 | 87.42 |
| | 5.00 | 82.92 | 133.32 |
| | 10.00 | 123.48 | 175.04 |

TABLE 2-continued
| Compound | Well concentration (uM) | Avg % increase of HA yield | Average % increase of NP signal |
|---|---|---|---|
| Statin 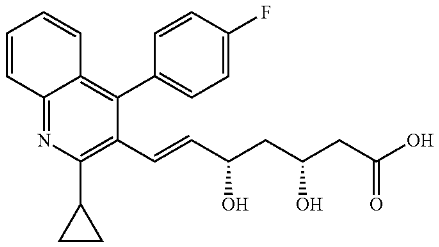 | 0.08 | 67.38 | 91.92 |
| | 0.16 | 76.13 | 90.98 |
| | 0.31 | 74.03 | 90.22 |
| | 0.63 | 83.20 | 69.05 |
| | 1.25 | 68.34 | 65.28 |
| | 2.50 | 60.97 | 63.19 |
| | 5.00 | 16.25 | 29.27 |
| | 10.00 | −12.34 | −11.44 |
| Benziothiazole 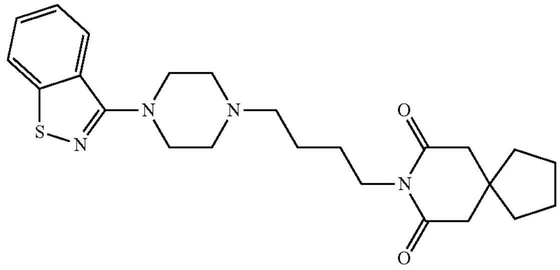 | 0.08 | 26.67 | 5.84 |
| | 0.16 | 25.97 | 14.84 |
| | 0.31 | 22.62 | 26.68 |
| | 0.63 | 28.39 | 26.79 |
| | 1.25 | 34.15 | 47.70 |
| | 2.50 | 47.99 | 53.27 |
| | 5.00 | 88.58 | 78.01 |
| | 10.00 | 124.63 | 99.38 |
| Benzpyrans 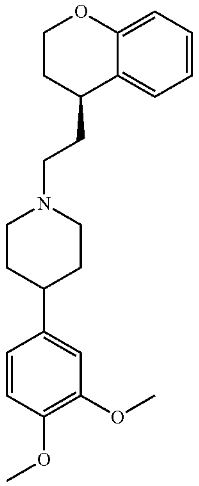 | 0.08 | 41.56 | 49.66 |
| | 0.16 | 50.02 | 46.81 |
| | 0.31 | 49.52 | 47.83 |
| | 0.63 | 64.30 | 69.11 |
| | 1.25 | 60.09 | 76.67 |
| | 2.50 | 80.12 | 123.05 |
| | 5.00 | 78.27 | 97.64 |
| | 10.00 | 107.06 | 91.94 |

TABLE 2-continued

| Compound | Well concentration (uM) | Avg % increase of HA yield | Average % increase of NP signal |
|---|---|---|---|
| Dimethoxyphenyl-piperidinemethanols 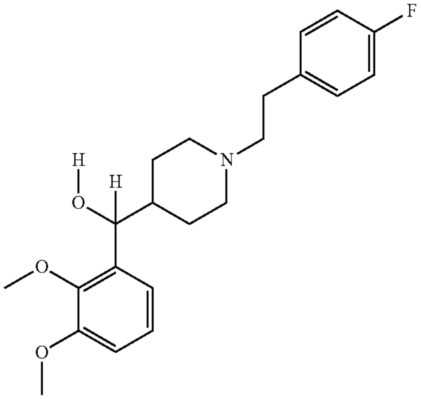 | 0.08 | 40.64 | 26.88 |
| | 0.16 | 49.76 | 42.89 |
| | 0.31 | 46.61 | 51.23 |
| | 0.63 | 57.07 | 70.43 |
| | 1.25 | 62.46 | 67.14 |
| | 2.50 | 64.47 | 96.13 |
| | 5.00 | 67.07 | 124.66 |
| | 10.00 | 97.73 | 148.67 |

Example 2—Confirmation Studies on Lead Compounds

Figure 2:
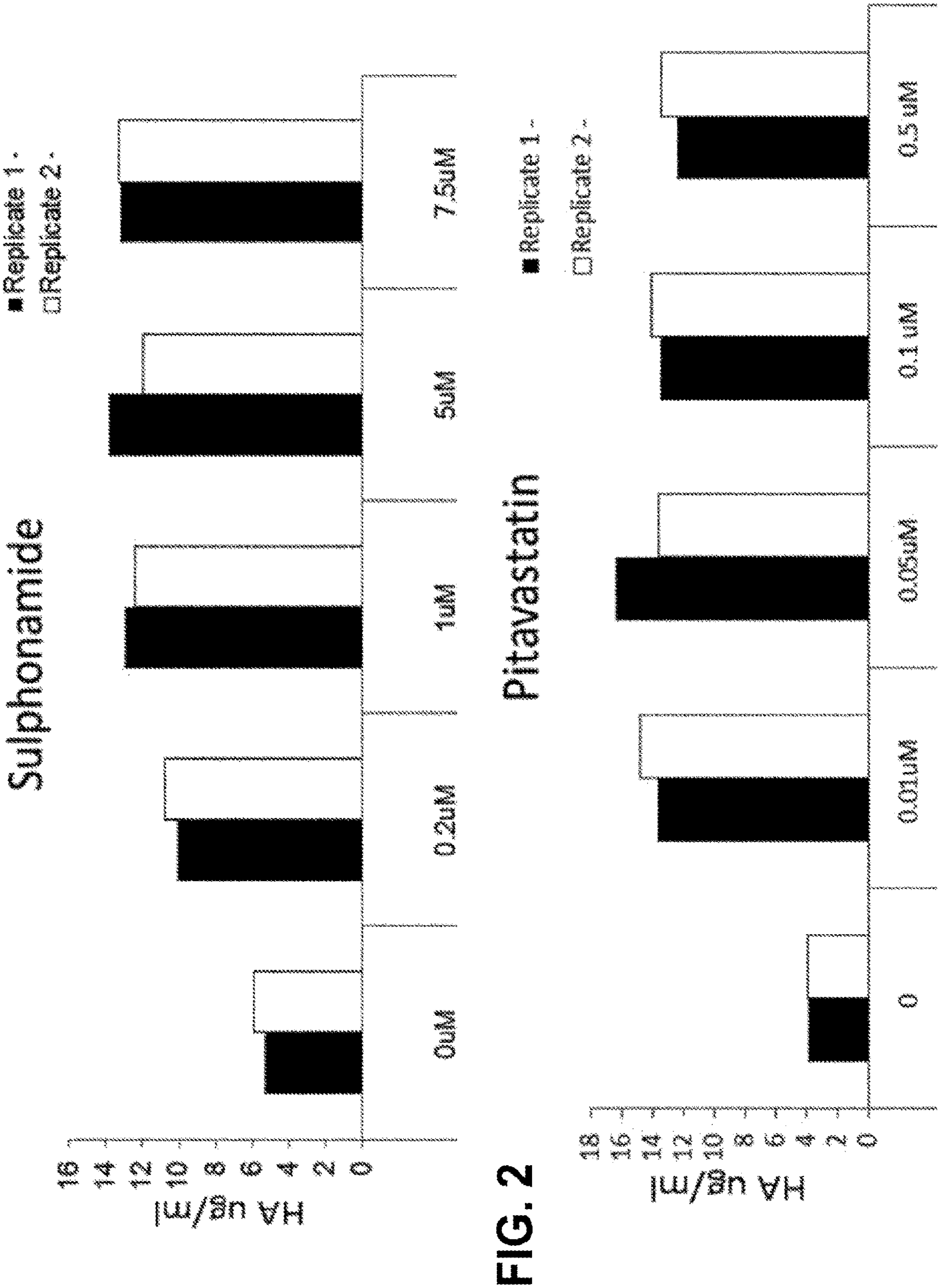
FIG. 2 shows dose response enhancement of HA yield as measured by ELISA with an H3N2 strain IVR-165 at MOI=$10^{-4}$ at 60 hours post infection (hpi).

The 2 best compounds selected were subjected to confirmation tests performed in 10 ml suspension cultures using multiple flu strains and subtypes. After virus incubation, the supernatant was harvested and virus/HA yield were quantified. HA yield was measured by ELISA. Infectious particles were measured by NP-based focus formation assay (FFA). Virus particles were measured by qPCR quantitation of nucleic acid sequences. The yield in total viral particles, infectious particles and HA measured in the culture supernatant showed similar increase using a sulphonamide analog (hereafter "sulphonamide analog") or pitavastatin compared to control. However, pitavastatin increased the yield at substantially lower concentration than the sulphonamide analog. The results of a dose-response enhancement study for the H3N2 strain IVR-165 are shown in FIG. 2. Pitavastatin led to a 3 fold increase in HA yield even at concentrations as low as 0.05 or even 0.01 μM.

Example 3—Test Lead Compounds with Various Influenza Virus Strains

To study the scope of influenza strains which could be affected by treatment with compounds herein, MDCK cells were infected with different influenza virus strains and subtypes using 1 μM sulphonamide or 0.05 μM pitavastatin. Virus infection was conducted at either an MOI of $10^{-3}$ or $10^{-4}$ for approximately 60 hours at 34° C.

I. Influenza A

Figure 3:
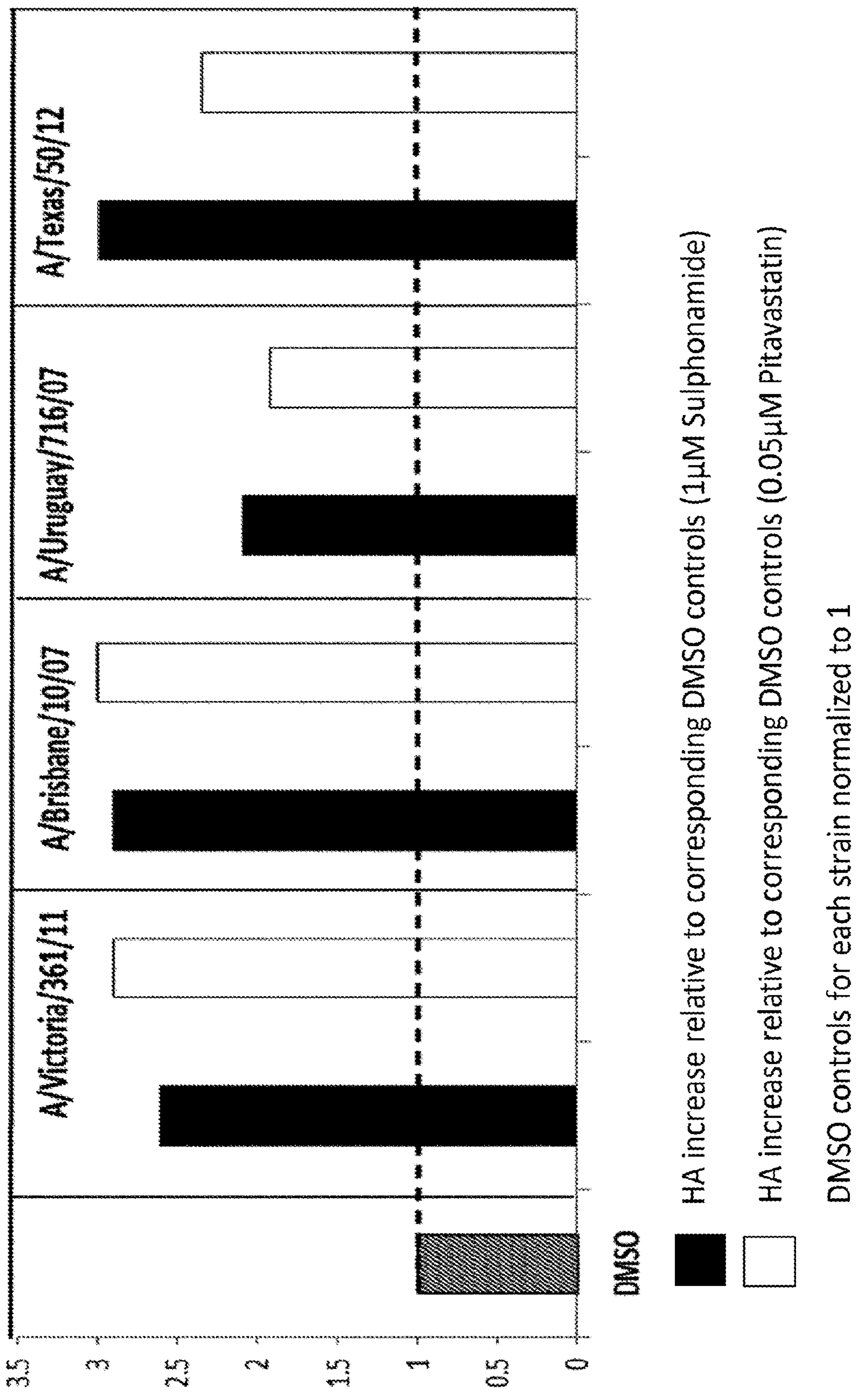
FIG. 3 shows a bar graph illustrating enhanced HA yield obtained from multiple influenza Subtype A H3N2 strains using 1 μM sulphonamide or 0.05 μM pitavastatin. 2-3 fold HA yield was typically observed in these studies.

A sample was obtained from the supernatant at 60 hours post virus inoculation for mechanism of action studies to identify gene expression or protein expression. As shown in FIG. 3, significant HA yield enhancement was observed for multiple influenza strains such as influenza subtype A H1N1 (strains A/Brisbane/10/10 and A/Solomon ×145), influenza subtype A H3N2 (strains A/Victoria/361/11, A/Brisbane/10/07, A/Uruguay/716/07 and A/Texas/50/12)

II. Influenza subtype B

Figure 4:
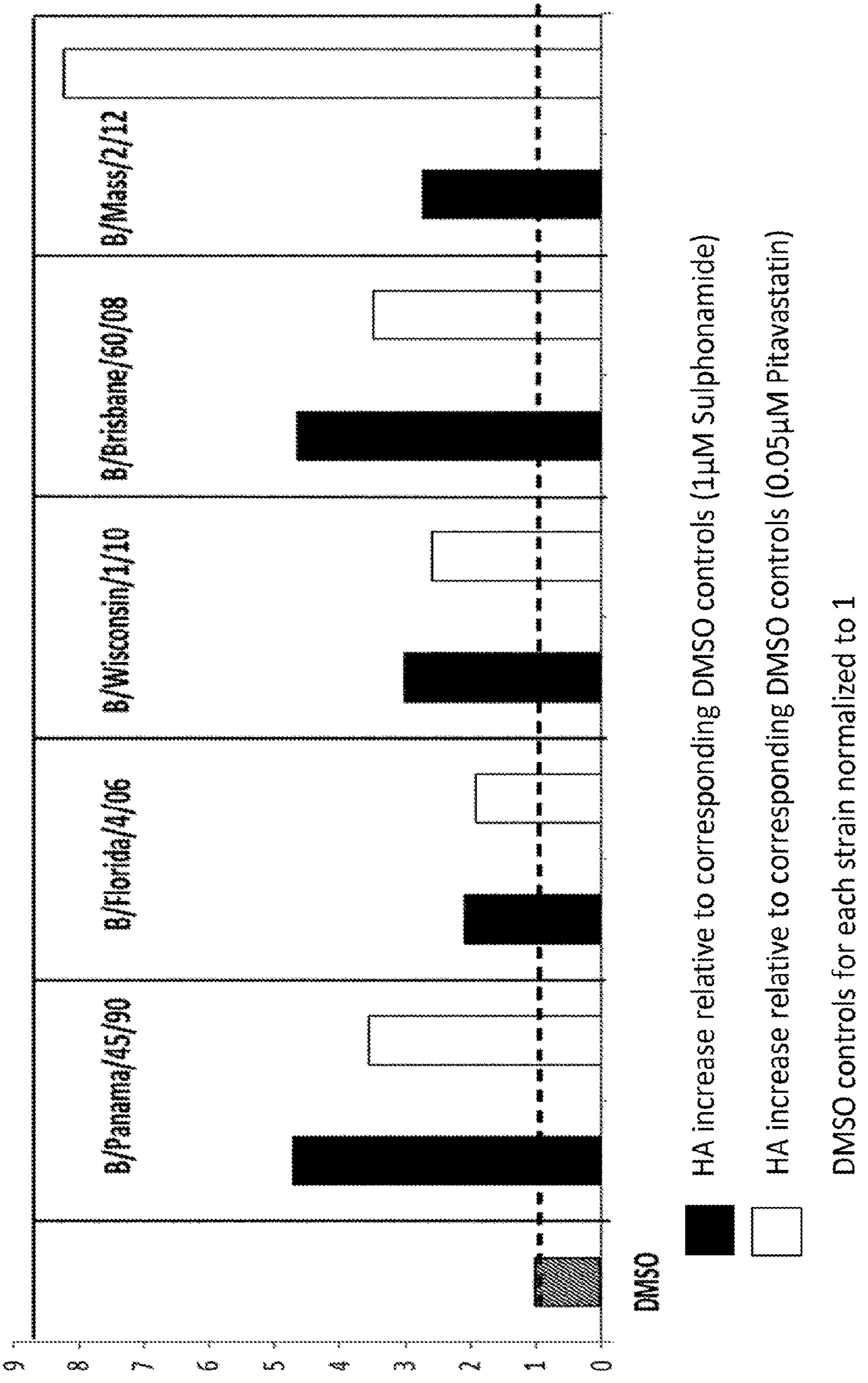
FIG. 4 shows a bar graph demonstrating enhanced HA yield obtained from multiple Subtype B strains for 1 μM sulphonamide and 0.05 μM pitavastatin. At least 2-10 fold HA yield was typically observed depending on strain.

Chemical agents used in the invention have significant effect on production of Influenza subtype B virus/protein. As shown in FIG. 4 sulphonamide and pitavastatin produced at least a 2-fold increase in HA relative to control in multiple strains of influenza subtype B (strain B/Panama/45/90, B/Florida/4/06, B/Wisconsin/1/10, B/Brisbane/60/08 and B/Mass/2/12).

This data shows that the effect of the compounds is not restricted to a particular viral strain.

Example 4—Mechanism of Action and Cell Viability Studies

Mechanism of action studies were conducted to determine the effect of chemical agents on different stages of the viral life cycle. Time of addition was studied at −32 hours, −24 hours, −8 hours, −1 hour, +2 hours, +4 hours, +6 hours from infection of the cells. In a single cycle virus infection study, cells were incubated with virus at an MOI of 5, on ice, for 1 hr to allow virus attachment. After 1 hr, unattached viruses were washed away, cells were moved to 34° C. to allow viruses to fuse and enter cells. 1.0 uM sulphonamide or 0.05 uM pitavastatin were added at different time points (T=0, 2, 4, 6 hr) after a washing step. The sulphonamide analog and pitavastatin appeared stable up to 32 hours in culture prior to infection with influenza H3N2 strain IVR-165 (A/Victoria/361/2011). HA yield decreased from about 20 μg/ml to about 5 μg/ml occurred for the sulphonamide analog 6 hours post infection and about 20 μg/ml to about 5 μg/ml for pitavastatin 2 hours post infection. The results suggest HA yield is dependent on time of addition after virus infection which may be as a result of the effect of the specific agent and specific stage of viral life cycle Cell viability assays were performed using MDCK cells treated with 1 uM sulphonamide or DMSO control. Cell viability was monitored over time up to 60 hrs using a VI-CELL machine (Beckman Coulter)(cell viability measured based on trypan blue exclusion). The sulphonamide analog used herein is not a marketed drug, therefore toxicity was conducted to identify cell viability over the course of incubation at the highest tested concentration of 10 μM and 60 hours of contact. Neither sulphonamide nor pitavastatin had a negative impact on cell viability. At least 91% viability is detected in cells treated with sulphonamide.

Example 5—Mass Spectrometry Analysis

Figure 6A:
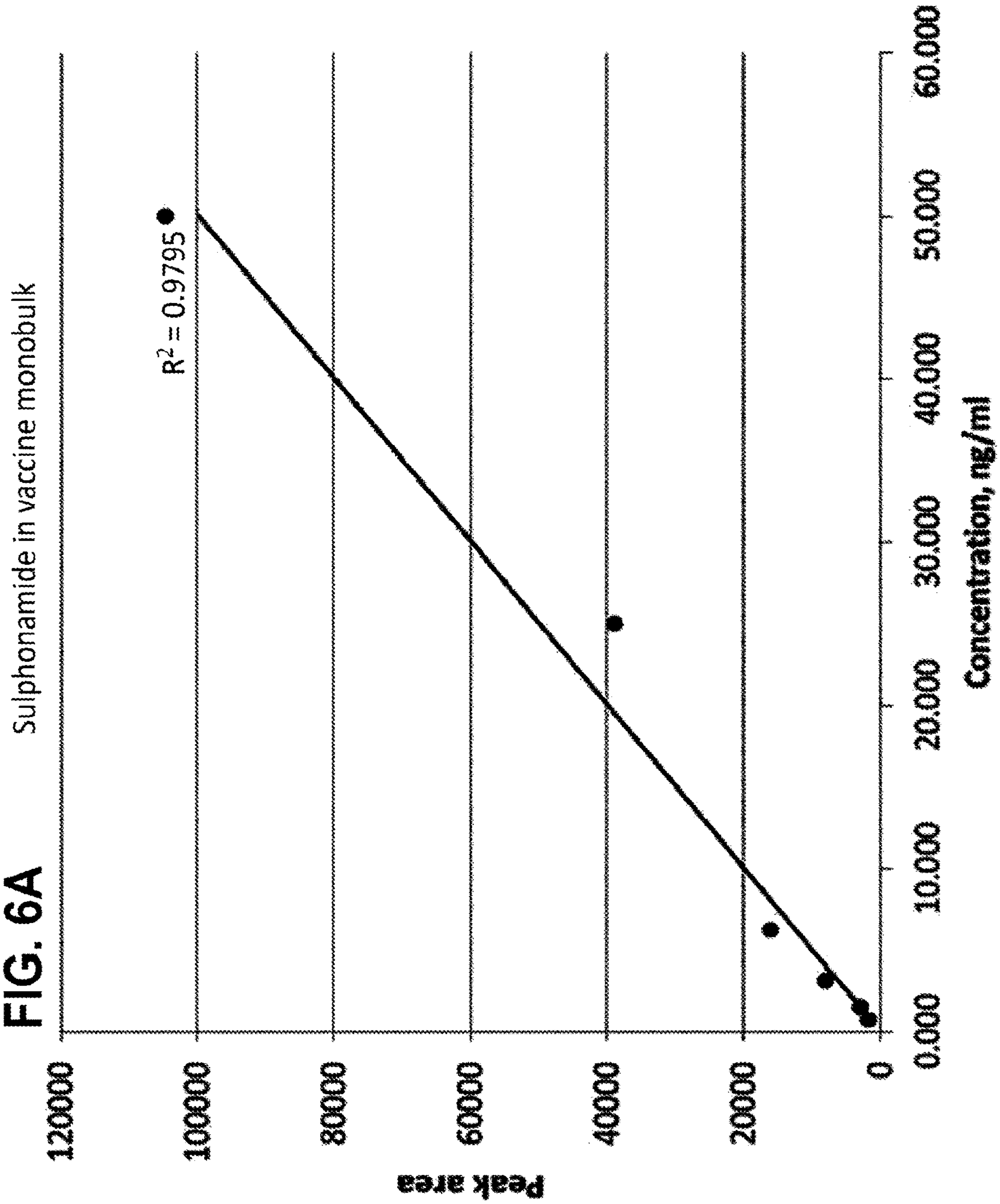
Figure 6B:
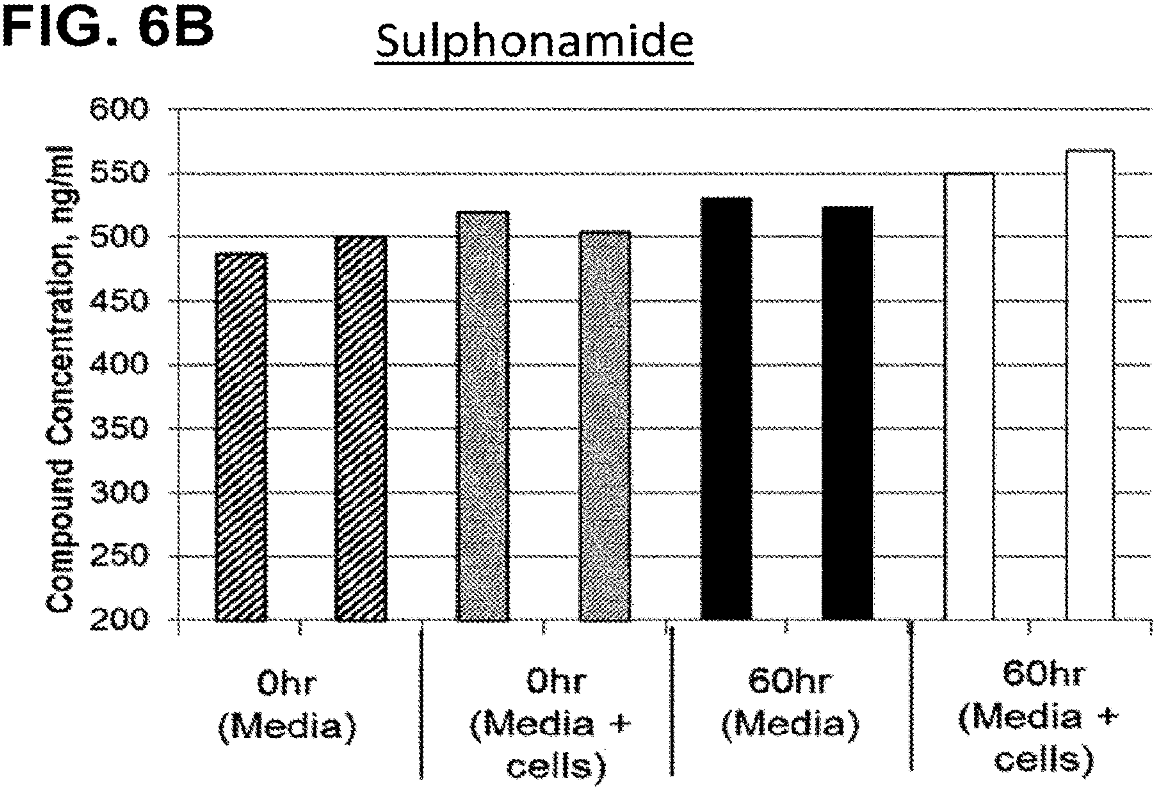
Figure 6B:
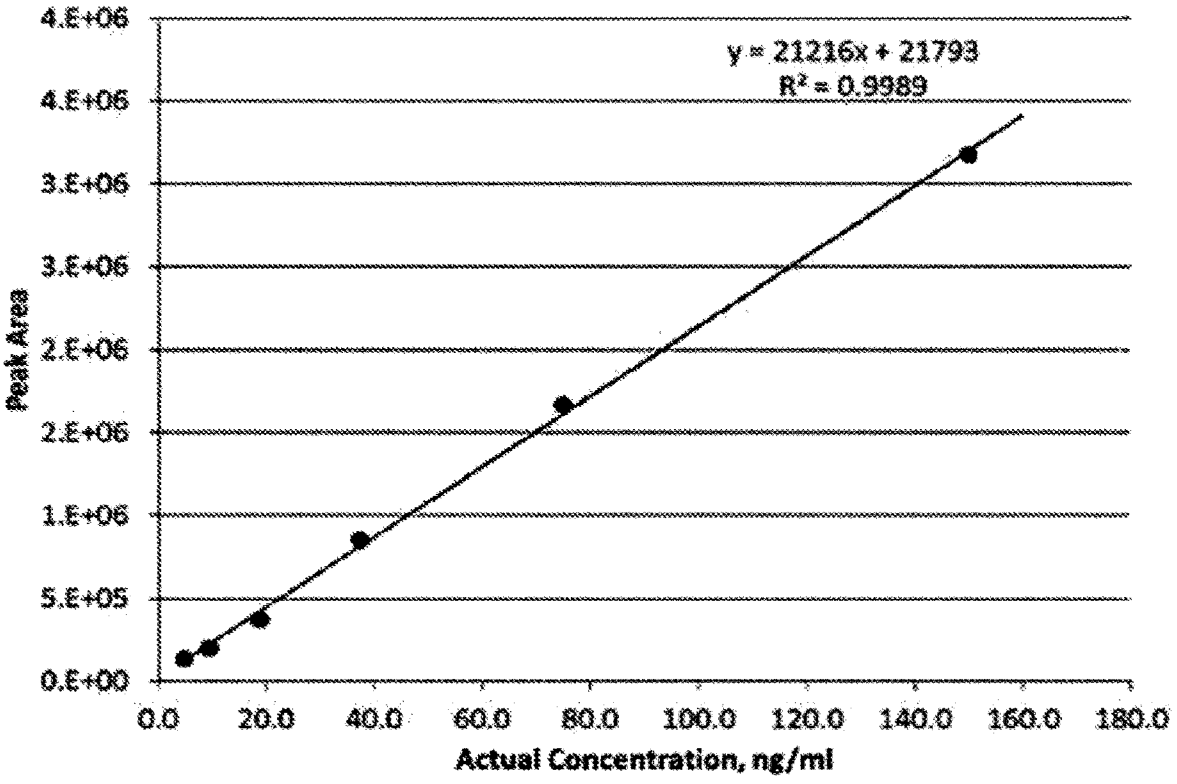

A liquid chromatography-mass spectrometry (LC-MS) assay using a triple quadrupole mass spectrometer operated in Multiple Reaction Monitoring (MRM) mode was developed to monitor compound presence/clearance in the cell culture supernatant and after a virus purification process by sucrose-density gradient. An estimate for the limit of detection (LOD) was determined by serial dilution of compounds in vaccine monobulk fluid and then performing a serial dilution of compounds using monobulk down to a concentration of 1 ng/ml. Prior to analysis acetonitrile was added (50% v/v) to all samples and samples were centrifuged for 5 minutes on benchtop centrifuge to remove protein precipitate. For both 1 ng/ml samples of sulphonamide and pitavastatin the signal to noise was estimated to be over 100 (over 400 in the case of sulphonamide). From the observed signal to noise level at 1 ng/ml concentration, the limit of detection is conservatively estimated to be below 0.5 ng/ml and the limit of quantitation estimated to about 5 ng/ml (FIG. 6A). The calibration curves for each compound were consistently observed to be linear from 1 ng/ml to over 50 ng/ml with R2 values above 0.95 (FIG. 6A, FIG. 6B). To determine if the compounds are metabolized or degraded in cell culture, compounds were spiked into media only or into media+MDCK cells. Supernatant from these spiked samples were taken at 0 and 60 hr for mass spec analysis. No loss of compounds was observed after 60 hrs (FIG. 6B). To determine if compounds could be cleared from the cell culture supernatant after a virus purification process, MDCK cells were infected with an influenza type A or B virus in the presence of compounds. After 60 hours, clarified cell culture supernatant was either (1) frozen at −80° C. for subsequent LC-MS analysis; or (2) subjected to a virus purification process involving sucrose-density gradient centrifugation and pelleting of virus particles. These "purified" samples were also tested by LC-MS to determine if the compounds get cleared during the purification process. Only trace amounts (below LOQ, and approaching LOD) were detected in these purified samples. The total amount (in ng) of compounds remaining after virus purification is less than 0.25% of the original input amount into the cell cultures (FIG. 6C).

Example 6—Studies in Scaled-Up Volumes

To identify whether HA yield was reproducible in larger test volumes, the two lead compounds were diluted in DMSO and applied at a concentration of 0.2 μM and 5 μM to either 10 ml or 60 ml sample volumes comprising MDCK cell cultures infected with H3N2 strain (IVR165) at MOI=$10^{-4}$ for 60 hours. Virus particles were measured by qPCR of RNAse-resistant RNA transcripts such as the flu M gene (see Ngaosuwankul et al, Virology Journal 7:75 (2010) doi: 10.1186/1743-422X-7-75). HA yield was normalized against control. Studies showed that a corresponding increase in HA yield was observed at both 10 ml and 60 ml cultures.

Figure 5A:
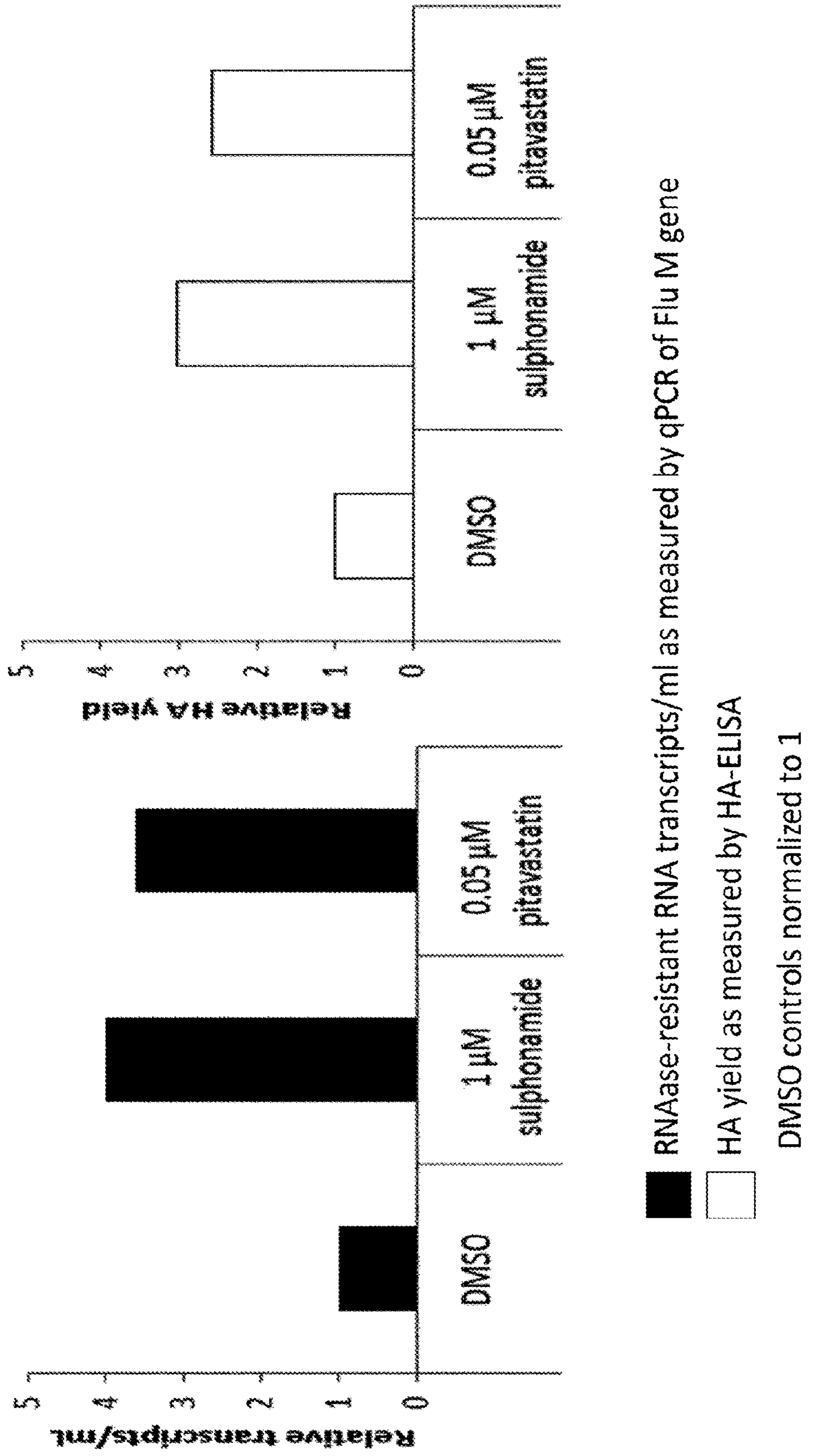
FIG. 5A and FIG. 5B show HA yield enhancement as measured by qPCR of RNAase-resistant flu M transcripts.
Figure 5B:
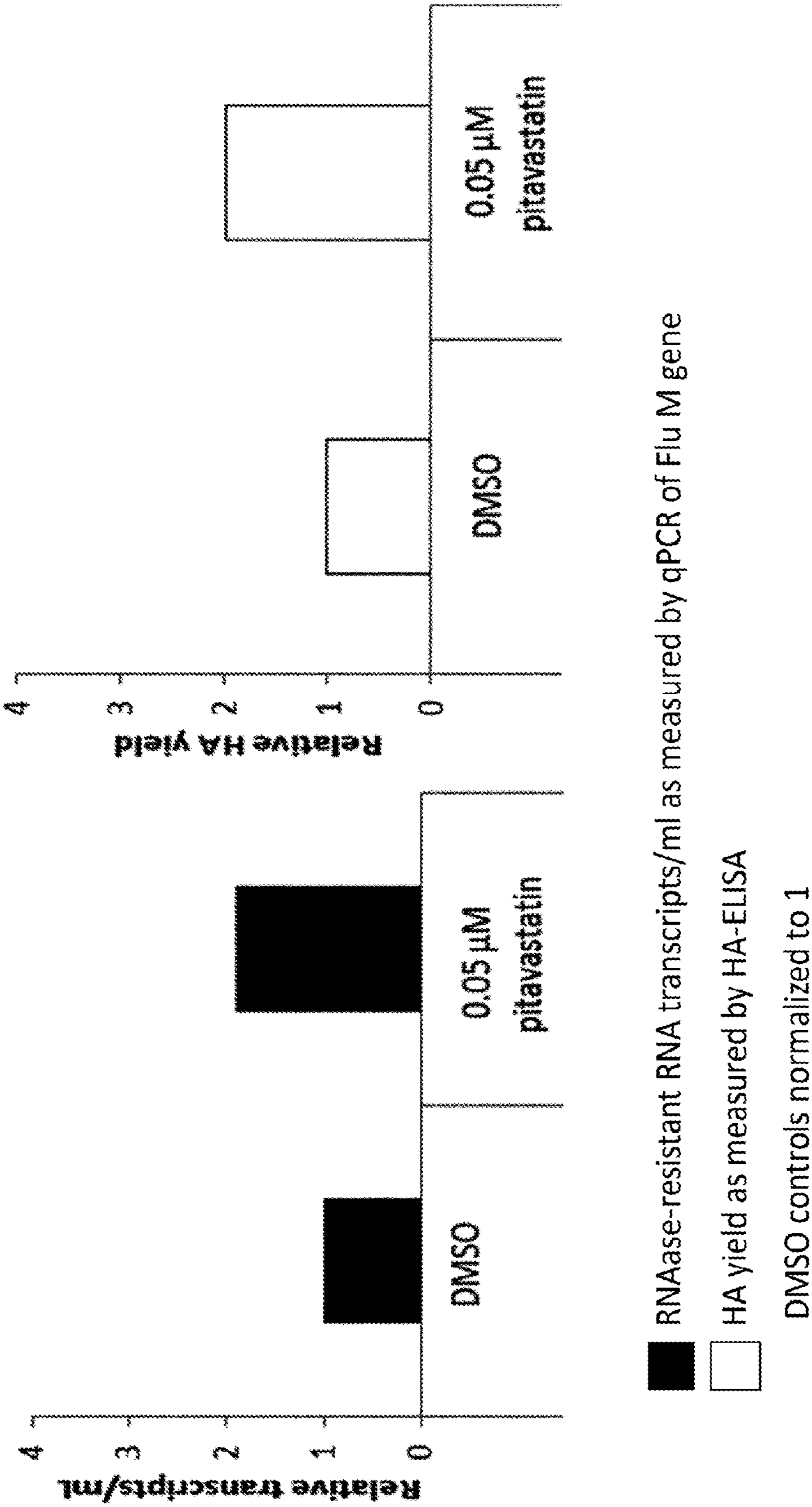

As shown in FIG. 5 results indicated that HA yield or particle increases correlated proportionately as confirmed by both ELISA and qPCR.

Figure 8:
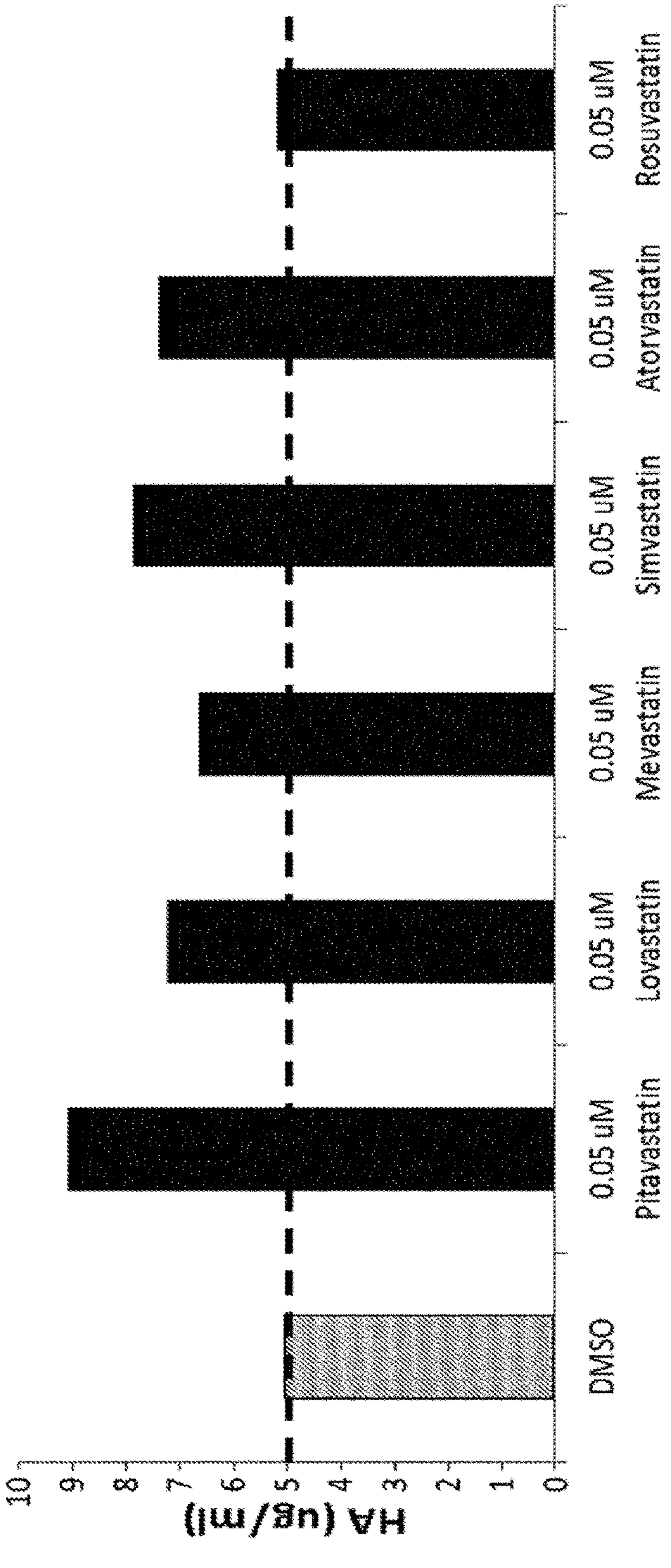
FIG. 8 shows a comparison of Subtype A/Texas X223A HA yield (μg/ml) of cells treated with commercially available statins.

Multiple analogs of a lead compound were tested for comparison against each other. Most of the analogs increased the yield of influenza at the concentration tested. However, for certain analogs, the concentration tested was not optimal. As shown in FIG. 8, statin analogs were tested for comparison of activity at 0.05 μM. Rosuvastatin was identified as an analog that did not produce the yield potential of comparative statins at 0.05 μM. However, alternative concentrations and experimental s conditions should be optimized to tailor the effects to a tested chemical agent, such as rosuvastatin.

Example 7—SAR Studies

Figure 7:
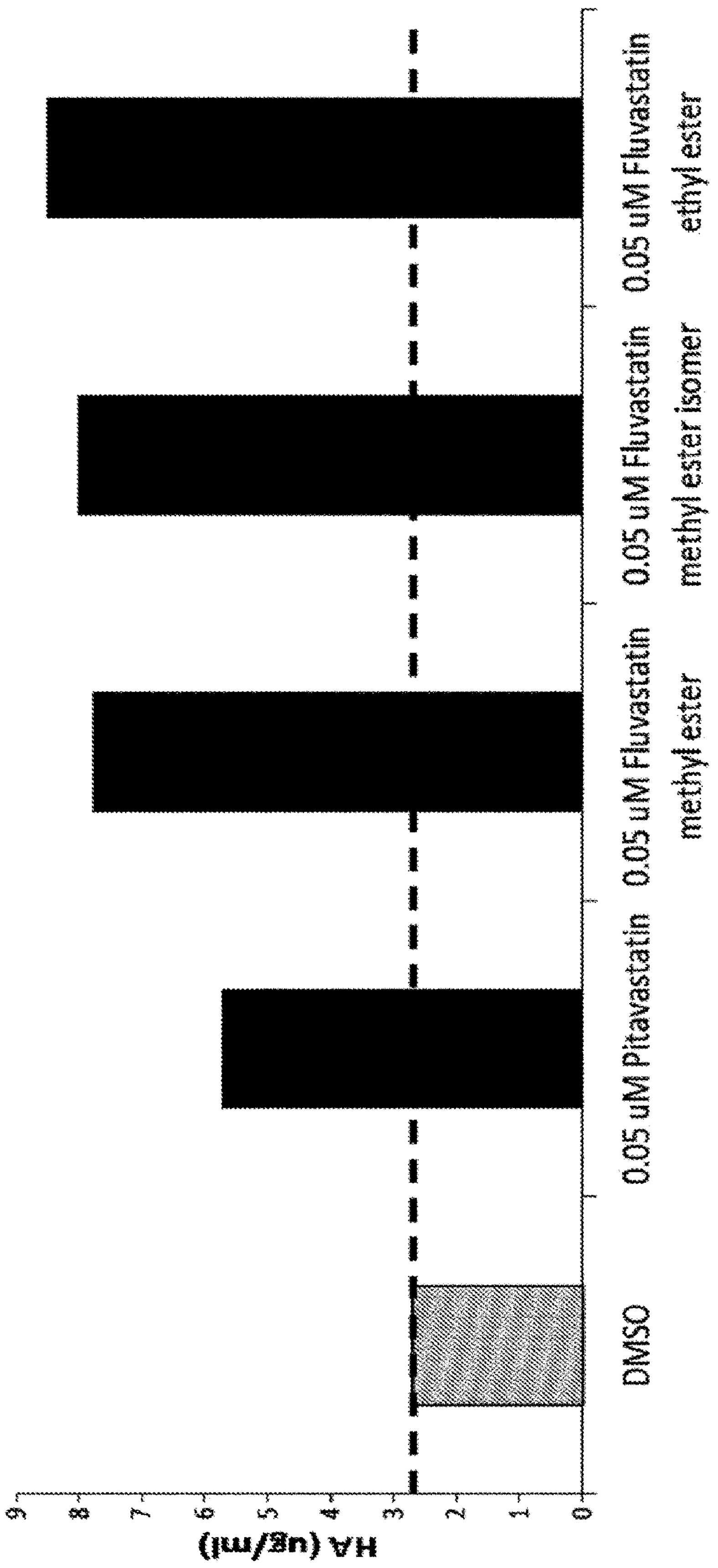
FIG. 7 shows Subtype AH3N2 HA yield (μg/ml) from cells treated with fluvastatin derivatives compared to pitavastatin and control at 0.05 μM.

A Structure Activity Relationship (SAR) study was conducted to identify analogues of the lead compounds. 88 sulfonamide analogue were identified of which 3 compounds were tested. One analogue led to a similar yield increase like the lead compound. 155 pitavastatin analogues were identified of which over 148 were tested. In addition, several other commercially available statins were tested (FIG. 8). Most of the tested analogues exhibited at least a 2-fold increase in yield of viral particles. In particular it was shown that (i) the lead compound pitavastatin was better than several other commercially available statins including simvastatin (FIG. 8), (ii) that fluvastatin and several fluvastatin derivatives like fluvastatinmethyl or -ethyl esters performed even better than pitavastatin (FIG. 7). Particularly preferred embodiments of statin analogs of the invention include the agents listed in Table 3 which present at least 2-fold increase in HA yield as measured by ELISA compared to control using DMSO treatment under conditions described above.

TABLE 3

| | HA-ELISA | |
|---|---|---|
| Compounds | HA fold increase over DMSO control | HA (ug/ml) |
| Statin-like analog 1 | 4.92 | 7.78 |
| Statin-like analog 2 | 4.71 | 8.01 |
| Statin-like analog 3 | 4.71 | 8.50 |
| Statin-like analog 4 | 4.32 | 7.34 |
| Statin-like analog 5 | 4.14 | 6.89 |
| Statin-like analog 6 | 3.56 | 6.56 |
| Statin-like analog 7 | 3.51 | 7.61 |
| Statin-like analog 8 | 3.43 | 6.47 |
| Statin-like analog 9 | 3.16 | 6.38 |
| Statin-like analog 10 | 2.99 | 6.56 |
| Statin-like analog 11 | 2.97 | 6.42 |
| Statin-like analog 12 | 2.92 | 9.29 |
| Statin-like analog 13 | 2.89 | 8.63 |
| Statin-like analog 14 | 2.83 | 7.34 |
| Statin-like analog 15 | 2.73 | 19.69 |
| Statin-like analog 16 | 2.59 | 19.69 |
| Statin-like analog 17 | 2.57 | 14.34 |
| Statin-like analog 18 | 2.56 | 17.31 |
| Statin-like analog 19 | 2.54 | 12.51 |
| Statin-like analog 20 | 2.53 | 7.72 |
| Statin-like analog 21 | 2.43 | 7.19 |
| Statin-like analog 22 | 2.40 | 9.28 |
| Statin-like analog 23 | 2.24 | 10.56 |
| Statin-like analog 24 | 2.13 | 8.44 |
| Statin-like analog 25 | 2.09 | 8.55 |

Example 8—Elucidation of Signaling Pathway

In our chemical additive approach to enhancing biologic production in cell culture, mechanisms of action underlining the observed enhancing effects were assessed. To identify and characterize chemical additives for the application, flu vaccine production in our MDCK 33016PF cells was used as a working model and was used to determine the feasibility of this approach in manufacturing such products. To that end, a top compound that enhances HA yield in multiple strains and subtypes of influenza by at least 2-fold, BYF589 (Compound G in Table 4) was selected for detailed evaluation. In order to determine if HA yield enhancement by BYF589 is a consequence of HMGCR inhibition, studies were conducted to better understand its mode of action in the system. To examine the Mevalonate (MEV) pathway, specific enzyme inhibitors were utilized (illustrated in FIG. 9A). These enzyme inhibitors selectively target specific branches of the MEV pathway, providing a better path forward for BYF mechanism of action ("MOA") determination.

Possible effects of BYF589 as well as various enzyme inhibitors of the pathway on the cell viability and total cellular cholesterol levels were examined. Tested samples included DMSO, BYF589 (1 μM), MEV (100 μM), FTI (0.5 μM), ZA (1 μM) and GTI (0.5 μM). After 24 hours of treatment, no negative effect on cell viability as measured by cell titer glow was detected.

Free cholesterol is oxidized by cholesterol oxidase to form a cholesterol ketone and $H_2O_2$, which then reacts with Amplex Red+HRP to produce the fluorescent product resorufin. For this portion of the experiment, HA yield and cellular cholesterol both normalized to DMSO were measured, HA enhancement correlates with lower cholesterol in cells treated with BYF, and this was dose-dependent, suggesting cholesterol content may be involved in enhancement. Alone, MEV has no effect on cellular cholesterol levels. When used in combination with BYF, MEV reduces HA yield enhancement but does not replenish cellular cholesterol levels, suggesting that cholesterol reduction alone is not sufficient to confer HA enhancement.

When the three inhibitors of the corresponding arms of the MEV pathway were used in various combinations, additive effects were observed, suggesting that multiple branches of the pathway are in fact involved in conferring the enhancement effect. The results are summarized in FIG. 9B. These results show that blocking all three arms of this pathway with specific enzyme inhibitor combination can mimic the HA enhancement effect of the compound. It was further confirmed that Biphosphonate, an inhibitor downstream of BYF589 action but upstream of the signaling branching point, can elicit similar dose-dependent enhancement of HA effect, albeit less robust than BYF589.

Example 9—Gene Expression Studies

Evidence in the literature suggests that statins can suppress IFN and IFN-mediated genes, such as IP10 (CxCL10). It was therefore examined whether flu HA enhancement may be linked to suppression of interferon (IFN) response by statins. Gene expression of IP10 and IFNB1 was measured following infection in the presence or absence of the BYF589 compound. Preliminary qRT-PCR data suggest delayed/suppressed induction of IFNb and IP10 in virus-infected MDCK cells in presence of BYF589. The observed delay time in both of the genes tested in the presence of the BYF589 compound was at least two hours, as compared to the timing of gene induction (measured at peak) in the absence of the BYF589 compound.

Example 10—Timing of Host Cell Treatment with an Enhancing Agent

To assess whether the two lead compounds (BYF589 and AFZ077) may work via a common pathway, each compound was added to a host cell culture at various times post-infection and effects on HA yields were measured 24 hours after infection. Results showed that when BYF589 was added at the time of virus infection (T=0), an approximately 4-fold increase in HA yield at 24 hours was achieved, as compared to control that was grown without the compound. However, when the BYF589 compound was added at later times (T=2, 4 or 6), no significant enhancement in HA yield was observed at 24 hours. In contrast, addition of AFZ077 at the time of infection (T=0), as well as at later times (T=2 & 4), an approximately 4-fold increase in HA yield was achieved at 24 hours post-infection; however, no significant increase was seen when AFZ077 was added at six hours post-infection (T=6). These results indicate that HA enhancement by the two compounds is dependent on time-of-addition into infected host cell cultures. Moreover, based on the temporal differences in the effects of each compound, it is likely that the two compounds target different stages of the virus life cycle. Additionally or alternatively, the two compounds may regulate different pathways of the host cells.

Example 11—Mini-Bioreactor Side-By-Side Comparison

The two lead compounds were further tested in the commercially available small-scale bioreactor system, ambr15™ (TAP Biosystems). The ambr15 system mimics the characteristics of classical bioreactors at microscale (10-15 ml), controlled by an automated workstation, which enables the rapid evaluation of multiple bioreactor cultures at microscale.

To test both lead compounds were tested side-by-side under controlled conditions, with two infection media formulations (DM134 and CDM) and two flu strains, A/Victoria/361/2011 (IVR-165) (high-expressing) and B/Massachusetts/2/2012 (low-expressing). The infection parameters used in the experiment were as follows: seeding density was $1.0\times10^6$ cells/ml or $2.5\times10^6$ cells/mL; pH was 7.1+/−0.02 (pH control by dual control with 0.05N NaOH and $CO_2$ gas); DO was 50% (range 50-80%), controlled by $O_2$ gas; agitation was 1000 rpm (local control); temperature was 34.0° C., locally monitored with bioreactor controller probe; vessel type was Spargeless, extended temperature vessels; and, aeration rate during run was 1 mL/min.

Figure 10:
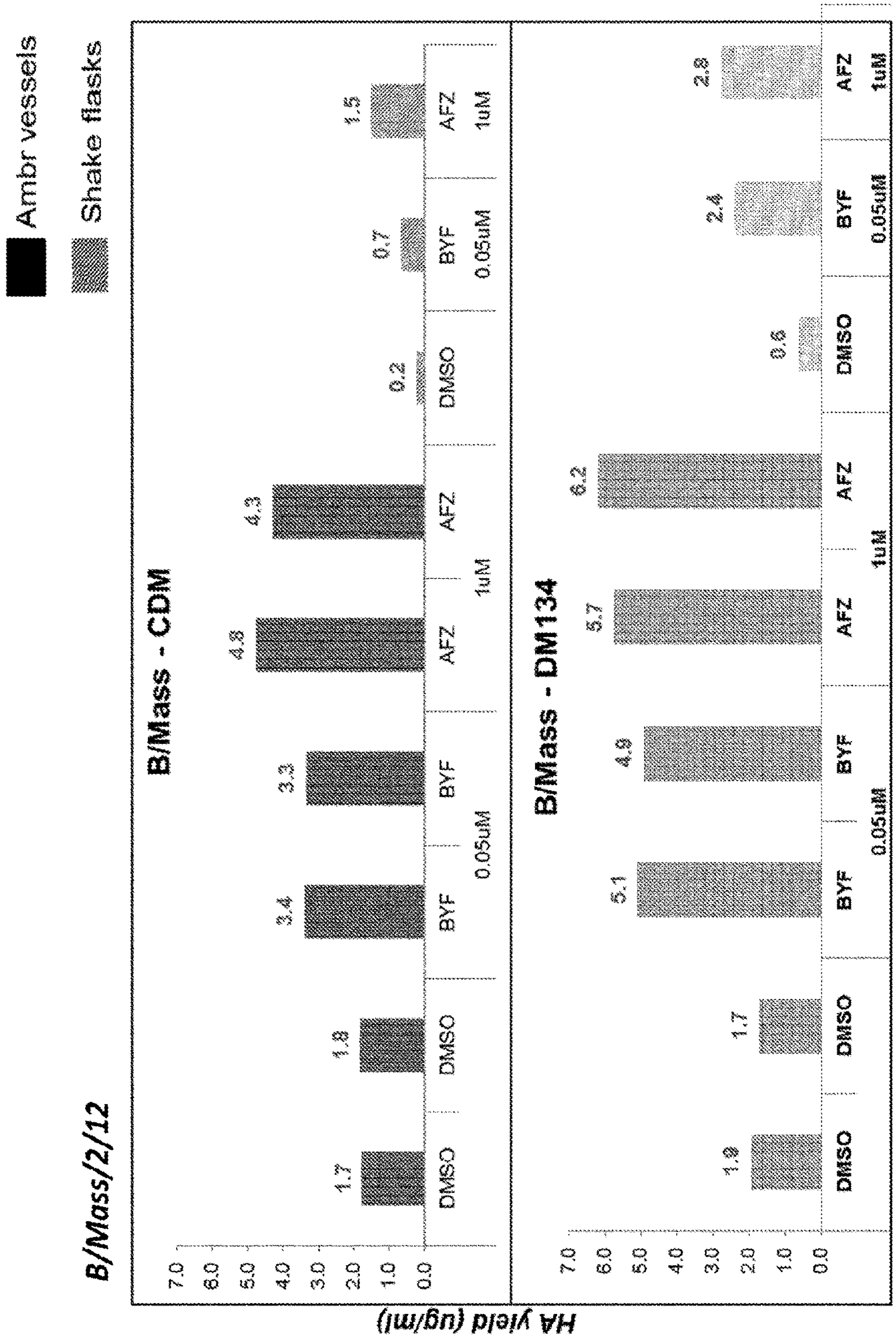
FIG. 10 provides a side-by-side comparison of HA yield in Ambr15 vs Shake flasks; both lead compounds enhanced yield for low expressing B/Mass/2/12 in both CDM and DM134 media in Ambr15.
Figure 11:
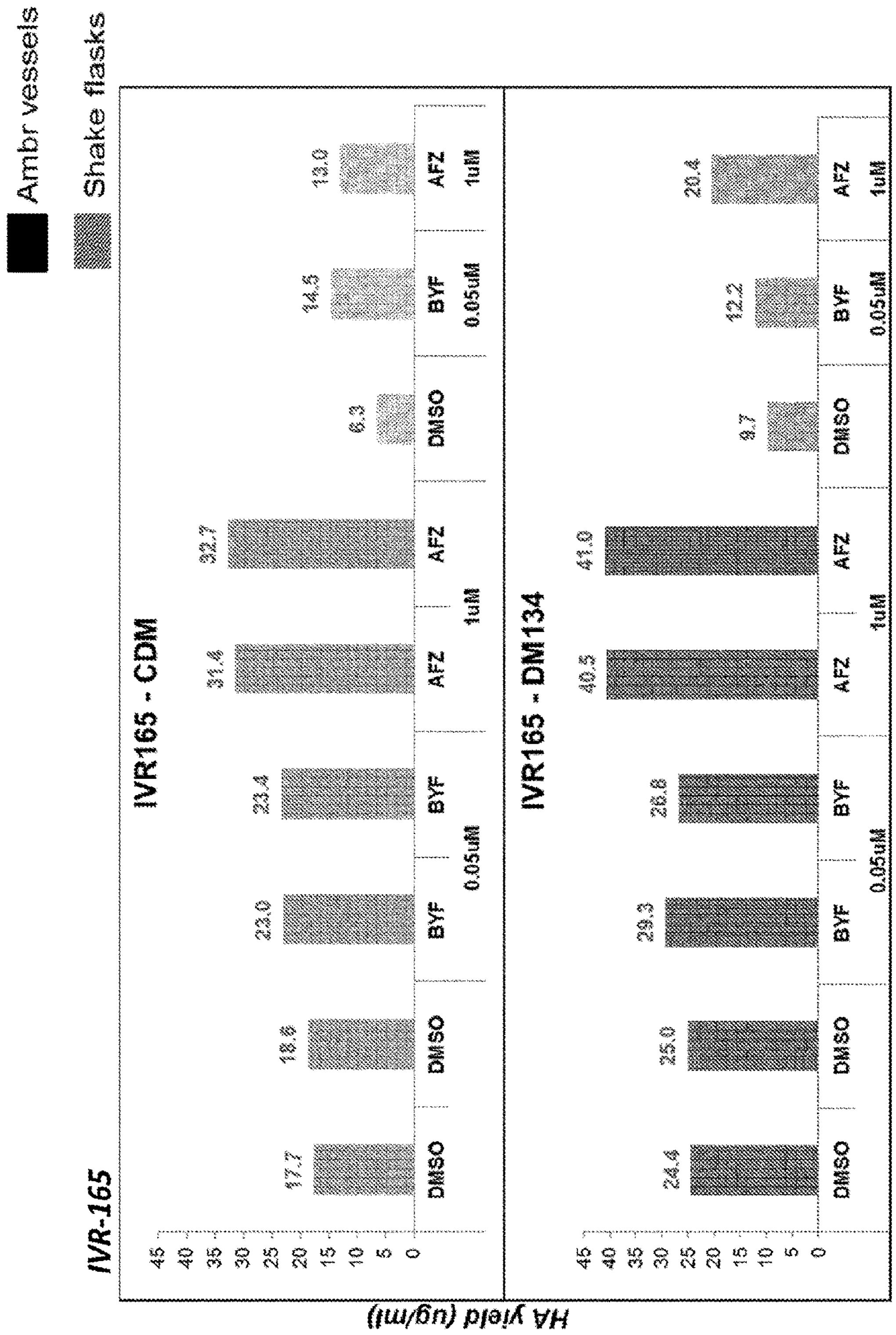
FIG. 11 provides a side-by-side comparison of HA yield in Ambr15 vs Shake flasks; Only AFZ077 enhanced yield for high-expressing A/Vic/361/11 (IVR165) in both CDM and DM134 media in Ambr15.
Figure 12:
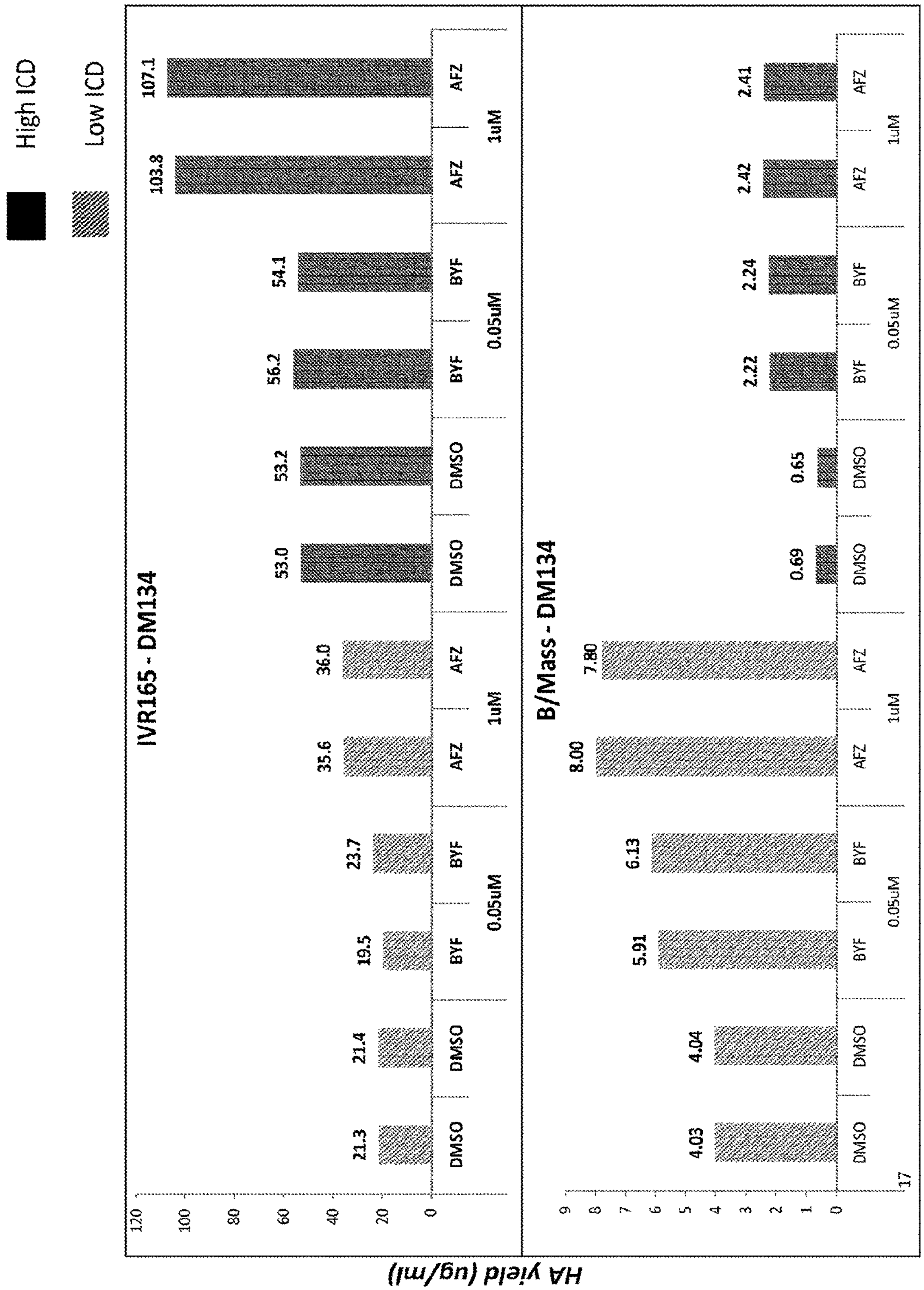
FIG. 12 provides HA yields in the A and B strains, with the two lead compounds at two concentrations, at two different cell densities (low and high ICDs), as measured by HA-ELISA.

Results from the ambr15 experiment are summarized in FIG. 10 and FIG. 11. Both lead compounds enhanced HA yield for the low-expressing B strain in both media. However, for the high-expressing A strain tested, AFZ077 achieved much greater enhancement in HA yield in both media tested. The quantification of HA was carried out by ELISA then was subsequently confirmed by HPLC. It was also shown that AFZ077 was able to boost HA yield in the DM134 medium with both low ($1\times10^6$ per mL) and high ($2.5\times10^6$ per mL) infection cell densities in this system. For the latter, by combining high ICD format with AFZ treatment, enhancement by AFZ077 resulted in ~4-fold higher yields over original yields, surpassing the original 2-fold target (FIG. 12). In summary, with the ambr15 system, AFZ077 boosts HA yield in the DM134 medium in shake flasks and 15 ml bioreactors for all strains tested so far. BYF589 boosts HA yield in the DM134 medium in shake flasks and 15 ml bioreactors for a poor-expressing flu B strain. Overall, greater enhancement effect seen for low-expressing strains. In addition, additive effects observed using AFZ077 and higher infection cell density.

Example 12—Large-Scale Bioreactor

Figure 13:
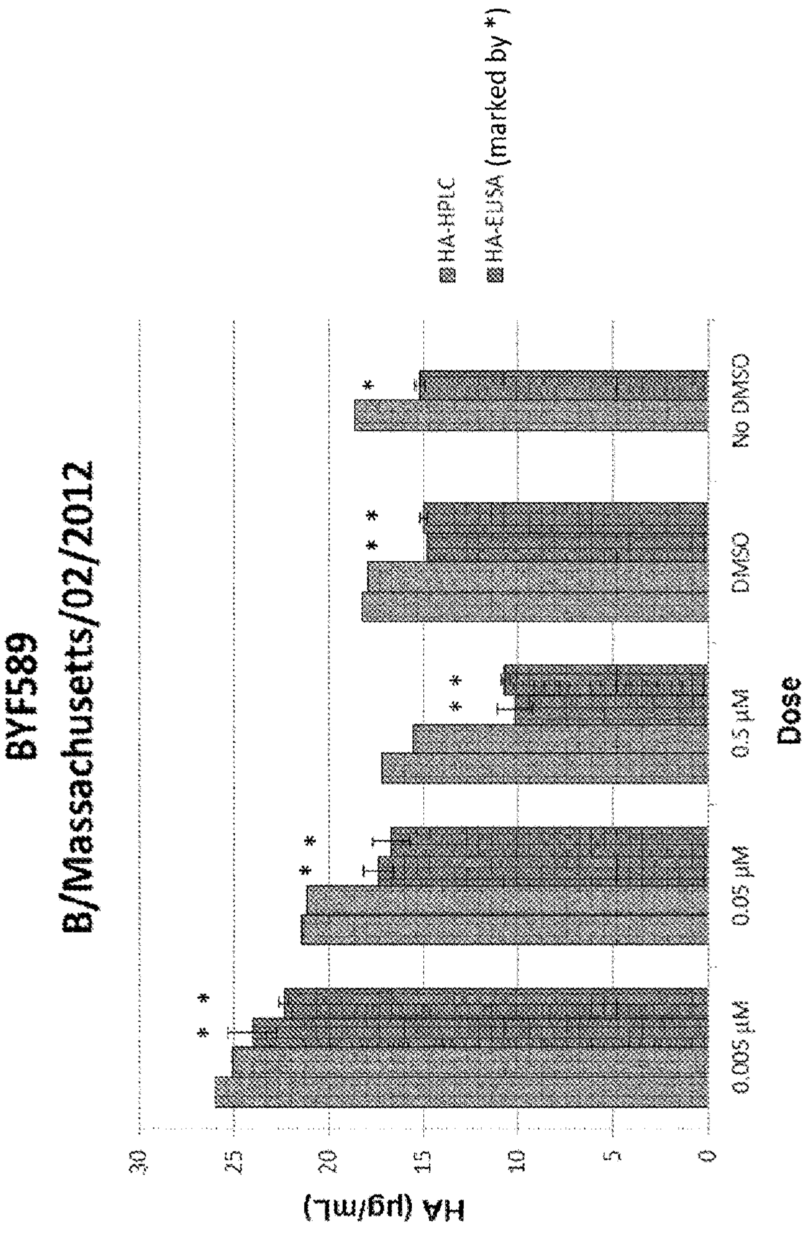
FIG. 13 provides a graph showing HA yields in the B strain tested with BYF589 at concentrations as indicated.
Figure 14:
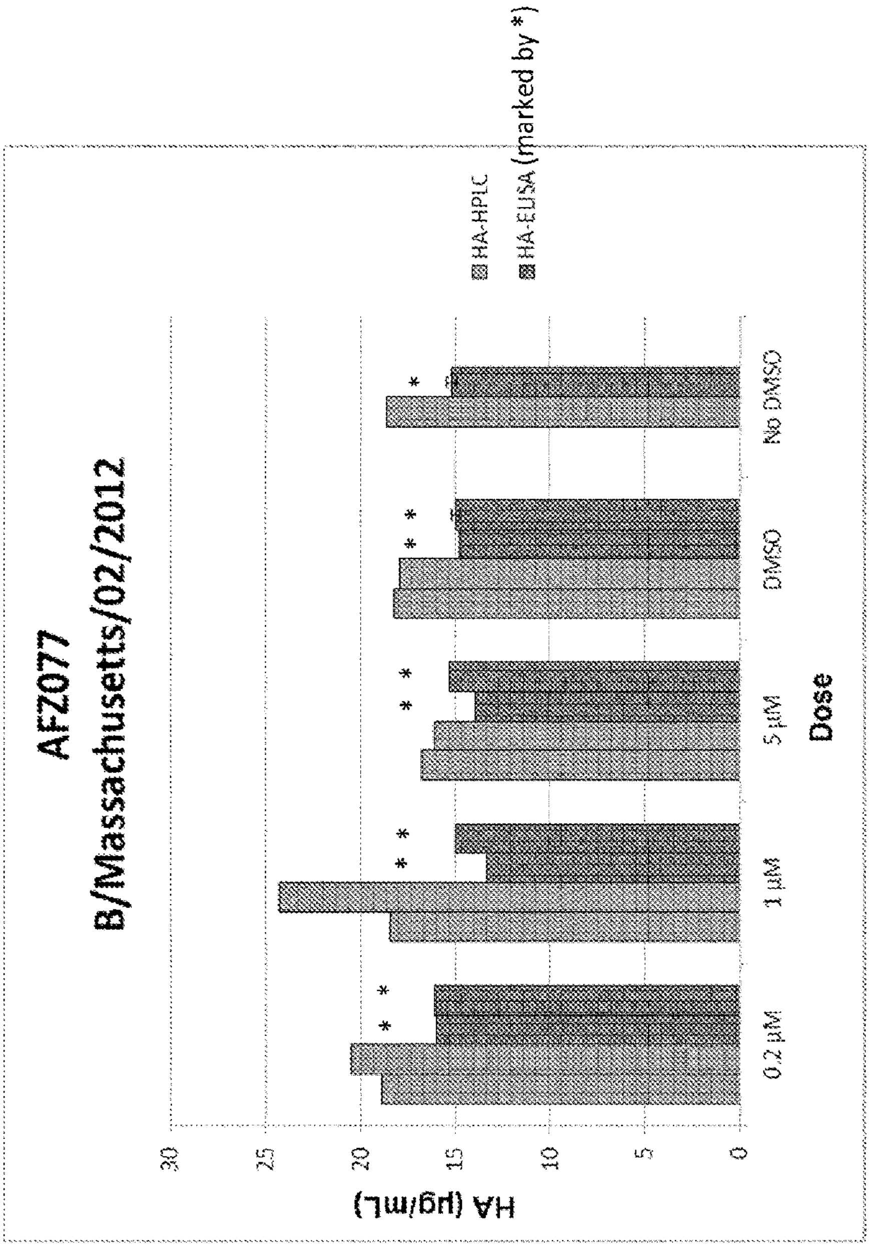
FIG. 14 provides a graph showing HA yields in the B strain tested with AFZ077 at concentrations as indicated.

In the previous studies, the AFZ077 compound was shown to boost HA yield in the DM134 medium in both Research shake flasks and 15 mL bioreactors. The results were confirmed using 3 different viruses (a high-, medium-, and poor-expressing strains). BYF589 was shown to boost HA yield in the DM134 medium in Research shake flasks and 15 mL bioreactors for a poor-expressing flu B strain, but not a high-expressing H3N2 strain. To confirm these findings in a larger-scale system, TD Ambr™ 250 mL bioreactors were employed. Both of the lead compounds (as well as DMSO alone as negative control, and, no compound/no DMSO as double-negative control) were tested with a high- and low-expressing strains to determine if the observed enhancement in the small-scale cultures can be reproduced in a larger-scale system. The following parameters were used: Spent DM134:Fresh PFM (1:3); Virus Strains were A/Victoria/361/2011 (IVR-165) and B/Massachusetts/02/2012; MOI was $10^{-5}$ for A/Victoria IVR-165 and $10^{-4}$ for B/Massachusetts; ICD: 2.0e6-3.0e6 cells/mL; N-1 Process: 1B (no Medium Exchange); and, Harvest Time was 65-72 hours post-infection. HA yields were measured by two methods: RP-HPLC and HA-ELISA. Data are provided in FIG. 13 and FIG. 14. FIG. 13 shows that BYF589 at 0.005 μM dose showed about 37% increase in yield over no DMSO control as determined by HA-HPLC. FIG. 14 shows that, under the particular conditions tested, AFZ077 appeared to yield no significant increase in HA yield over the controls at any of the doses tested for the B/Massachusetts strain in the ambr250 system. Note that the error bars represent one standard deviation from the mean, to illustrate variability of the HA-ELISA assay between assay repeats.

Example 13—Mechanistically-Related Compounds (Functional Equivalents)

Figure 15:
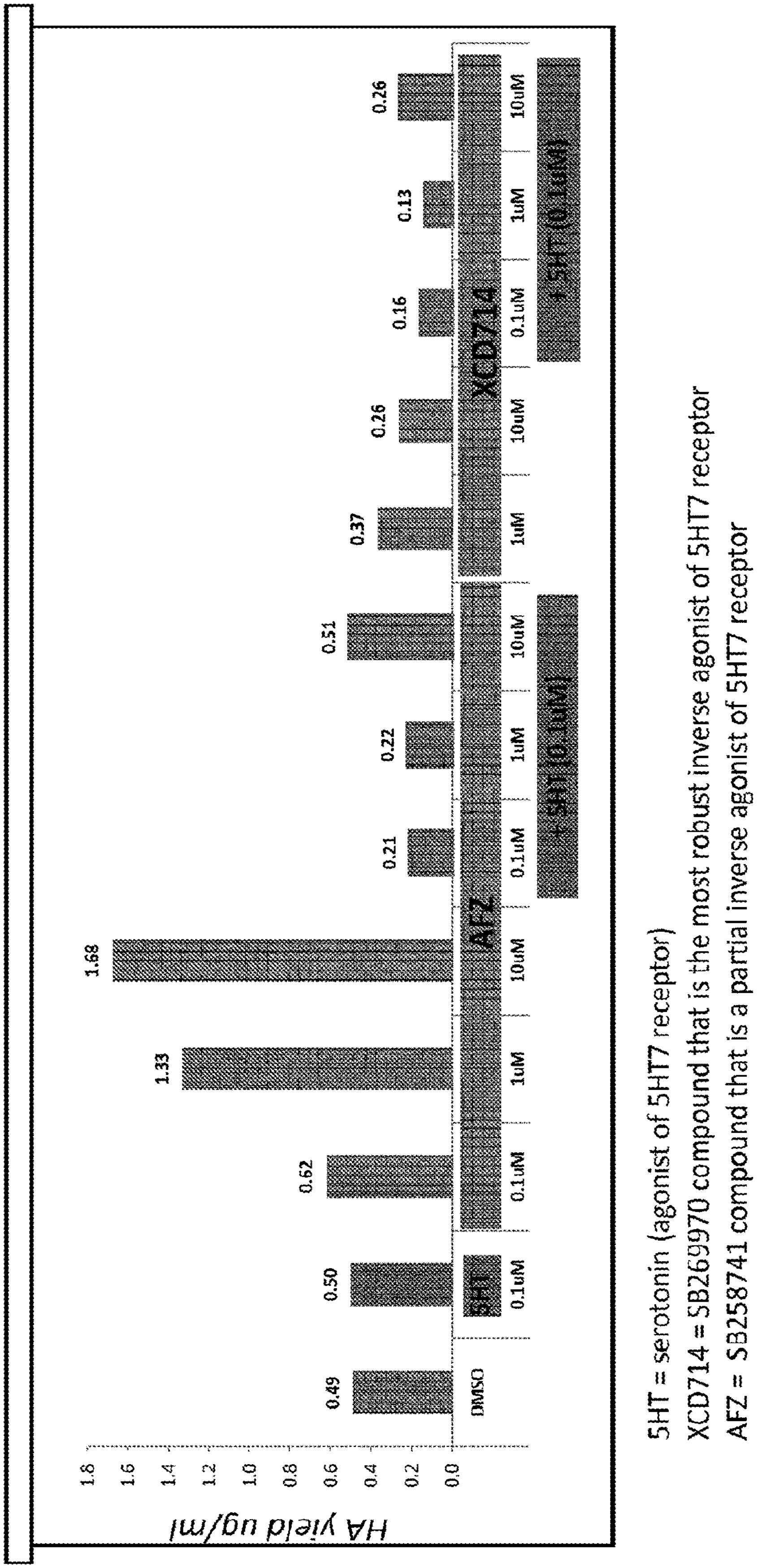
FIG. 15 provides a graph showing that Flu HA yield enhancement by AFZ077 is dependent on decreasing activity of the 5HT7 receptor. Flu B strain (B/Mass) in DM134 media; 65 hrs HA yield by ELISA (μg/ml).

It was found that the enhancing effect on the flu HA by AFZ077 is dependent on decreasing the activity of the 5HT7 receptor because the AFZ effects can be abrogated by adding serotonin (5HT) as ligand (see FIG. 15). This suggests that such effects are mediated by the receptor activity, indicating that other agents that can mediate the same or similar cellular effects may also enhance protein yield the way the lead compounds can. Studies based on Formula 8 (e.g., Compound E) were expanded to identify potential compounds that may share certain mechanisms of action, as summarized in Table 5 below.

TABLE 5

| COMPOUND | BINDING ACTIVITIES | STRUCTURE |
|---|---|---|
| Compound E (Reference compound) NVP-AFZ077 (SB-258741) | | 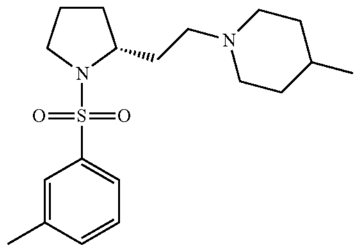 |
| Compound K NVP-AHL128 | | 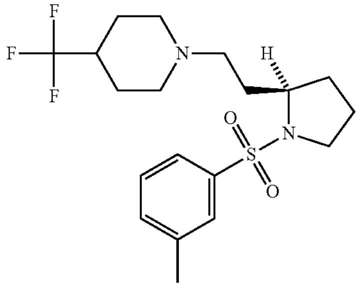 [SMILES: Cc1cccc(S(=O)(=O)N2CCC[C@@H]2CCN2CCC(C(F)(F)F)CC2)c1] |
| Compound L Clozapine | D2, 5-HT2A, 5-HT1A, 5-HT2C, 5-HT3, 5-HT6, 5-HT7, D1, D3, D4, a1, a2, M1, H1 | 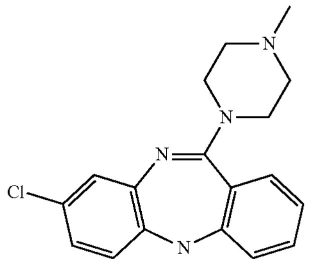 [SMILES: CN1CCN(C2=Nc3cc(Cl)ccc3Nc3ccccc32)CC1] |

TABLE 5-continued

| COMPOUND | BINDING ACTIVITIES | STRUCTURE |
|---|---|---|
| Compound M Risperidone | D2, 5-HT2A, 5-HT7, a1, a2 | 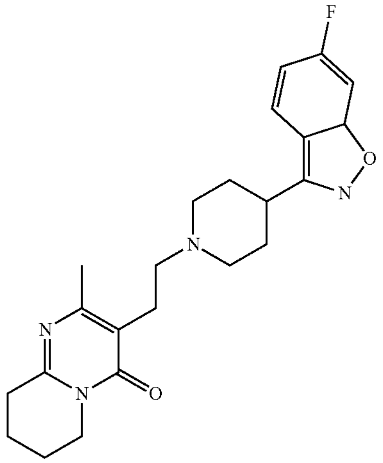 [SMILES: Cc1nc2n(c(=O)c1CCN1CCC(C3=C4C=CC(F)=CC4ON3)CC1)CCCC2] |
| Compound N NVP-XCD714 SB-269970 | | 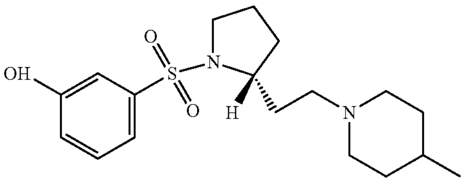 [SMILES: CC1CCN(CC[C@H]2CCCN2S(=O)(=O)c2cccc(O)c2)CC1] |
| Compound O Quetiapin | D2, 5-HT2A, 5-HT6, 5-HT7, a1, a2, H1 | 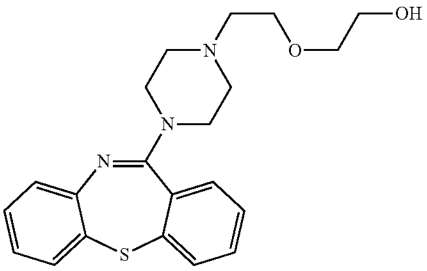 [SMILES: OCCOCCN1CCN(C2=Nc3ccccc3Sc3ccccc32)CC1] |
| Compound P Sumatripan | | 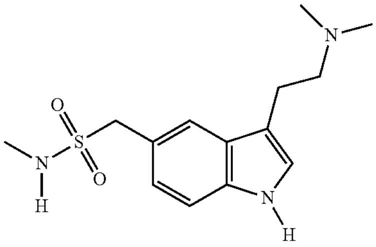 |
| Compound Q NVP-ARP341 | | 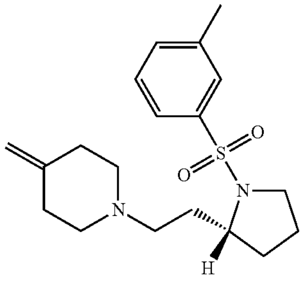 [SMILES: C=C1CCN(CC[C@H]2CCCN2S(=O)(=O)c2cccc(C)c2)CC1] |

Figure 16:
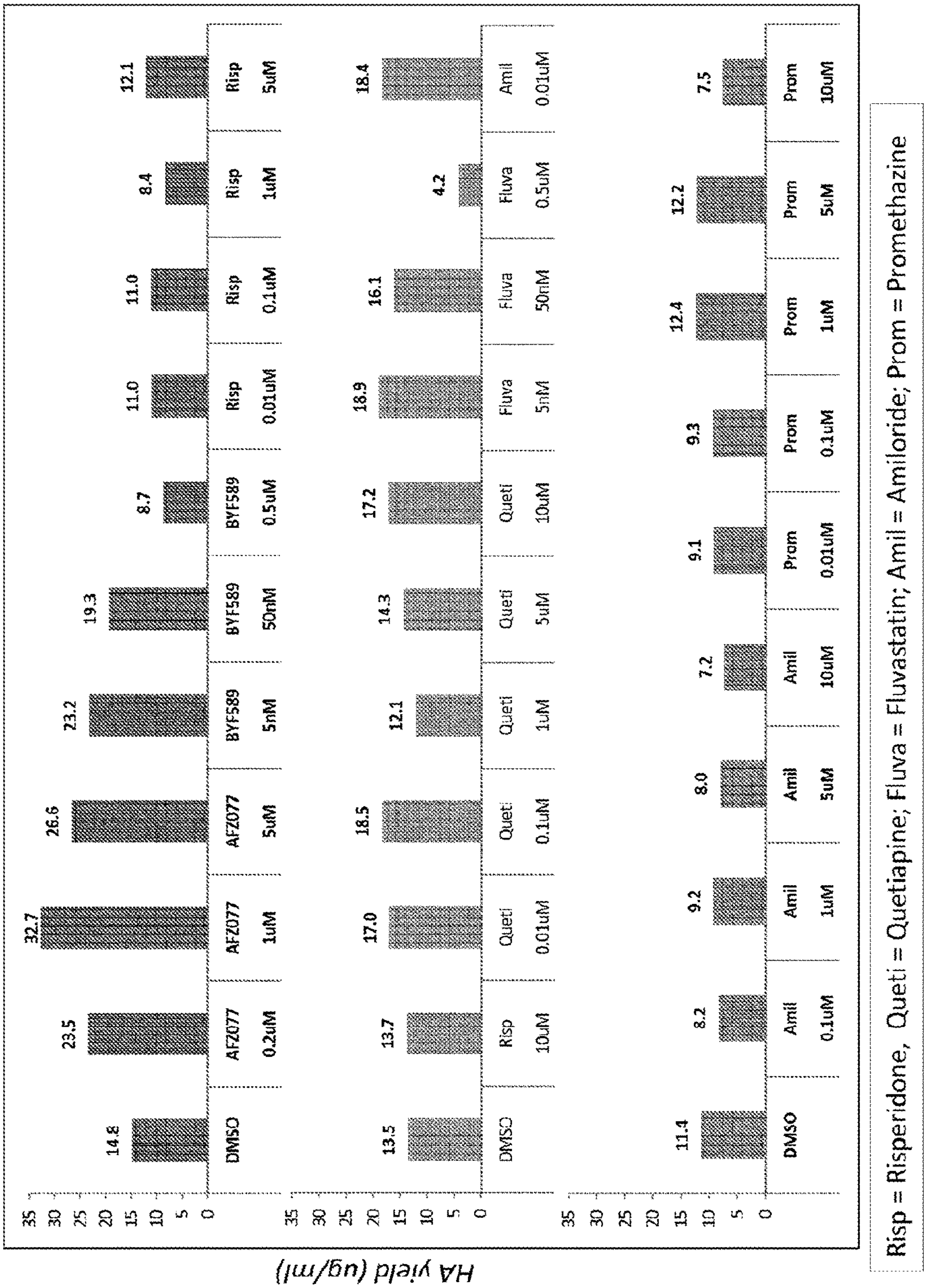
FIG. 16 summarizes ELISA results of HA yields from the A strain (IVR165); treated with indicated compounds at varying concentrations as shown.
Figure 17:
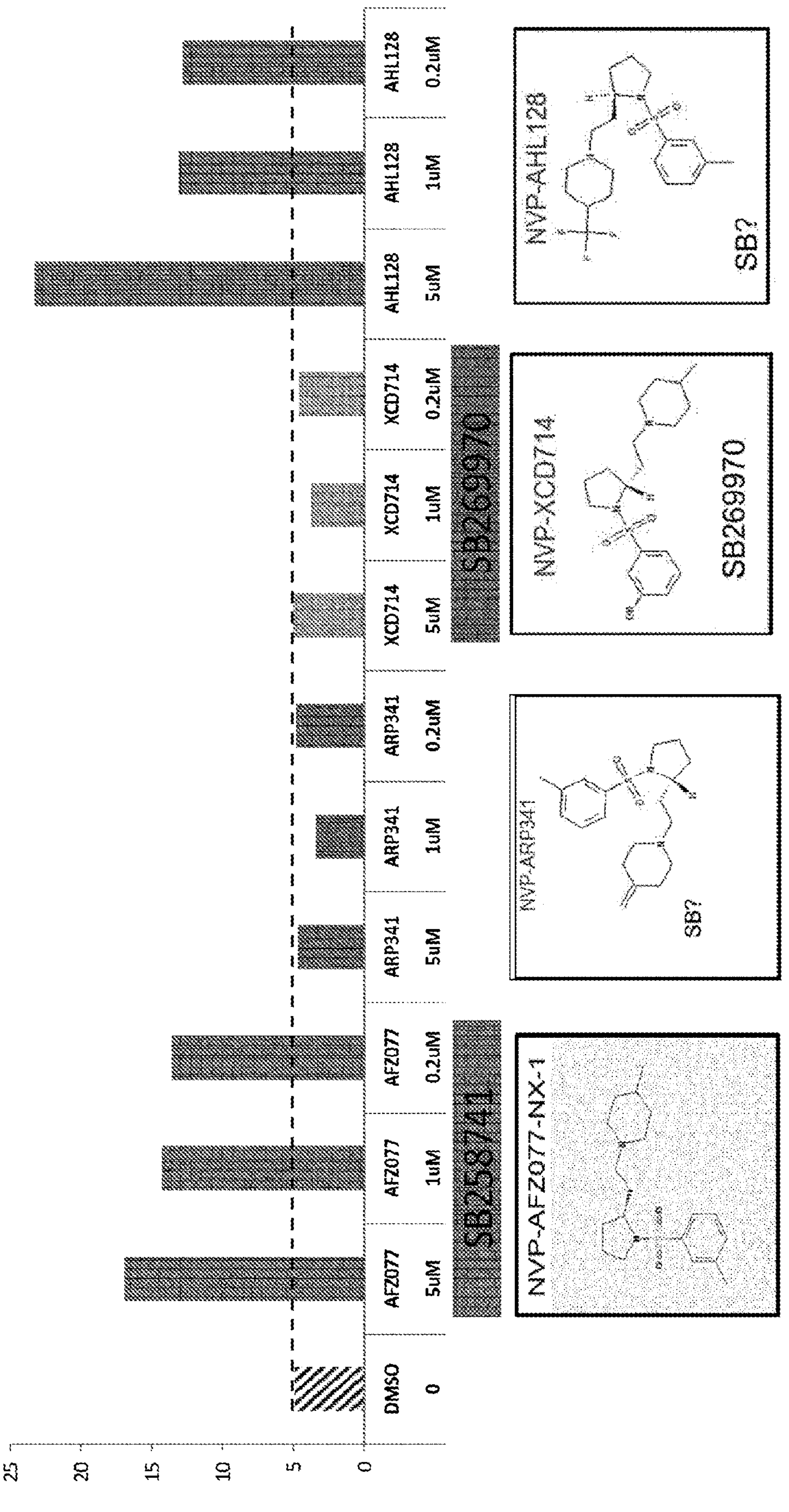
FIG. 17 provides a graph showing HA yields, relative to AFZ077, of available analogues from SAR.

Results from comparative study to evaluate relative HA yields are provided in FIG. 16. Some of these candidates were further tested for their ability to enhance HA yields relative to AFZ077 (FIG. 17).

Additional SAR studies were carried out to further identify candidate compounds to increase yields. 165 analogs tested at 0.05 uM in 10 ml viral cultures with a H3N2 strain. BYF589 enhanced yield over no-compound (DMSO) control by ~2 fold. 14 of the 165 screened were as good as or better in enhancing HA yields than BYF589 at the concentration tested. Best analogs were found to be ~2-fold better than BYF589.

Example 14—Enhancement of Recombinant Protein Expression

To further evaluate general utility of the compounds identified in the HA yield studies, one of the lead compounds, BYF589, was tested on recombinant protein expression using heterologous cells. In particular, proteins that had been previously found to be difficult to express in HEK293 cells were included, which are referred to as "low yielders." In a typical optimized system, low yielders are defined as having a yield of 5 mg/L or less. About 20 constructs of target proteins with typical yields of between 2-10 mg/L were selected for the experiments. They are secreted mammalian proteins, which are truncated versions of full length counterparts. Each construct (in a variant of the pRS5a vector) contained at least one tag (e.g., at least a C-terminal FlagHis tag—in addition, many are fused N- or C-terminally to mouse IgG1 Fc). Roughly equal numbers of each tag type were selected to reduce bias.

All targets with yields <1 mg/L or >10 mg/L were removed. Next, targets were sorted by tag type. Finally, if it looked like a particular molecular weight range was heavily represented, a few "duplicates" were culled. Then, to select samples, first 6-7 from each tag type were included without additional selection criteria. Resulting target list is reproduced below.

The BYF589 compound was dissolved in DMSO to finally provide a 70 μM working stock (1000×).

Cells used were HEK293 Freestyle cells (Life Technologies) that are from a low-passage Master Cell bank directly traceable to receipt of product. Cells were grown in HEK293F media in 2.5 L Thomson UltraYield flasks split to 0.2 million cells/ml and allowed to double 3 days to a target density of 1.5 million cells/ml. Cells were then aliquoted into 1 L standard Corning screwcap flasks at a fill volume of 300 ml before transfection. For each target, one flask had 300 ul of BYF589 added and the other did not. Cells were then transfected with PEI plasmid complex prepared as follows: Maxiprep plasmid was thawed, mixed, then indicated volume was added to 293F media. A 2 mg/ml stock of linear 25,000 MW PEI (Polysciences #23966-2) was diluted to 1 mg/ml with 293F media, then indicated volume was added to the plasmid DNA, mixed by inversion, then allowed to stand 2-10 minutes. An equal volume of PEI/DNA mix was then added to each of the two flasks (one with compound the other without), which were then swirled vigorously than returned to shaker and incubated at 37 C, 120 rpm shaking and 8% CO2 (same conditions as for growth above). The amounts used reflect our previously-optimized conditions which are (per liter) 400 ug plasmid in 1.6 ml media plus 3.2 ml of 1 mg/ml PEI.

Small sample of media supernatants were collected (Filipp Gortalum) and assayed by Octet. Correlation between initial yield untreated and the ratio of yield from treated to untreated cells.

Cell suspensions were loaded onto Ni-NTA resin column according to standard protocol. An imidazole-based purification method was used, which is well known in the art. A preliminary analysis of protein yield was done by BCA assay, which then was followed by LC90 electropherograms for confirmation.

Figure 18A:
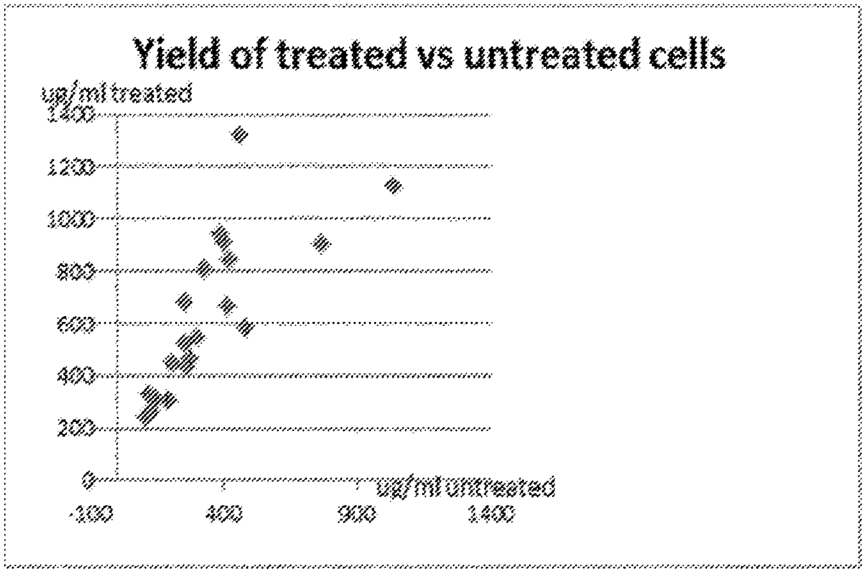
FIG. 18A and FIG. 18B provide two graphs.
Figure 18B:
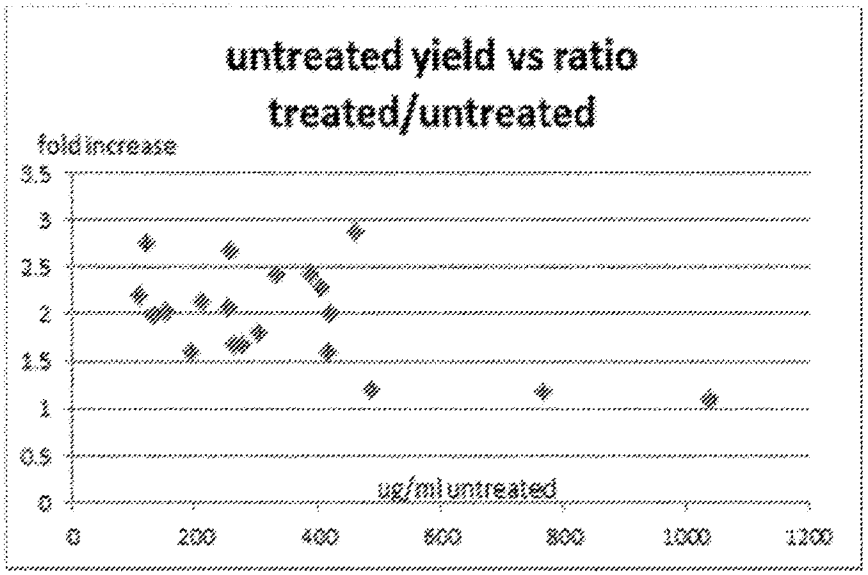

Results of the experiments are summarized in FIG. 18A and FIG. 18B. The left side graph (FIG. 18A) shows the relationship between protein yield in the presence of and in the absence of the BYF589 compound (at 70 nM). Each data point in the graph represents the 20 targets tested. The graph demonstrates the trend that the compound can increase the protein yield albeit to varying degrees. The right side graph (FIG. 18B) plots fold increase of protein yield as a function of initial yield (when untreated with the compound). It shows the general trend that proteins that tend to already have high yields ("high yielders") are not further enhanced by the presence of the compound, while the expression of low yielders are more likely to be enhanced by the compound. Among the 20 tested proteins, those with a yield of about ≤4 mg/L all show at least a 1.5 fold increase in yield when treated with the BYF589 compound, under the conditions tested. Together, these findings suggest that the compound tested exhibits a general enhancing effect on protein yield for a wide variety of proteins.

TABLE 6

| SAMPLE_NAME | PROTEIN_ID | CLONE_ID | yield in mg/L | Barcode | Native Uncleaved MW |
|---|---|---|---|---|---|
| HEK293:pRScFchAMBER-NP_000871.1-hum-177-26-177 | 411251 | 52985 | 2.9 | 152501069 | 44762 |
| HEK293:pRScFchAMBER-NP_001005609-hum-389-62-389 | 411269 | 78290 | 7.6 | 152501061 | 62057 |
| HEK293:pRScFchAMBER-NP_001165099-hum-147-28-147 | 411270 | 95023 | 5.9 | 152501016 | 41375 |
| HEK293:pRScFchAMBER-NP_001936-hum-208-20-162 | 411274 | 69558 | 5.2 | 152501037 | 43347 |
| HEK293:pRScFchAMBER-NP_003109-hum-303-18-303 | 411272 | 75329 | 9.6 | 152501064 | 60073 |
| HEK293:pRScFchAMBER-NP_005082-hum-196-22-196 | 411263 | 71090 | 1.3 | 152501035 | 46810 |
| HEK293:pRScFchAMBER-NP_006110-hum-215-23-215 | 411255 | 69518 | 2.4 | 152501071 | 49765 |
| HEK293:pRShAMBER$-NP_000197-hum-369-21-256 | 410882 | 61568 | 1.5 | 152501363 | 29825 |
| HEK293:pRShAMBER$-NP_000708-hum-312-20-293 | 410900 | 66255 | 6.0 | 152501343 | 33228 |
| HEK293:pRShAMBER$-NP_001833-hum-372-23-350 | 410890 | 61451 | 6.8 | 152501358 | 38526 |
| HEK293:pRShAMBER-NP_000651-hum-390-30-390 | 410925 | 73898 | 6.8 | 152501341 | 43310 |
| HEK293:pRShAMBER-NP_001552-hum-255-1-186 | 410914 | 87808 | 2.0 | 152501344 | 21920 |
| HEK293:pRShAMBER-NP_036599-hum-321-20-281 | 410917 | 97222 | 1.6 | 152501305 | 29919 |
| HEK293:pRSnFchAMBER$-NP_000726.1-hum-116-25-116 | 411264 | 59201 | 4.7 | 152501238 | 37581 |
| HEK293:pRSnFchAMBER$-NP_002334.2-hum-711-20-711 | 411267 | 63498 | 6.9 | 152501240 | 103704 |
| HEK293:pRSnFchAMBER$-NP_006265.1-hum-98-22-98 | 410906 | 64998 | 2.1 | 152501247 | 36175 |
| HEK293:pRSnFchAMBER$-NP_006705.1-hum-453-23-453 | 411275 | 59221 | 4.2 | 152501239 | 76279 |
| HEK293:pRSnFchAMBER-NP_000132-hum-821-27-378 | 410938 | 77435 | 4.1 | 152501274 | 66440 |
| HEK293:pRSnFchAMBER-NP_000445-hum-154-1-154 | 410913 | 95263 | 7.6 | 152501313 | 43311 |
| HEK293:pRSnFchAMBER-NP_001423-hum-169-33-118 | 410903 | 77637 | 1.0 | 152501312 | 36962 |

EMBODIMENTS OF THE INVENTION

1. A method for producing therapeutic, prophylactic or diagnostic biological molecules from a host cell system comprising contacting a host cell system with at least one chemical agent selected from Tables 1-5.
2. The method according to embodiment 1 wherein the host cell system is a cell culture or an embryonated egg.
3. The method according to any of the preceding embodiments wherein the cell culture is selected from the group consisting of MDCK, Vero, BHK, EB66 or CHO cells.
4. The method according to embodiment 1 wherein the chemical agent is a statin or analog thereof, or a serotonin receptor ligand, having a final concentration of 0.0001 μM to 10 μM.
5. The method according to any of the preceding embodiments wherein the chemical agent comprises a concentration of 0.05 μM or less and a structure as follows:

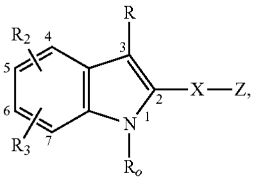
or
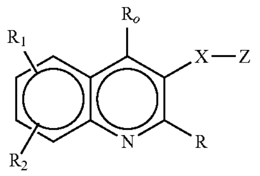

6. The method according to any of the preceding embodiments wherein the host cell system is infected with a virus.
7. The method according to embodiment 6 wherein the chemical agent is added concurrently with virus inoculation of the host cell.
8. The method according to embodiment 7 wherein virus is influenza.
9. The method according to embodiment 8 wherein the biological molecule produced by the host cell system is selected from an influenza virus particle, a split influenza virion or an influenza virus glycoprotein.
10. The method according to embodiment 9 wherein the influenza virus glycoprotein is hemagglutinin.
11. The method according to any of the preceding embodiments wherein the yield of the biological molecule produced is increased at least 2-fold compared to a control, as measured by ELISA
12. The method according to any of the preceding embodiments wherein an analog is selected from the group consisting of fluvastatin, pitavastatin, atorvastatin, cerivastatin, lovastatin, mevastatin, pravastatin or isomers thereof.
13. The method according to any of the preceding embodiments wherein the chemical agent is fluvastatin or pitavastatin or isomers thereof.
14. A method for producing a therapeutic, prophylactic or diagnostic influenza protein in a cell culture, comprising contacting a cell culture with at least one statin compound or analog thereof at a concentration of 0.05 μM or less.
15. A method for producing a therapeutic, prophylactic or diagnostic protein in a cell culture, characterized in that the production is conducted in the presence of at least one statin or derivative thereof other than simvastatin, wherein the protein is produced at least a 1.5-fold increase compared to a control, as measured by ELISA
16. The method according to embodiment 14 or 15 wherein the statin is

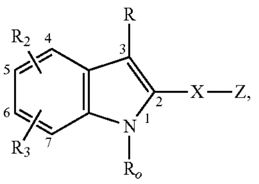
or
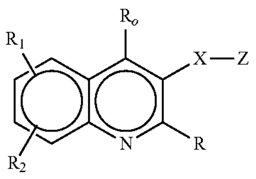

and analogs thereof.

17. The method according to embodiment 16 wherein a statin analog is selected from the group consisting of fluvastatin, pitavastatin, atorvastatin, cerivastatin, lovastatin, mevastatin, pravastatin or isomers thereof.
18. The method according to embodiment 17 wherein the statin agent is fluvastatin or pitavastatin or isomers thereof.
19. A method for producing an influenza B strain in a host cell, comprising contacting the host cell with a chemical agent that increases the yield at least 1.5 fold as measured by ELISA at a concentration of 0.05 μM or less.
20. The method according to embodiment 19 wherein the chemical agent is

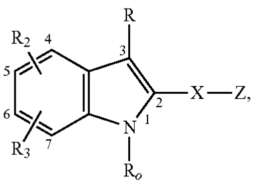
or
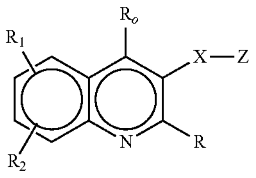

and analogs thereof.

21. The method according to embodiment 19 or 20 wherein influenza B strain virus particles, a split influenza B virion or an influenza B virus glycoprotein are produced.
22. The method according to embodiment 21 wherein the influenza B virus glycoprotein is hemagglutinin.
23. A method for producing therapeutic, prophylactic or diagnostic biological molecules from a host cell, comprising
    (a) A method as embodimented in any of the preceding embodiments
    (b) Processing the produced molecule into a final therapeutic, prophylactic or diagnostic product.
24. A method for producing an influenza vaccine in which the following steps are conducted:
    a. Growing a virus in a medium comprising a cell culture and at least one chemical agent selected from Table 1.
    b. Processing the virus to produce a sterile vaccine.
25. A method for producing an influenza B vaccine in which the following steps are conducted:
    a. Growing a virus in a medium comprising a cell culture and at least one chemical agent to produce at least a 1.5-fold increase of influenza B compared to control, as measured by ELISA and
    b. Processing the virus to produce a sterile vaccine.
26. The method according to embodiments 23-25 wherein the chemical agents are selected from Table 1 or 3.

27. A method for producing an influenza vaccine in which the following steps are conducted:

a. Growing a virus in a cell culture in the presence of a statin agent at a concentration of 0.05 μM or less.

b. Processing the virus to produce a sterile vaccine.

The invention claimed is:

1. A method for producing influenza virus particles and influenza virus proteins from suspension MDCK cells comprising:

growing or culturing the suspension MDCK cells for a duration of time, at least a portion of which is carried out in the presence of at least one chemical agent selected from the group consisting of fluvastatin, atorvastatin, cerivastatin, lovastatin, mevastatin, pravastatin or isomers thereof;

harvesting the influenza virus particles and influenza virus proteins from the suspension MDCK cells; and formulating the influenza virus particles and influenza virus proteins into a pharmaceutical composition;

wherein the at least one chemical agent has a concentration of 0.001 μM to 5 μM in culture.

2. The method according to claim 1, wherein the suspension MDCK cells are infected with an influenza virus.

3. The method according to claim 2, wherein the at least one chemical agent is added concurrently with influenza virus inoculation of the suspension MDCK cells.

4. The method according to claim 1, wherein the influenza virus particles and influenza virus proteins produced by the suspension MDCK cells are selected from influenza virus particles, split influenza virions, or influenza virus glycoproteins.

5. The method according to claim 4, wherein the influenza virus glycoproteins are hemagglutinins.

6. The method according to claim 1, wherein the yield of the influenza virus particles and influenza virus proteins produced is increased at least 1.5-fold compared to a control, as measured by ELISA.

7. The method according to claim 1, wherein the at least one chemical agent is fluvastatin or isomers thereof.

8. A method for producing influenza virus particles or influenza virus proteins from suspension MDCK cells comprising:

growing or culturing the suspension MDCK cells for a duration of time, at least a portion of which is carried out in the presence of at least one chemical agent selected from the group consisting of fluvastatin, atorvastatin, cerivastatin, lovastatin, mevastatin, pravastatin or isomers thereof;

harvesting the influenza virus particles or influenza virus proteins from the suspension MDCK cells; and formulating the influenza virus particles or influenza virus proteins into a pharmaceutical composition;

wherein the at least one chemical agent has a concentration of 0.001 μM to 5 μM in culture.

9. The method according to claim 8, wherein the suspension MDCK cells are infected with an influenza virus.

10. The method according to claim 9, wherein the at least one chemical agent is added concurrently with influenza virus inoculation of the suspension MDCK cells.

11. The method according to claim 8, wherein the influenza virus particles or influenza virus proteins produced by the suspension MDCK cells are selected from influenza virus particles, split influenza virions, or influenza virus glycoproteins.

12. The method according to claim 11, wherein the influenza virus glycoproteins are hemagglutinins.

13. The method according to claim 8, wherein the yield of the influenza virus particles or influenza virus proteins produced is increased at least 1.5-fold compared to a control, as measured by ELISA.

14. The method according to claim 8, wherein the at least one chemical agent is fluvastatin or isomers thereof.

* * * * *